(12) United States Patent
O'Connor et al.

(10) Patent No.: US 7,420,059 B2
(45) Date of Patent: Sep. 2, 2008

(54) HMG-COA REDUCTASE INHIBITORS AND METHOD

(75) Inventors: Stephen P. O'Connor, Lambertville, NJ (US); Jeffrey Robl, Newtown, PA (US); Yan Shi, Flourtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 568 days.

(21) Appl. No.: 10/989,138

(22) Filed: Nov. 15, 2004

(65) Prior Publication Data
US 2005/0171140 A1  Aug. 4, 2005

Related U.S. Application Data

(60) Provisional application No. 60/523,546, filed on Nov. 20, 2003.

(51) Int. Cl.
C07D 221/18    (2006.01)
C07D 471/02    (2006.01)
A61K 31/47     (2006.01)

(52) U.S. Cl. .................. 546/23; 546/113; 514/312

(58) Field of Classification Search .............. 546/23, 546/113
See application file for complete search history.

(56) References Cited

U.S. PATENT DOCUMENTS

| | | |
|---|---|---|
| 3,674,836 A | 7/1972 | Creger |
| 4,027,009 A | 5/1977 | Grier et al. |
| 4,046,889 A | 9/1977 | Ondetti et al. |
| 4,168,267 A | 9/1979 | Petrillo, Jr. |
| 4,316,906 A | 2/1982 | Ondetti et al. |
| 4,337,201 A | 6/1982 | Petrillo, Jr. |
| 4,374,829 A | 2/1983 | Harris et al. |
| 4,379,785 A | 4/1983 | Weyer et al. |
| 4,432,971 A | 2/1984 | Karanewsky et al. |
| 4,452,790 A | 6/1984 | Karanewsky et al. |
| 4,572,912 A | 2/1986 | Yoshioka et al. |
| 4,639,436 A | 1/1987 | Junge et al. |
| 4,722,810 A | 2/1988 | Delaney et al. |
| 4,749,688 A | 6/1988 | Haslanger et al. |
| 4,759,923 A | 7/1988 | Buntin et al. |
| 4,871,721 A | 10/1989 | Biller |
| 4,889,859 A | 12/1989 | Taylor et al. |
| 4,904,769 A | 2/1990 | Rauenbusch |
| 4,924,024 A | 5/1990 | Biller |
| 4,929,437 A | 5/1990 | Tobert |
| 4,933,165 A | 6/1990 | Brown |
| 5,034,399 A * | 7/1991 | Hubsch et al. ............. 514/300 |
| 5,100,889 A | 3/1992 | Misra et al. |
| 5,120,782 A * | 6/1992 | Hubsch et al. ............. 514/300 |
| 5,223,516 A | 6/1993 | Delaney et al. |
| 5,225,401 A | 7/1993 | Seymour |
| 5,316,765 A | 5/1994 | Folkers et al. |
| 5,346,701 A | 9/1994 | Heiber et al. |
| 5,346,900 A | 9/1994 | Gangjee |
| 5,362,727 A | 11/1994 | Robl |
| 5,366,973 A | 11/1994 | Flynn et al. |

(Continued)

FOREIGN PATENT DOCUMENTS

DE    196 22 222    12/1997

(Continued)

OTHER PUBLICATIONS

U.S. Appl. No. 10/946,055, filed Sep. 21, 2004, Ahmad et al.
Ashworth, D.M. et al., "2-Cyanopyrrolidides as Potent, Stable Inhibitors of Dipeptidyl Peptidase IV", Bioorganic & Medicinial Chemistry Letters, vol. 6, No. 10, pp. 1163-1166 (1996).
Ashworth, D.M. et al., "4-Cyanothiazolidides as Very Potent, Stable Inhibitors of Dipeptidyl Peptidase IV", Bioorganic & Medicinial Chemistry Letters, vol. 6, No. 22, pp. 2745-2748 (1996).

(Continued)

*Primary Examiner*—D. Margaret Seaman
(74) *Attorney, Agent, or Firm*—Burton Rodney

(57) ABSTRACT

Compounds are provided having the following structure

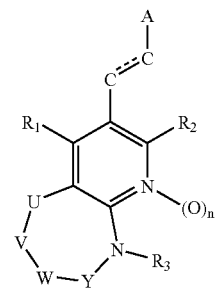

and pharmaceutically acceptable salts thereof, A is

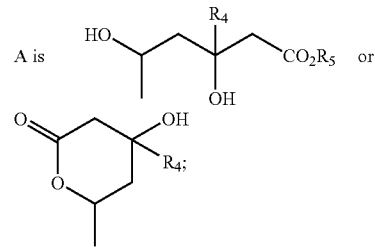

wherein $R_1$, $R_2$, $R_3$, $R_4$, U, V, W, Y, and n are as defined above, which compounds are HMG CoA reductase inhibitors and thus are active in inhibiting cholesterol biosynthesis, modulating blood serum lipids, for example, lowering LDL cholesterol and/or increasing HDL cholesterol, and treating hyperlipidemia, dyslipidemia, hypercholesterolemia, hypertriglyceridemia and atherosclerosis as well as Alzheimer's disease and osteoporosis and may be employed as hormone replacement therapy.

A method for treating the above diseases employing the above compounds is also provided.

17 Claims, No Drawings

U.S. PATENT DOCUMENTS

| | | | |
|---|---|---|---|
| 5,447,954 | A | 9/1995 | Gribble et al. |
| 5,488,064 | A | 1/1996 | Sher |
| 5,491,134 | A | 2/1996 | Sher et al. |
| 5,504,080 | A | 4/1996 | Karanewsky |
| 5,508,281 | A | 4/1996 | Gangjee |
| 5,525,723 | A | 6/1996 | Robl |
| 5,541,204 | A | 7/1996 | Sher et al. |
| 5,552,397 | A | 9/1996 | Karanewsky et al. |
| 5,594,016 | A | 1/1997 | Ueno et al. |
| 5,595,872 | A | 1/1997 | Wetterau, II et al. |
| 5,608,082 | A | 3/1997 | Varney et al. |
| 5,612,359 | A | 3/1997 | Murugesan |
| 5,614,492 | A | 3/1997 | Habener |
| 5,631,224 | A | 5/1997 | Efendic et al. |
| 5,646,141 | A | 7/1997 | Varney et al. |
| 5,646,176 | A | 7/1997 | Golik et al. |
| 5,698,527 | A | 12/1997 | Kim |
| 5,712,279 | A | 1/1998 | Biller et al. |
| 5,712,396 | A | 1/1998 | Magnin et al. |
| 5,739,135 | A | 4/1998 | Biller et al. |
| 5,760,246 | A | 6/1998 | Biller et al. |
| 5,770,615 | A | 6/1998 | Cheng et al. |
| 5,776,983 | A | 7/1998 | Washburn et al. |
| 5,827,875 | A | 10/1998 | Dickson, Jr. et al. |
| 5,885,983 | A | 3/1999 | Biller et al. |
| 5,962,440 | A | 10/1999 | Sulsky |
| 6,114,339 | A | 9/2000 | Gangjee |
| 6,218,408 | B1 | 4/2001 | Marzabadi et al. |
| 6,262,094 | B1 | 7/2001 | Hoefle et al. |
| 6,395,767 | B2 | 5/2002 | Robl et al. |
| 6,413,958 | B2 | 7/2002 | Vaillancourt |
| 6,414,126 | B1 | 7/2002 | Ellsworth et al. |
| 6,515,117 | B2 | 2/2003 | Ellsworth et al. |
| 6,548,529 | B1 | 4/2003 | Robl et al. |
| 6,573,287 | B2 | 6/2003 | Sulsky et al. |

FOREIGN PATENT DOCUMENTS

| | | |
|---|---|---|
| EP | 0 534 396 | 10/1996 |
| EP | 0 534 492 | 12/1996 |
| EP | 0 595 610 | 5/1997 |
| EP | 0 534 363 | 7/1997 |
| EP | 0 481 522 | 12/1997 |
| EP | 0 599 444 | 1/1998 |
| EP | 0 675 714 | 1/1999 |
| EP | 0 970 694 | 1/2000 |
| EP | 0 992 496 | 4/2000 |
| EP | 0 818 448 | 11/2003 |
| EP | 0 629 627 | 5/2004 |
| EP | 1 022 272 | 5/2004 |
| GB | 2 304 106 | 3/1997 |
| WO | WO 94/14787 | 7/1994 |
| WO | WO 94/15592 | 7/1994 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 99/02514 | 1/1999 |
| WO | WO 99/38501 | 8/1999 |
| WO | WO 99/44609 | 9/1999 |
| WO | WO 99/45913 | 9/1999 |
| WO | WO 99/46272 | 9/1999 |
| WO | WO 99/58518 | 11/1999 |
| WO | WO 99/58521 | 11/1999 |
| WO | WO 99/58522 | 11/1999 |
| WO | WO 99/61431 | 12/1999 |
| WO | WO 99/61435 | 12/1999 |
| WO | WO 99/64002 | 12/1999 |
| WO | WO 99/67278 | 12/1999 |
| WO | WO 99/67279 | 12/1999 |
| WO | WO 00/03746 | 1/2000 |
| WO | WO 00/15201 | 3/2000 |
| WO | WO 00/30665 | 6/2000 |
| WO | WO 00/38722 | 7/2000 |
| WO | WO 00/50574 | 8/2000 |
| WO | WO 00/53605 | 9/2000 |
| WO | WO 00/77010 | 12/2000 |
| WO | WO 01/13917 | 3/2001 |
| WO | WO 01/14376 | 3/2001 |
| WO | WO 03/011824 | 2/2003 |
| WO | WO 03/072197 | 9/2003 |

OTHER PUBLICATIONS

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, No. 1, pp. 1-40 (1996).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", J. Am. Chem. Soc., vol. 98, No. 5, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Hara, S., "Ileal $Na^+$/bile acid cotransporter inhibitors", Drugs of the Future, vol. 24, No. 4, pp. 425-430 (1999).

Hughes, T.E. et al., "NVP-DPP728: (1-[[[2-(5-Cyanopyridin-2-yl)amino]ethyl]acetyl]-2-cyano-(S)-pyrrolidine), a Slow-Binding Inhibitor of Dipeptidyl Peptidase IV", Biochemistry, vol. 38, No. 36, pp. 11597-11603 (1999).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).

Krause, B.R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of Future, vol. 24, No. 1, pp. 9-15 (1999).

Stout, D.M., "Inhibitors of Acyl-CoA:Cholesterol $O$-Acyl Transferase (ACAT) as Hypocholesterolemic Agents. 6. The First Water-Soluble ACAT Inhibitor with Lipid-Regulating Activity, etc.", Chemtracts-Organic Chemistry, vol. 8, pp. 359-362 (1995).

Takata, Y. et al., "A Comparison of the Activity of the Angiotensin Converting Enzyme Inhibitors SQ 14 225, SA 446, and MK 421", Clinical and Experimental Pharmacology & Physiology, vol. 10, pp. 131-145 (1983).

Yamada, M. et al., "A Potent Dipeptide Inhibitor of Dipeptidyl Peptidase IV", Bioorganic & Medicinal Chemistry Letters, vol. 8, pp. 1537-1540 (1998).

* cited by examiner

HMG-COA REDUCTASE INHIBITORS AND METHOD

FIELD OF THE INVENTION

This application claims a benefit of priority from U.S. Provisional Application No. 60/523,546, filed Nov. 20, 2003, the entire disclosure of which is herein incorporated by reference.

The present invention relates to compounds and pharmaceutical compositions useful as hypocholesterolemic and hypolipidemic agents. More particularly, this invention concerns (1) certain inhibitors of the enzyme 3-hydroxy-3-methylglutaryl-coenzyme A reductase (HMG-CoA reductase) that include a pyridine-containing nucleus attached by means of a linker to an HMG-binding domain sidechain, (2) pharmaceutical compositions containing such compounds and (3) a method of lowering blood serum cholesterol levels and modulating blood serum lipids employing such pharmaceutical compositions.

BRIEF DESCRIPTION OF THE INVENTION

In accordance with the present invention, there are provided certain pyridine-containing compounds that are potent inhibitors of cholesterol biosynthesis by virtue of their ability to inhibit the enzyme 3-methyl-glutaryl-coenzyme A reductase (HMG-CoA reductase).

In particular, in its broadest chemical compound aspect, the present invention provides compounds of the formula

I

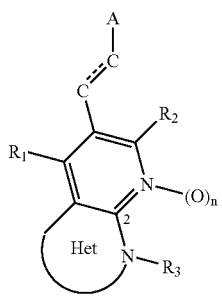

wherein

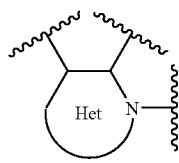

is a 5-, 6-, 7- or 8-membered non-aromatic ring which includes at least one nitrogen atom which is separated from the N atom of the pyridine ring by a fusion carbon, with the proviso that

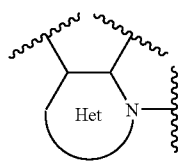

excludes (a)

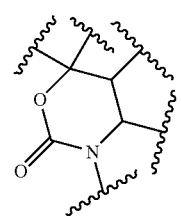

when both $R_2$ is unsubstituted alkyl or unsubstituted cycloalkyl and $R_1$ is phenyl substituted with alkyl, trifluoromethyl, hydroxymethyl, phenoxy, benzyloxy, benzyl or halogen; and (b)

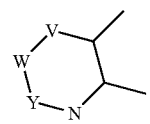

where V is $CH_2$ or

and
W—Y is —N—C(=O)—, —N—CH$_2$— or —N—C(=S)—;
and wherein

A is 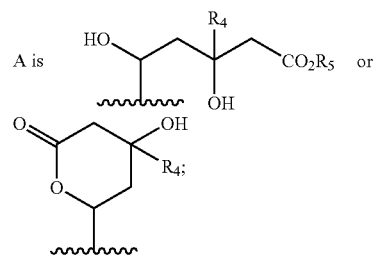

n is 0 or 1;

is
—CR$_6$R$_7$—CR$_6$R$_7$—, or
—CR$_6$=CR$_7$—;
$R_1$ and $R_2$ are the same or different and are independently selected from
H,
alkyl,
alkenyl
alkynyl,
cycloalkyl,
aryl,
or heterocyclo (wherein the attachment atom in the heterocyclo group is a carbon);
$R_3$ is selected from
H,
alkyl,
alkenyl,
alkynyl, aryl,
cycloalkyl,
heterocyclo,
$OR_8$,
$C(O)R_8$,
$CO_2R_{8a}$ (wherein $R_{8a}$ can be any of the $R_8$ groups as defined below other than H),
$C(O)NR_9R_{10}$,
$SO_2R_8$,
$SO_2NR_9R_{10}$,
$NR_9R_{10}$,
$SO_2NHCOR_8$,
$SO_2NHCO_2R_{8a}$,
$SO_2NHCONR_9R_{10}$,
$C(=NR_{11})R_{12}$,
$C(=NR_{11})NR_{12}R_{13}$, or
$C(=NR_{11})OR_8$, $R_4$ and $R_5$ are the same or different and are independently selected from H or lower alkyl;

$R_6$, $R_7$, $R_{6a}$ and $R_{7a}$ are the same or different and are independently selected from H or lower alkyl;

$R_8$ is selected from
H,
alkyl,
alkenyl,
alkynyl,
cycloalkyl,
aryl or
heterocyclo (wherein the attachment in the heterocyclo group is a carbon);

$R_{8a}$ is selected from
alkyl,
alkenyl,
alkynyl,
cycloalkyl,
aryl,
or heterocyclo (wherein the attachment atom in the heterocyclo group is a carbon);

$R_9$ and $R_{10}$ are the same or different and are independently selected from H, alkyl, alkenyl, alkynyl, cycloalkyl, aryl, or heterocyclo or $R_9$ and $R_{10}$ may be joined by an alkylene or alkenylene chain to form a 5-8 membered heterocyclo ring which is defined as for heterocyclo;

$R_{11}$, $R_{12}$, and $R_{13}$ are the same or different and are independently selected from H, nitro, cyano, $NR_{9a}R_{10a}$, $OR_{8b}$, $C(O)R_{8b}$, $C(O)NR_{9a}R_{10a}$, $CO_2R_{8c}$, $SO_2R_{8b}$, $SO_2NR_{9a}R_{10a}$, alkyl, alkenyl, alkynyl, cycloalkyl, aryl, or heterocyclo, or $R_{11}$ and $R_{12}$, or $R_{11}$ and $R_{13}$, or $R_{12}$ and $R_{13}$ may be joined by an alkylene or alkenylene chain to form a 5-8 membered heterocyclo ring which is defined as for heterocyclo, wherein $R_{8b}$ and $R_{8c}$ are the same or different and are independently selected from any of the $R_8$ and $R_{8a}$ groups defined above; and $R_{9a}$ and $R_{10a}$ are the same or different and are independently selected from any of the $R_9$ and $R_{10}$ defined above;

and including pharmaceutically acceptable salts thereof where $R_5$ is H, esters thereof, prodrug esters thereof, and all stereoisomers thereof.

In addition, in accordance with the present invention, more preferred compounds are provided which have the formula II

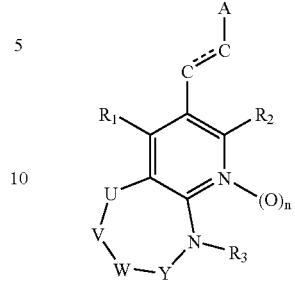

II wherein U is a direct bond, $CR^1R^2$ (where $R^1$ and/or $R^2$ are the same or different and are independently H, 'alkyl substituent',

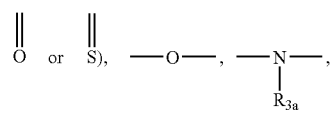

or $—S(O)_m—$ (where m is 0, 1 or 2);

V is a direct bond, $CR^3R^4$ (where $R^3$ and/or $R^4$ are the same or different and are independently H, 'alkyl substituent',

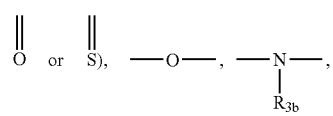

$—S(O)_m—$ (where m is 0, 1 or 2);

W is $CR^5R^6$ (where $R^5$ and/or $R^6$ are the same or different and are independently H, 'alkyl substituent',

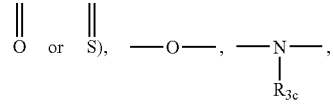

or $—S(O)_{m_1}—$ (where $m_1$ is 0, 1 or 2); and

Y is $CR^7R^8$ (where $R^7$ and/or $R^8$ are the same or different and are independently H,

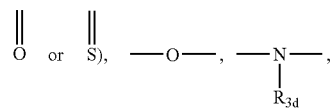

or $—S(O)_{m_2}—$ (where $m_2$ is 0, 1 or 2);

A, $R_1$, $R_2$, $R_3$ and n are as defined above, and $R_{3a}$, $R_{3b}$, $R_{3c}$ and $R_{3d}$ may be the same or different and are independently selected from any of the $R_3$ groups set out above;

and including pharmaceutically acceptable salts thereof where $R_5$ is H, esters thereof, prodrug esters thereof, and all stereoisomers thereof, with the provisos that 1. when U is a bond and V is $CR^3R^4$ (or when U is $CR^1R^2$ and V is a bond) and
  a. Y is C=O then W is other than —O— or
  b. W is —O— then Y is other than C=O or c. Y is C=O and W is —O— and
   1) $R_2$ is unsubstituted alkyl or unsubstituted cycloalkyl and $R_1$ is optionally substituted phenyl,
      then $R^3$ and $R^4$ (or $R^1$ and $R^2$) are other than H or alkyl substituted with hydroxyl, halogen, cyano or $C_1$-$C_4$ alkoxy; or
   2) $R_2$ is unsubstituted alkyl or unsubstituted cycloalkyl and $R^3$ and $R^4$ (or $R^1$ and $R^2$) are the same or different and are independently H or alkyl substituted with hydroxyl, halogen, cyano or C1-C4 alkoxy,
      then $R_1$ is other than optionally substituted phenyl; or
   3) $R_1$ is optionally substituted phenyl and $R^3$ and $R^4$ (or $R^1$ and $R^2$) are the same or different and are independently H or alkyl substituted with hydroxyl, halogen, cyano or C1-C4 alkoxy,
      then $R^2$ is other than unsubstituted alkyl or unsubstituted cycloalkyl;
2. where U is a bond and V is $CH_2$ or

(or where U is $CH_2$ and V is a bond), then W—Y together are other than —N—C(O)—, —N—$CH_2$— or —N—C(S)—.

In preferred embodiments
U—V—W—Y is selected from the following:

|     | U*     | V*     | W*     | Y*     |
| --- | ------ | ------ | ------ | ------ |
| i   | bond   | bond   | $CH_2$ | $CH_2$ |
| ii  | bond   | bond   | $CH_2$ | $SO_2$ |
| iii | bond   | bond   | $CH_2$ | C=O    |
| iv  | bond   | $CH_2$ | $CH_2$ | $CH_2$ |
| v   | bond   | $CH_2$ | $CH_2$ | $SO_2$ |
| vi  | bond   | $CH_2$ | $CH_2$ | C=O    |
| vii | bond   | $CH_2$ | O      | $CH_2$ |
| viii| bond   | C=O    | $CH_2$ | $CH_2$ |
| ix  | bond   | C=O    | $CH_2$ | $SO_2$ |
| x   | bond   | C=O    | $NR_3$ | $SO_2$ |
| xi  | $CH_2$ | $CH_2$ | $CH_2$ | $CH_2$ |
| xii | $CH_2$ | $CH_2$ | $CH_2$ | $SO_2$ |
| xiii| $CH_2$ | $CH_2$ | $CH_2$ | C=O    |
| xiv | $CH_2$ | O      | $CH_2$ | $CH_2$ |
| xv  | $CH_2$ | C=O    | $CH_2$ | $SO_2$ |

*one or both of the hydrogen atoms may be replaced by an 'alkyl substituent'.

Preferably, the A group will be in form of a free acid, a physiologically acceptable and hydrolyzable ester or δ lactone thereof, or an alkali metal salt, alkaline earth metal salt or an amine salt or an amino acid salt.

Preferred are compounds of formula II of the invention wherein $R_1$ and $R_2$ are the same or different and are independently selected from alkyl, cycloalkyl and aryl;

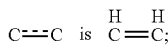

$R_3$ is selected from H, alkyl, $SO_2R_{8a}$, or $C(O)R_8$;
$R_4$ is H;
U is selected from —$CH_2$— (wherein one or both of the hydrogen atoms may be replaced by an 'alkyl substituent'), or a bond;

V is selected from

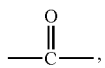

—O—, —$CH_2$— (wherein one or both of the hydrogen atoms may be replaced by an 'alkyl substituent') or a bond;
W is selected from —$CH_2$— (wherein one or both of the hydrogen atoms may be replaced by an 'alkyl substituent'), —O— or N—$R_{3c}$;
Y is selected from —$CH_2$— (wherein one or both of the hydrogen atoms may be replaced by an 'alkyl substituent'), —$SO_2$— or C=O;
n is O;
with the provisos 1. and 2. as previously set out herein.

More preferred are compounds of formula II of the invention wherein

is trans

$R_1$ is aryl,
$R_2$ is selected from alkyl or cycloalkyl,
$R_3$ is selected from H, alkyl, $SO_2R_{8a}$, or $C(O)R_8$,
$R_4$ is H,
U is selected from —$CH_2$— (wherein one or both of the hydrogen atoms may be replaced by an 'alkyl substituent'), or a bond,
V is selected from

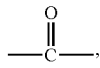

—O—, —$CH_2$— (wherein one or both of the hydrogen atoms may be replaced by an 'alkyl substituent') or a bond,
W is selected from —$CH_2$— (wherein one or both of the hydrogen atoms may be replaced by an 'alkyl substituent'), or —O—,
Y is selected from —$CH_2$— (wherein one or both of the hydrogen atoms may be replaced by an 'alkyl substituent'), —$SO_2$— or C=O,
n is 0,
with the provisos 1 and 2 as set out hereinbefore.

Still more preferred are compounds of formula II of the invention wherein
$R_1$ is 4-fluorophenyl,
$R_2$ is isopropyl,
$R_3$ is selected from H, $SO_2CH_3$, $SO_2CH_2CH_3$, $SO_2$(1-methylimidazol-4-yl), $SO_2CH(CH_3)_2$, $SO_2Ph$, $C(O)CH_3$, or $CH_3$,
$R_4$ is H,
and U, V, W and Y are —$CH_2CH_2$— compound (i), —$CH_2CH_2CH_2$— compound (iv),

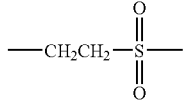

compound (v), —CH$_2$OCH$_2$— compound (vii), —CH$_2$—CH$_2$—CH$_2$—CH$_2$— compound (xi),

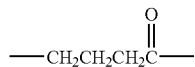

compound (xiii) or —CH$_2$—O—CH$_2$CH$_2$— compound (xiv), (wherein one or both of the hydrogen atoms may be replaced by an alkyl)

n is 0 and

A is 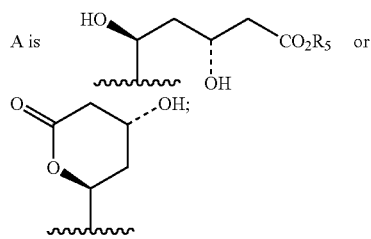

or an alkali metal salt thereof, alkaline earth metal salt or an amino acid salt.

Most preferred compounds are (including names and corresponding structures)

7-[4-(4-fluorophenyl)-5,6,7,8-tetrahydro-2-(1-methylethyl)-8-(methylsulfonyl)-1,8-naphthyridin-3-yl]-3,5-dihydroxy-(3R,5S,6E)-6-heptenoic acid, monosodium salt.

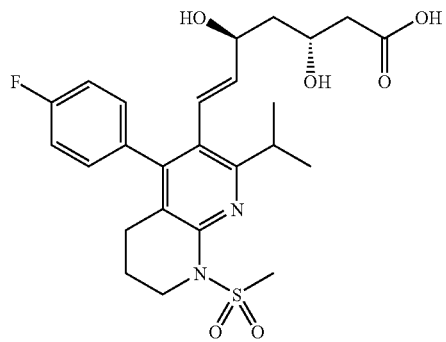

7-[4-(4-fluorophenyl)-5,6,7,8-tetrahydro-2-(1-methylethyl)-8-(phenylsulfonyl)-1,8-naphthyridin-3-yl]-3,5-dihydroxy-(3R,5S,6E)-6-heptenoic acid, monosodium salt.

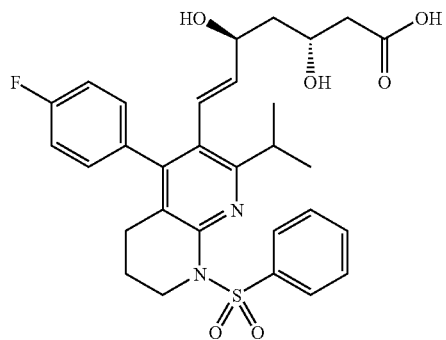

7-[4-(4-fluorophenyl)-5,6,7,8-tetrahydro-2-(1-methylethyl)-8-[(1-methylethyl)sulfonyl]-1,8-naphthyridin-3-yl]-3,5-dihydroxy-(3R,5S,6E)-6-heptenoic acid, monosodium salt.

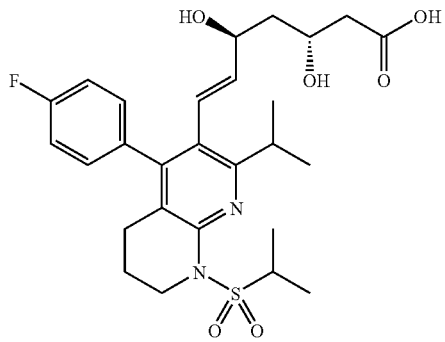

7-[6-(4-fluorophenyl)-1,2,3,5-tetrahydro-8-(1-methylethyl)-1-(methylsulfonyl)pyrido[2,3-e][1,4]oxazepin-7-yl]-3,5-dihydroxy-(3R,5S,6E)-6-heptenoic acid, monosodium salt.

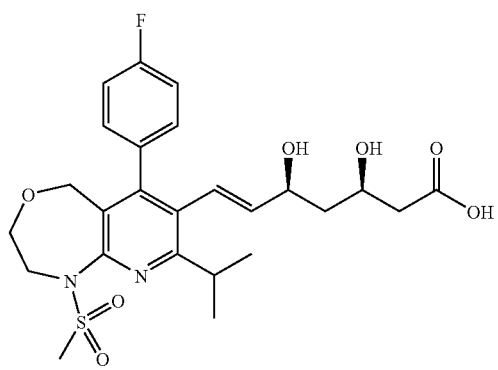

7-[4-(4-fluorophenyl)-5,6,7,8-tetrahydro-2-(1-methylethyl)-8-[(1-methyl-1H-imidazol-4-yl)sulfonyl]-1,8-naphthyridin-3-yl]-3,5-dihydroxy-(3R,5S,6E)-6-heptenoic acid, monosodium salt.

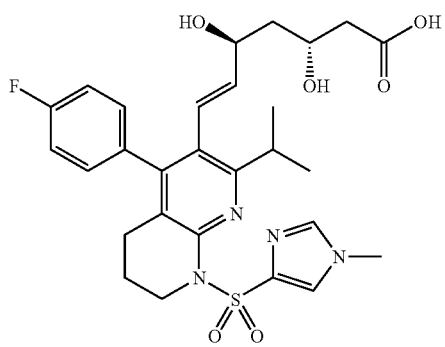

7-[5-(4-fluorophenyl)-1,4-dihydro-7-(1-methylethyl)-1-(methylsulfonyl)-2H-pyrido[2,3-d][1,3]oxazin-6-yl]-3,5-dihydroxy-(3R,5S,6E)-6-heptenoic acid, monosodium salt.

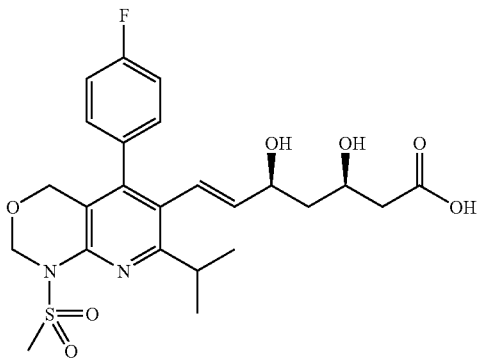

7-[8-(ethylsulfonyl)-4-(4-fluorophenyl)-5,6,7,8-tetrahydro-2-(1-methylethyl)-1,8-naphthyridin-3-yl]-3,5-dihydroxy-(3R,5S,6E)-6-heptenoic acid, monosodium salt.

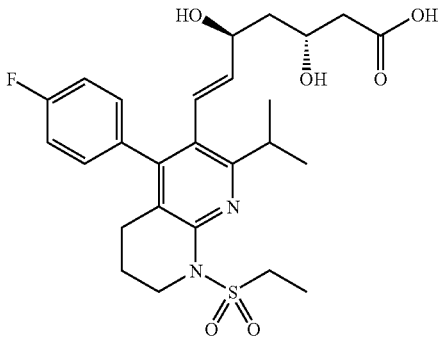

7-[4-(4-fluorophenyl)-6,7,8,9-tetrahydro-2-(1-methylethyl)-9-(methylsulfonyl)-5H-pyrido[2,3-b]azepin-3-yl]-3,5-dihydroxy-(3R,5S,6E)-6-heptenoic acid, monosodium salt.

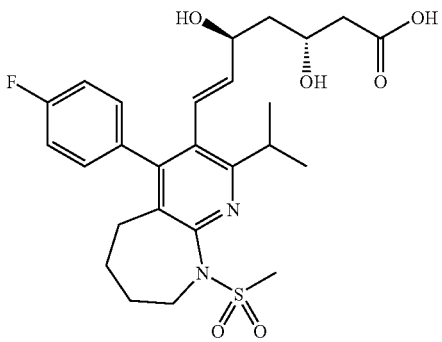

7-[4-(4-fluorophenyl)-5,6,7,8-tetrahydro-2-(1-methylethyl)-1,8-naphthyridin-3-yl]-3,5-dihydroxy-(3R,5S,6E)-6-heptenoic acid, monosodium salt.

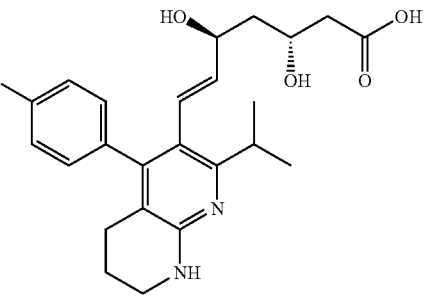

7-[8-acetyl-4-(4-fluorophenyl)-5,6,7,8-tetrahydro-2-(1-methylethyl)-1,8-naphthyridin-3-yl]-3,5-dihydroxy-(3R,5S,6E)-6-heptenoic acid, monosodium salt.

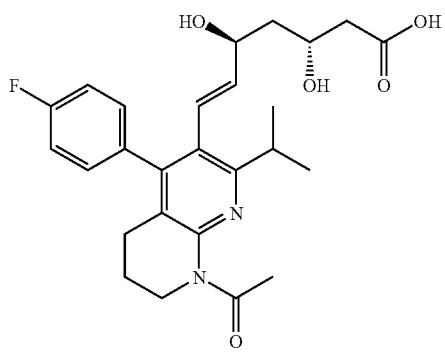

7-[5-(4-fluorophenyl)-3,4-dihydro-1-methyl-7-(1-methylethyl)-2,2-dioxido-1H-pyrido[2,3-c][1,2]thiazin-6-yl]-3,5-dihydroxy-(3R,5S,6E)-6-heptenoic acid, monosodium salt.

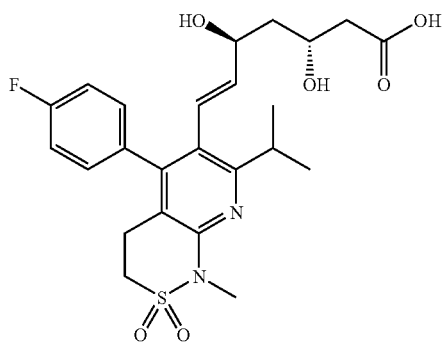

7-[4-(4-fluorophenyl)-2,3-dihydro-6-(1-methylethyl)-1-(methylsulfonyl)-1H-pyrrolo[2,3-b]pyridin-5-yl]-3,5-dihydroxy-(3R,5S,6E)-6-heptenoic acid, monosodium salt.

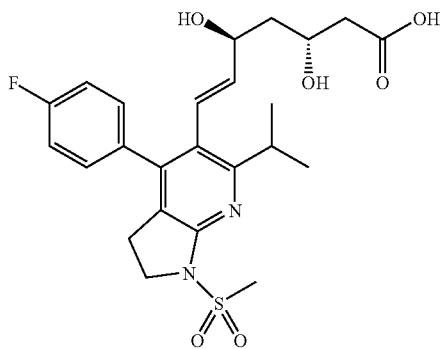

7-[(3R)-6-(4-fluorophenyl)-1,2,3,5-tetrahydro-3-methyl-8-(1-methylethyl)-1-(methylsulfonyl)pyrido[2,3-e][1,4]oxazepin-7-yl]-3,5-dihydroxy-(3R,5S,6E)-6-heptenoic acid, monosodium salt.

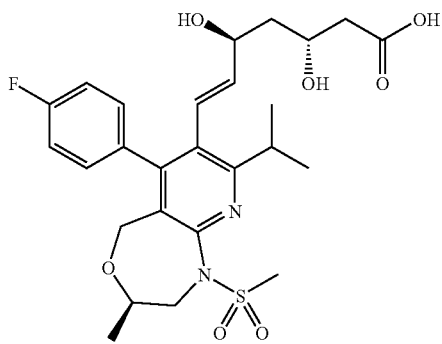

7-[4-(4-fluorophenyl)-5,6,7,8-tetrahydro-8-methyl-2-(1-methylethyl)-1,8-naphthyridin-3-yl]-3,5-dihydroxy-(3R,5S,6E)-6-heptenoic acid, monosodium salt.

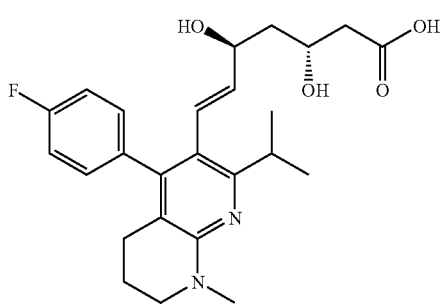

7-[(2R)-6-(4-fluorophenyl)-1,2,3,5-tetrahydro-2-methyl-8-(1-methylethyl)-1-(methylsulfonyl)pyrido[2,3-e][1,4]oxazepin-7-yl]-3,5-dihydroxy-(3R,5S,6E)-6-heptenoic acid, monosodium salt.

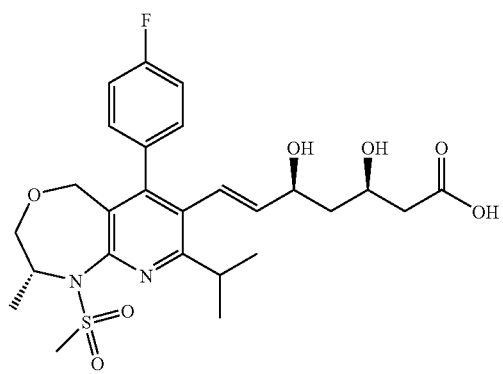

7-[4-(4-fluorophenyl)-6,7,8,9-tetrahydro-9-methyl-2-(1-methylethyl)-8-oxo-5H-pyrido[2,3-b]azepin-3-yl]-3,5-dihydroxy-(3R,5S,6E)-6-heptenoic acid, monosodium salt.

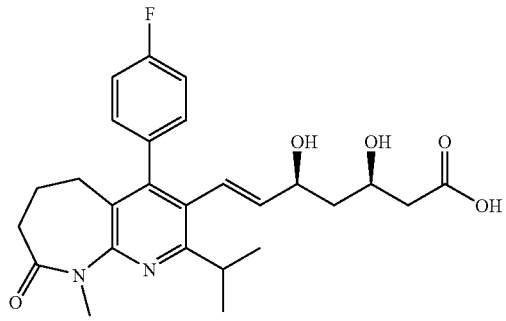

7-[(2S)-6-(4-fluorophenyl)-1,2,3,5-tetrahydro-2-methyl-8-(1-methylethyl)-1-(methylsulfonyl)pyrido[2,3-e][1,4]oxazepin-7-yl]-3,5-dihydroxy-(3R,5S,6E)-6-heptenoic acid, monosodium salt.

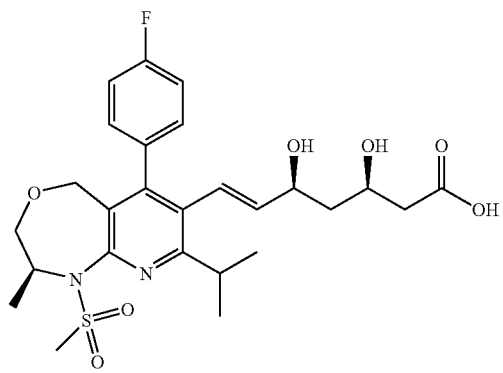

7-[(3S)-6-(4-fluorophenyl)-1,2,3,5-tetrahydro-3-methyl-8-(1-methylethyl)-1-(methylsulfonyl)pyrido[2,3-e][1,4]oxazepin-7-yl]-3,5-dihydroxy-(3R,5S,6E)-6-heptenoic acid, monosodium salt.

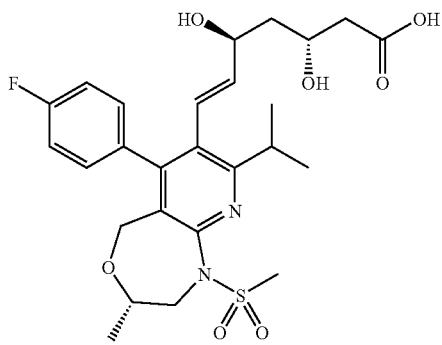

7-[1-(ethylsulfonyl)-6-(4-fluorophenyl)-1,2,3,5-tetrahydro-8-(1-methylethyl)pyrido[2,3-e][1,4]oxazepin-7-yl]-3,5-dihydroxy-(3R,5S,6E)-6-heptenoic acid, monosodium salt.

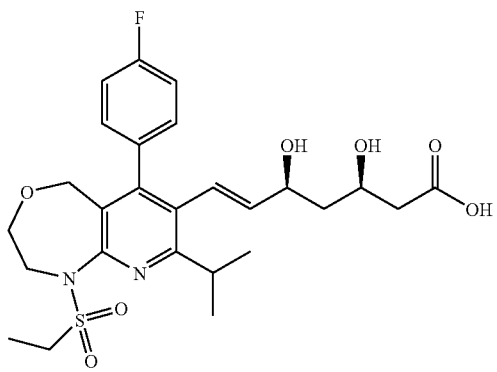

7-[(2S)-1-(ethylsulfonyl)-6-(4-fluorophenyl)-1,2,3,5-tetrahydro-2-methyl-8-(1-methylethyl)pyrido[2,3-e][1,4]oxazepin-7-yl]-3,5-dihydroxy-(3R,5S,6E)-6-heptenoic acid, monosodium salt.

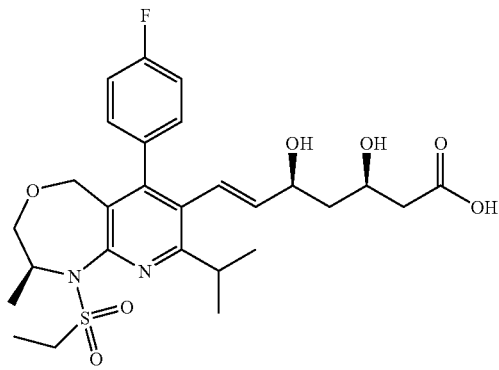

7-[4-(4-fluorophenyl)-5,6,7,8-tetrahydro-2-(1-methylethyl)-8-(methylsulfonyl)-1,8-naphthyridin-3-yl]-3,5-dihydroxy-(3R,5R,6E)-6-heptenoic acid, monosodium salt.

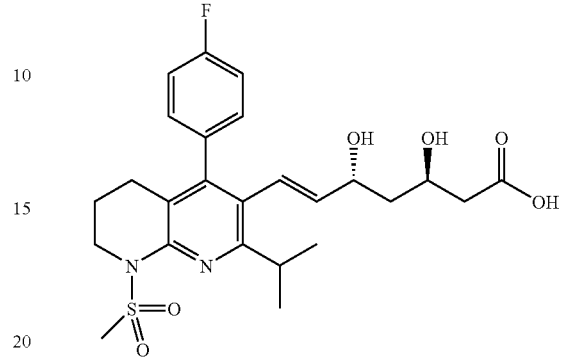

In addition in accordance with the present invention, novel intermediates for use in preparing compounds of formulae I and II are provided which have the following structures:

a)

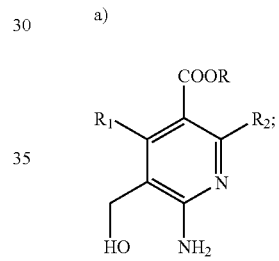

9 b)

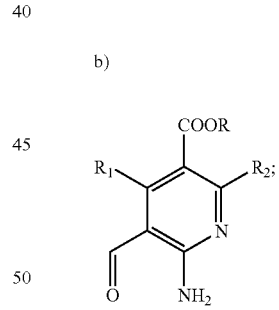

10 c)

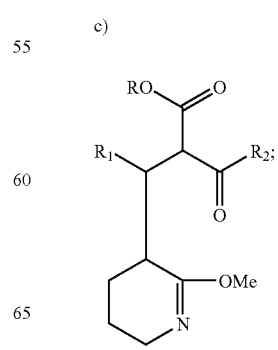

48

-continued
d)
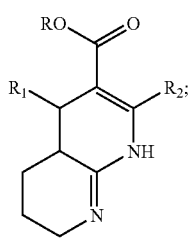
e)
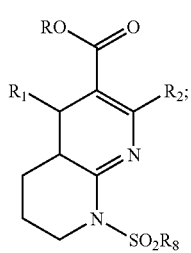
f)
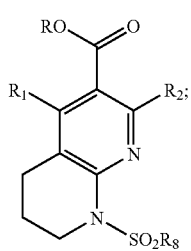
g)
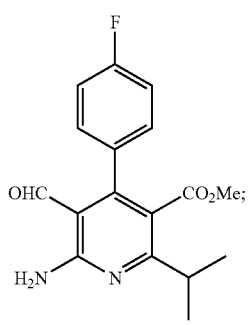
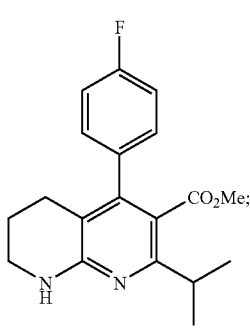
-continued
i)
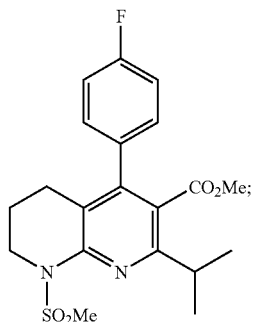
j)
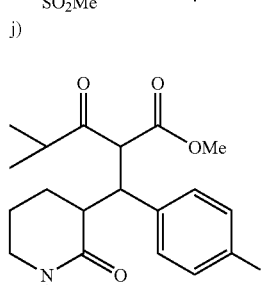
k)
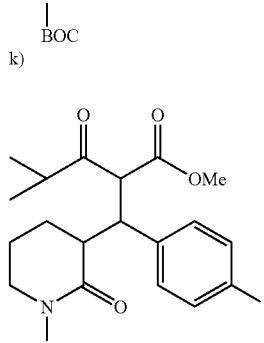
l)
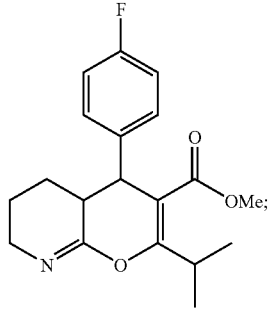
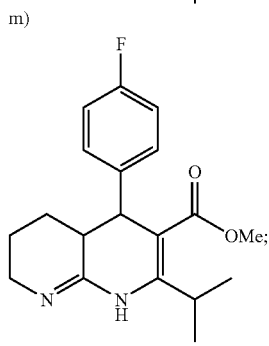

n)

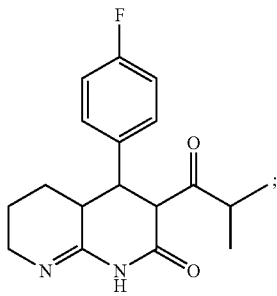

wherein R is alkyl, alkenyl, aryl or a silyl group;

$R_1$ and $R_2$ are the same or different and are independently selected from H, alkyl, alkenyl, alkynyl, cycloalkenyl, aryl or heterocyclo (where the attachment atom in the heterocyclo group is a carbon); and $R_8$ is
H,
alkyl,
alkenyl,
alkynyl,
cycloalkenyl,
aryl or
heterocyclo (wherein the attachment in the heterocyclo group is a carbon).

Still further in accordance with the present invention, processes are provided for preparing the above intermediates for use in preparing compounds of formula I and II of the invention.

In another aspect, the present invention provides pharmaceutical compositions useful as hypolipidemic or hypocholesterolemic agents, or hypotriglyceridemic agents, or anti-Alzheimer's agents, or anti-osteoporosis agents as well as other uses as described herein, which contain a hypolipidemic or hypocholesterolemic or hypotriglyceridemic or anti-Alzheimer's disease or anti-osteoporosis amount, or other therapeutically effective amount (depending upon use) of a compound of formula I or II in accordance with this invention, in combination with a pharmaceutically acceptable carrier.

In another aspect, the present invention provides a method of inhibiting cholesterol biosynthesis or lowering blood serum cholesterol levels and/or modulating blood serum cholesterol levels such as lowering LDL cholesterol and/or increasing HDL cholesterol, and/or lowering triglycerides, or treating dyslipidemia, mixed dyslipidemia, hyperlipidemia, hypercholesterolemia, hypo α-lipoproteinemia, LDL Pattern B, LDL Pattern A, hyperlipoproteinemia or hypertriglyceridemia, and other aberrations of apolipoprotein B metabolism, or reducing levels of Lp(a); or treating or preventing other cholesterol-related diseases, or treating or preventing or reversing progression of atherosclerosis, or preventing or treating Alzheimer's disease, or preventing or treating osteoporosis and/or osteopenia, or reducing inflammatory markers such as C-reactive protein, or preventing or treating low grade vascular inflammation, or preventing or treating stroke, or preventing or treating dementia, or preventing and treating coronary heart disease (including primary and secondary prevention of myocardial infarction), or preventing or treating stable and unstable angina, or primary prevention of coronary events, or secondary prevention of cardiovascular events, or preventing or treating peripheral vascular disease, preventing or treating peripheral arterial disease, or preventing or treating acute vascular syndromes, or preventing or reducing the risk of undergoing myocardial revascularization procedures, or preventing or treating microvascular diseases such as nephropathy, neuropathy, retinopathy and nephrotic syndrome or preventing or treating hypertension in a patient in need of such treatment by administering a therapeutically effective amount of a compound of structure I or II or pharmaceutical composition containing same in accordance with the present invention as defined above.

In addition, in accordance with the present invention, a method is provided for preventing or treating diabetes, especially Type 2 diabetes, and related diseases such as insulin resistance, hyperglycemia, hyperinsulinemia, elevated blood levels of fatty acids or glycerol, obesity, Syndrome X, diabetic complications, dysmetabolic syndrome, and related diseases, and sexual dysfunction, wherein a therapeutically effective amount of a compound of structure I or II or composition containing same is administered to a patient in need of treatment.

In addition, in accordance with the present invention, a method is provided for preventing and treating malignant lesions (such as ductal carcinoma in situ of the breast and lobular carcinoma in situ of the breast), premalignant lesions (such as fibroadenoma of the breast and prostatic intraepithelial neoplasia (PIN), gastrointestinal malignencies, liposarcomas and various other epithelial tumors (including breast, prostate, colon, ovarian, gastric and lung), cancer-induced asthenia (fatigue), irritable bowel syndrome, Crohn's disease, gastric ulceritis, and gallstones, and HIV infection, other infectious diseases, drug-induced lipodystrophy, and proliferative diseases such as psoriasis, wherein a therapeutically effective amount of a compound of structure I or II or a composition containing same is administered to a human patient in need of treatment.

In addition, in accordance with the present invention, a method is provided for improving coagulation homeostasis including reducing plasminogen activating inhibitor (PAI)-1 activity, reducing fibrinogen, and/or reducing platelet aggregation, and/or improving endothelial function, wherein a therapeutically effective amount of a compound of structure I or II or a composition containing same is administered to a patient in need of treatment.

In addition, in accordance with the present invention, a method is provided for treating cholesterol related diseases, diabetes and related diseases, cardiovascular diseases, cerebrovascular diseases as defined above and hereinafter and other diseases as set out above, wherein a therapeutically effective amount of a combination of a compound of structure I or II and a hypolipidemic agent, and/or lipid modulating agent and/or antidiabetic agent and/or cardiovascular agent, cerebrovascular agent, and/or other type of therapeutic agent, is administered to a patient in need of treatment.

In the above methods of the invention wherein a combination is administered, the compound of structure I or II will be employed in a weight ratio to the other therapeutic agent (depending upon its mode of operation) within the range from about 0.01:1 to about 500:1, preferably from about 0.5:1 to about 100:1.

DETAILED DESCRIPTION OF THE INVENTION

In accordance with the present invention, there is provided compounds useful in inhibiting the enzyme HMG-CoA reductase, which inhibitors are useful as hypocholesterolemic agents, dyslipidemic agents, hypolipidemic agents, hypotriglyceridemic agents, anti-Alzheimer's disease agents, and antiosteoporosis agents as well as other uses as described herein.

The term "coronary events" as employed herein refers to myocardial infarction, myocardial revascularization procedures, angina, cardiovascular death and acute coronary syndrome.

The term "cardiovascular diseases or events" as employed herein refers to atherosclerosis of the coronary arteries, myocardial infarction, including primary MI and secondary MI, recurrent myocardial infarction, angina pectoris (including stable and unstable angina), congestive heart failure, and sudden cardiac death.

The term "cerebrovascular diseases or events" as employed herein refers to cerebral infarction or stroke (caused by vessel blockage or hemorrhage), or transient ischemia attack (TIA), syncope, atherosclerosis of the intracranial and/or extracranial arteries, and the like.

The term "cholesterol-related diseases" as employed herein refers to diseases involving elevated levels of LDL cholesterol, diseases involving regulation of LDL receptors, diseases involving reduced levels of HDL cholesterol, dyslipidemia, hyperlipidemia, elevated LDL Pattern B, elevated LDL Pattern A, hypercholesterolemia, hypo $\alpha$-lipoproteinemia (low HDL cholesterol syndrome), hyperlipoproteinemia, elevated Lp(a) levels, hypertriglyceridemia, other aberrations of apolipoprotein B metabolism, heterozygous familial, presumed familial combined and non-familial (non-FH) forms of primary hypercholesterolemia (including Frederickson Types IIa and IIb), cholesterol ester storage disease, and cholesterol ester transfer protein disease, and related diseases.

The conditions, diseases, and maladies collectively referenced to as "Syndrome X" or Dysmetabolic Syndrome (as detailed in Johanson, *J. Clin. Endocrinol. Metab.*, 1997, 82, 727-734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), other types of anti-atherosclerosis agents, and/or one or more antiplatelet agents, one or more agents for treating hypertension, one or more anti-cancer drugs, one or more agents for treating arthritis, one or more anti-osteoporosis agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

The term "other types of anti-atherosclerosis agents" as employed herein refers to conventional anti-atherosclerosis agents including lipoxygenase inhibitors, ACAT inhibitors, PPAR$\alpha$ agonists, dual PPAR$\alpha$/$\gamma$ agonists, CETP inhibitors, antioxidants, PPAR $\delta$ agonists, phospholipase inhibitors including PLA-2 inhibitors and/or other known anti-atherosclerotic agents.

The terms pharmaceutically acceptable "salt" and "salts" refer to basic salts formed with inorganic and organic bases. Such salts include ammonium salts; alkali metal salts, such as lithium, sodium and potassium salts; alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product. Preferred are sodium and calcium salts.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium or choline, amino acid salts such as lysine (D or L), amine salts such as diethanolamine, ethylenediamine, t-butylamine, t-octylamine, tris-(hydroxymethyl)aminomethane (TRIS), N-methyl glucosamine (NMG), triethanolamine, dicyclohexylamine, methylamine and dehydroabietylamine.

Unless otherwise indicated, the term "alkyl" or "alk" as employed herein alone or as part of another group includes both straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Lower alkyl refers to such groups containing 1-6 carbon atoms. Unless specified otherwise, alkyl groups may be optionally substituted with 1 or more 'alkyl substituents' which may be the same or different at each occurrence. These substituents may occur at any place and in any combination that provides a stable compound. These substituents may be halogen, nitro, cyano, $OR_{14}$, alkyl which may be substituted with one or more occurrences of $R_{15}$, alkenyl which may be substituted with one or more occurrences of $R_{15}$, alkynyl which may be substituted with one or more occurrences of $R_{15}$, cycloalkyl which may be substituted with one or more occurrences of $R_{15}$, aryl which may be substituted with one or more occurrences of $R_{15}$, heterocyclo which may be substituted with one or more occurrences of $R_{15}$, $SR_{14}$,
$SO_2R_{14}$,
$COOR_{14}$,
$C(O)R_{14}$,
$CONR_{16}R_{17}$,
$SO_2NR_{16}R_{17}$,
$SO_2N(H)C(O)R_{14}$,
$SO_2N(H)CO_2R_{14}$ wherein $R_{14}$ is not H,
$NR_{16}R_{17}$,
$N(R_{16})SO_2R_{17}$,
$N(R_{16})C(O)_mR_{17}$ (m=1,2),
$N(R_{16})C(O)NR_{17}R_{18}$,
$N(R_{16})SO_2NR_{17}R_{18}$,
$OC(O)R_{14}$,
$OC(O)OR_{14}$,
$OC(O)NR_{17}R_{18}$,
$C(O)N(H)SO_2NR_{17}R_{18}$,
$C(O)N(H)SO_2R_{17}$,
oxo (or keto, i.e. =O),
thioxo (i.e., =S),
imino (i.e. =NR_{19}),
$NR_{19}—C(=NR_{20})R_{21}$,
$NR_{19}—C(=NR_{20})NR_{21}R_{22}$,
$C(=NR_{19})NR_2OR_{21}$,
$OC(=NR_{19})NR_2OR_{21}$,
$OC(=NR_{19})R_{20}$,
$C(=NR_{19})R_{20}$,
$C(=NR_{19})OR_{14}$, $R_{14}$ is selected from H, $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo each of which may be substituted with 1 to 3 independent occurrences of $R_{15}$, $R_{16}$, $R_{17}$, and $R_{18}$ are the same or different and are independently selected from $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo each of which may be substituted with 1 to 3 independent occurrences of $R_{15}$, or $R_{16}$ and $R_{17}$, or $R_{16}$ and $R_{18}$ or $R_{17}$ and $R_{18}$ may be joined by an alkylene or an alkenylene chain to form a 5- to 8-membered heterocyclo ring which is defined as for heterocyclo wherein the substituents may be one or more occurrences of $R_{15}$, $R_{19}$, $R_{20}$, $R_{21}$, or $R_{22}$ are the same or different and are independently selected from H, nitro, cyano, OH, O($C_1$-$C_6$ alkyl), $C(O)R_{14}$, $C(O)NR_{16}R_{17}$, $CO_2R_{14}$ (with the proviso that $R_{14}$ is not H), $SO_2R_{14}$, $SO_2NR_{16}R_{17}$, $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo or $R_{19}$ and $R_{20}$ or $R_{19}$ and $R_{21}$ or $R_{19}$ and $R_{22}$ or $R_{20}$ and $R_{21}$ or $R_{20}$ and $R_{22}$ or $R_{21}$ and $R_{22}$ may be joined by an alkylene or alkenylene chain to form a 5-8 membered ring that may be optionally substituted with one or more occurrences of $R_{15}$.

$R_{15}$ is selected from
halogen,
nitro,
cyano,
$OR_{24}$,
alkyl optionally substituted with halogen,
cycloalkyl optionally substituted with halogen,
aryl optionally substituted with halogen, hydroxy, nitro, methoxy, trifluoromethyl, cyano, carbomethoxy, $CONH_2$, or CHO,
heterocyclo optionally substituted with halogen, hydroxy, nitro, methoxy, trifluoromethyl, cyano, carbomethoxy, $CONH_2$, or CHO,
$SR_{24}$,
$CO_2R_{24}$,
$C(O)R_{24}$,
$CONR_{25}R_{26}$,
$SO_2NR_{25}R_{26}$,
$NR_{25}R_{26}$,
$N(R_{25})SO_2R_{26}$,
$N(R_{25})C(O)_mR_{26}$ (m=1,2),
$N(R_{25})C(O)NR_{26}R_{27}$,
$N(R_{25})SO_2NR_{26}R_{27}$,
$OC(O)R_{24}$,
$OC(O)OR_{24}$,
$SO_2R_{24}$,
$SO_2N(H)C(O)R_{24}$,
$SO_2N(H)CO_2R_{24}$ wherein $R_{24}$ is not H,
$C(O)N(H)SO_2NR_{25}R_{26}$,
$C(O)N(H)SO_2R_{24}$,
$OC(O)NR_{25}R_{26}$,
$NR_{28}—C(=NR_{29})R_{30}$,
$NR_{28}—C(=NR_{29})OR_{24}$,
$NR_{28}—C(=NR_{29})NR_3OR_{31}$,
$C(=NR_{28})NR_{29}R_{30}$,
$OC(=NR_{28})R_{29}$,
$OC(=NR_{28})NR_{29}R_{30}$,
$C(=NR_{28})OR_{24}$, $R_{24}$ is selected from unsubstituted alkenyl, unsubstituted alkynyl, unsubstituted cycloalkyl, unsubstituted aryl, unsubstituted heterocyclo, $R_{25}$, $R_{26}$ and $R_{27}$ are the same or different and are independently selected from unsubstituted alkyl, unsubstituted alkenyl, unsubstituted alkynyl, unsubstituted cycloalkyl, unsubstituted aryl, unsubstituted heterocyclo, or $R_{25}$ and $R_{26}$ or $R_{25}$ and $R_{27}$ or $R_{26}$ and $R_{27}$ may be joined by an alkylene or alkenylene chain to form a 5-8 membered unsubstituted heterocyclo ring, and $R_{28}$, $R_{29}$, $R_{30}$, $R_{31}$ are the same or different and are independently selected from nitro, cyano, unsubstituted alkyl, unsubstituted alkenyl, unsubstituted alkynyl, unsubstituted cycloalkyl, unsubstituted aryl, unsubstituted heterocyclo, or $R_{28}$ and $R_{29}$, or $R_{28}$ and $R_{30}$ or $R_{28}$ and $R_{31}$ or $R_{29}$ and $R_{30}$ or $R_{29}$ and $R_{31}$ or $R_{30}$ and $R_{31}$ may be joined by an alkylene chain to form a 5- to 8-membered unsubstituted heterocyclo ring.

Preferred "alkyl substituents" include the preferred "aryl substituents" set out hereinafter.

Unless otherwise indicated, the term "cycloalkyl" as employed herein alone or as part of another group includes saturated or partially unsaturated (i.e. containing one or more carbon-carbon double bonds) cyclic hydrocarbon groups containing 1 to 3 rings, containing a total of 3 to 20 carbons forming the ring(s), preferably 3 to 10 carbons, forming the ring. Polycyclic systems may contain fused or bridged rings or both. In addition, the cycloalkyl group may be fused to 1 or 2 aryl rings. Examples include cyclopropyl, cyclobutyl, cyclopentyl, cyclohexyl, cycloheptyl, cyclooctyl, cyclodecyl and cyclododecyl, cyclohexenyl,

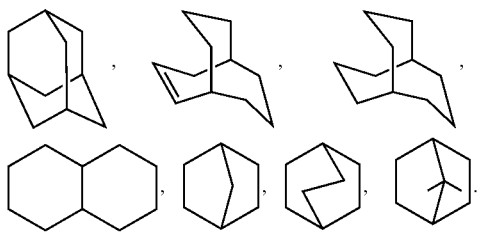

Cycloalkyl groups may be substituted with 1 or more 'cycloalkyl substituents' which may be the same or different at each occurrence. These substituents may occur at any place in any combination that provides a stable compound. These substituents may be any of the substituents for alkyl set out above.

The term "alkanoyl" as used herein alone or as part of another group refers to alkyl linked to a carbonyl group.

Unless otherwise indicated, the term "alkenyl" as used herein by itself or as part of another group refers to straight or branched chain radicals of 2 to 20 carbons, preferably 2 to 12 carbons, and more preferably 1 to 8 such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Lower alkenyl refers to such groups containing 1-6 carbon atoms. Alkenyl groups may be optionally substituted with 1 or more 'alkenyl substituents' which may be the same or different at each occurrence. These substituents may occur at any place in any combination that provides a stable compound. These substituents may be any of those set out for substituents for alkyl as defined above.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Lower alkynyl refers to such groups containing 1-6 carbon atoms. Alkynyl groups may be optionally substituted with 1 or more 'alkynyl substituents' which may be the same or different at each occurrence. These substituents may occur at any place in any combination that provides a stable compound. These substituents may be any of the substituents for alkyl as set out above.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring.

Aryl groups may be optionally substituted through available carbon atoms with 1, or more "aryl substituents" which may be the same or different at each occurrence. These substituents may occur at any place in any combination that provides a stable compound. These substituents may be any of the substituents set out for alkyl as defined above. Preferred aryl substituents include halo, alkyl, haloalkyl, alkoxy, haloalkoxy, alkenyl, $CF_3$, $CF_3O$, alkynyl, cycloalkylalkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl substituents mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the substituents for alkyl set out herein.

Unless otherwise indicated, the term "lower alkoxy", "alkoxy", "aryloxy", "aralkoxy" or "heterocycloalkoxy" as employed herein alone or as part of another group includes any of the above alkyl, aralkyl, aryl, or heterocyclo groups linked to an oxygen atom.

Unless otherwise indicated, the term "acyl" as employed herein by itself or part of another group, as defined herein, refers to an organic radical linked to a carbonyl

group; examples of acyl groups include any of the $R_1$ groups attached to a carbonyl, such as alkanoyl, alkenoyl, aroyl, aralkanoyl, heteroaroyl, cycloalkanoyl, heterocycloalkanoyl and the like.

Unless otherwise indicated, the term "heterocyclo" as used herein alone or as part of another group refers to a monocyclic or multicyclic ring system wherein one or more of the ring atoms are elements other than carbon. Preferred systems have 1 to 4 hetero atoms independently selected from N,O or S. The ring system may be unsaturated, partially saturated, fully saturated or aromatic and thus includes heteroaryl and cycloheteroalkyl rings. Heterocyclo groups containing more than one ring may be fused or bridged. Heteroatoms may be optionally oxidized. Attachment may be through any available atom in the ring system. Heterocyclo groups may be optionally substituted with 1 or more 'heterocyclo substituents' which may be the same or different at each occurrence. These substituents may occur at any place in any combination that provides a stable compound. These substituents may be any of the substituents for alkyl as set out above.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

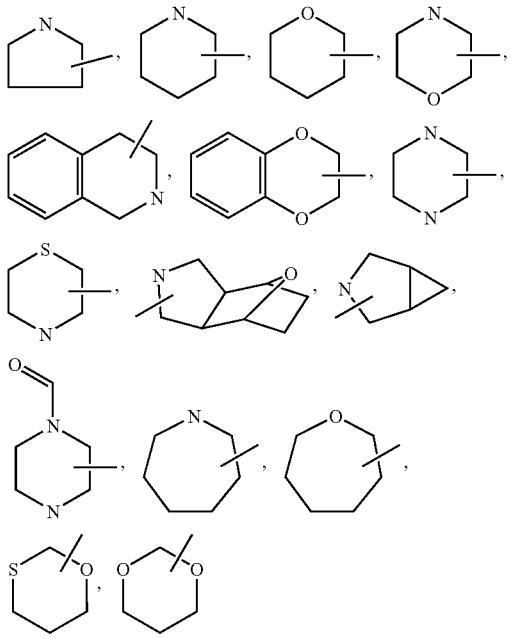

and the like. The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents for alkyl or aryl set out above. Examples of heteroaryl groups include the following:

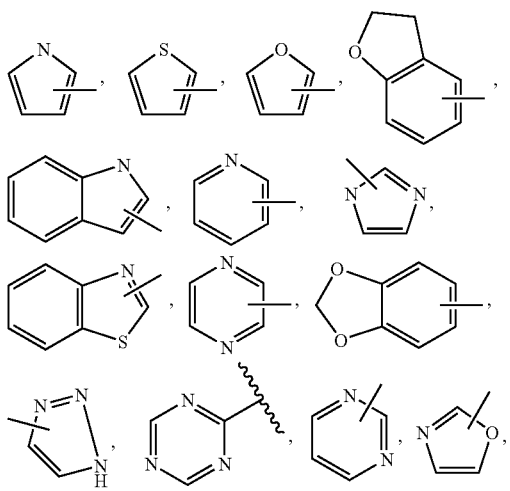

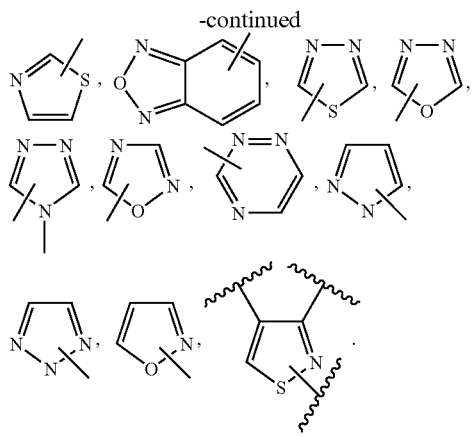

and the like.

As defined above, alkyl, alkenyl, alkynyl, cycloalkyl, and heterocyclo groups may be attached through one or more single bonds to one or more attachment atoms. In addition, these groups may be attached by double bonds to attachment atoms, and these groups may be referred to as 'alkylidene', 'alkenylidene', 'alkynylidene', 'cycloalkylidene' or 'heterocyclidene' groups. Examples include methylidene (=CH2), ethylidene (=CHCH3), ethenylidene (=C=CH2), cyclohexylidene

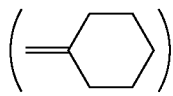

and 2-pyranylidene

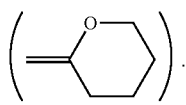.

These groups may be substituted as described above for alkyl, alkenyl, alkynyl, cycloalkyl, and heterocyclo.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of the present invention can have asymmetric centers at certain of the nitrogen or sulfur atoms. Consequently, these isomers or mixtures thereof are part of the present invention.

The compounds of the present invention may also display other instances or chirality, such as atropoisomerism. Thus, these isomers or mixtures thereof are part of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. In addition, prodrug esters which are known in the art for carboxylic and phosphorus acid esters such as methyl, ethyl, benzyl and the like.

Examples of such prodrug esters include $CH_3CO_2CH_2—$, $CH_3CO_2CH_2—CH(CH_3)_2$, $t-C_4H_9CO_2CH_2—$, or $C_2H_5OCOCH_2—$.

Other examples of suitable prodrug esters include

[structures shown]

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

The various novel intermediates a) through n) as set out herein may be prepared as described below.

In accordance with the present invention, a process for preparing novel aldehyde intermediate of the structure 10 is provided

[structure 10]

which includes the steps of reacting compound 8

[structure 8]

wherein $R_1$ and $R_2$ are as defined above, and R and R' are the same or different and are independently selected from alkyl, alkenyl, aryl or a silyl group, with a hydride reducing agent to form intermediate 9

[structure 9]

and reacting the resulting intermediate 9 with an oxidizing agent to form intermediate 10. A more detailed discussion of the above process is described with respect to Scheme 1.

In accordance with the present invention a process is provided for preparing novel intermediate of the structure

[structure 51]

wherein R, $R_1$, $R_2$, and $R_8$ are as defined above;
which includes the steps of
1) reacting compound 47 of the structure

[structure 47]

with compound 3 of the structure

[structure 3]

at a reduced temperature in the presence of a base to provide intermediate 48

[structure 48]

2) reacting intermediate 48 with an ammonium salt to provide intermediate 49

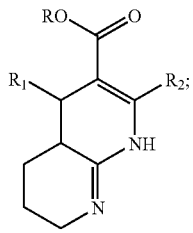

49

3) reacting intermediate 49 with a sulfonylating agent in the presence of a base to provide intermediate 50

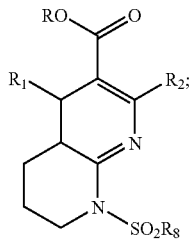

50 where $R_8$ is alkyl, alkenyl, alkynyl, cycloalkyl, aryl or heterocyclo (where the attachment atom in the heterocyclo group is a carbon), and 4) reacting intermediate 50 with an oxidizing agent to form intermediate 51.

A more detailed description of the above process is described with respect to Scheme 17.

In a preferred embodiment, in intermediate 3:
$R_1$ is 4-fluorophenyl,
$R_2$ is isopropyl, and
R is methyl,
and in intermediate 50, $R_8$ is methyl, and in step 1) compound 47 is added to a solution of sec-butyllithium in cyclohexane-THF at about 60° C. or below, and compound 3 is reacted with the above mixture.

In another aspect of the invention, a process is provided for preparing novel aldehyde intermediate of the structure 53.

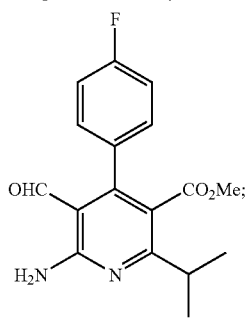

53 which includes the step of treating compound 52

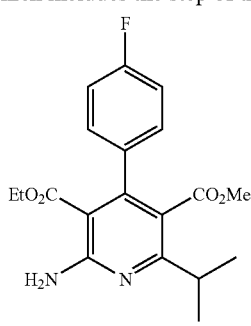

52 with a reducing agent which is sodium bis(2-methoxyethoxy)-aluminum hydride, pyrrolidine and potassium tert-butoxide in methyl tert-butyl ether, at a temperature below 0° C. to provide intermediate 53.

A more detailed description of the above process is described with respect to Scheme 18.

In another embodiment of the invention, a process is provided for preparing novel intermediate of the structure 58.

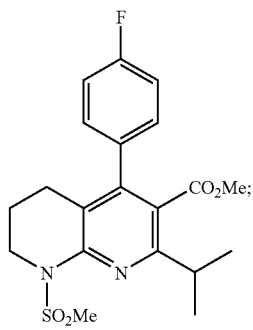

58 which includes the step of treating a compound of the structure 57

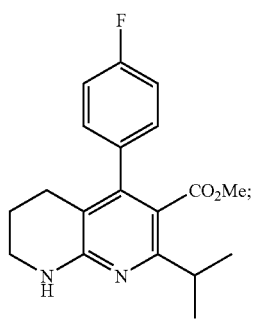

57 with methanesulfonic anhydride in the presence of 3,5-lutidine in toluene and dichloromethane to form intermediate 58.

A more detailed description of the above process is described with respect to Scheme 19.

In yet another embodiment of the invention, a process is provided for preparing novel intermediate of the structure 58

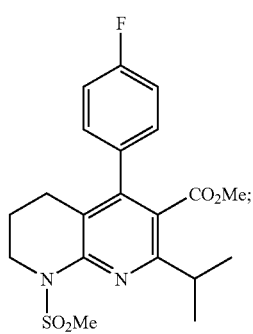

58 which includes the steps of
1) reacting a mixture of lactam 64

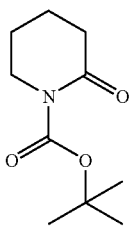

and a base with compound 3

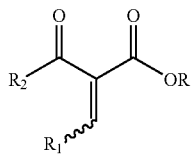

where R is preferably methyl,
R₁ is preferably p-F—C₆H₅ and
R₂ is preferably isopropyl,
at a reduced temperature to form intermediate 65

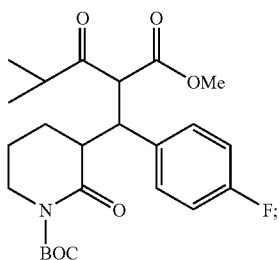

2) reacting intermediate 65 with an acid to provide intermediate 66

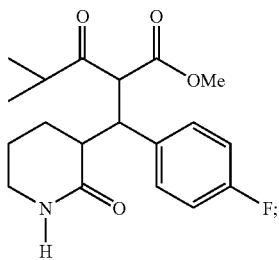

3) reacting intermediate 66 with an activating agent at an elevated temperature, and then treating the resulting reaction product with ammonium acetate to form intermediate 68

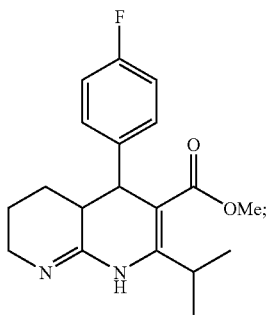

4) reacting intermediate 68 with methanesulfonyl chloride and diisopropylethylamine in ethyl acetate at a temperature below 25° C., and reacting the resulting reaction product with an oxidizing agent to form intermediate 58.

A more detailed description of the above process is described with respect to Scheme 25.

In still another embodiment of the invention, a process is provided for preparing novel intermediate of the structure 68

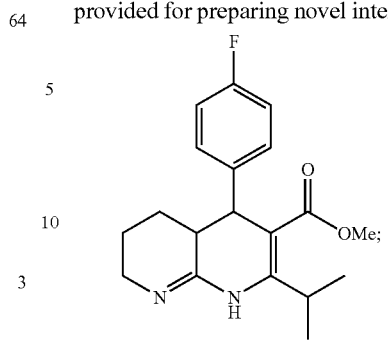

which includes the steps of
1) reacting intermediate 66

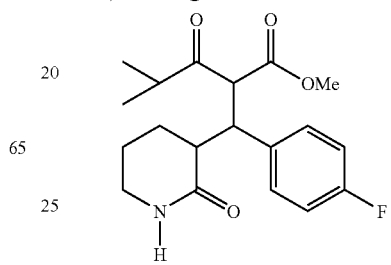

with PCl₅ in dichloroethane at a an elevated temperature, and then with ammonia in methanol at below room temperature; and
2) treating the resulting product 67

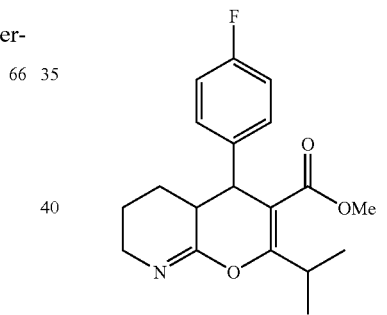

with ammonium acetate in methanol to form intermediate 69

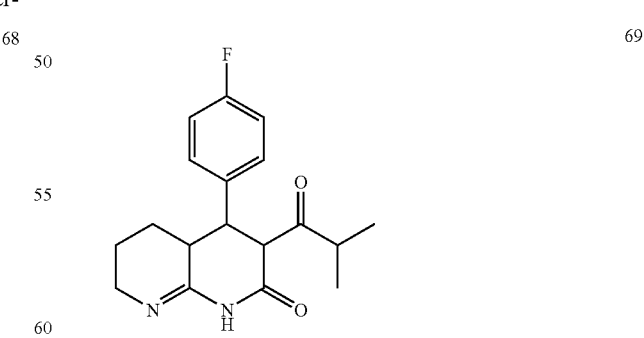

and heating intermediate 69 at a temperature within the range from about 65 to about 70° C. to form intermediate 68.

A more detailed description of the above process is described with respect to Scheme 26.

In yet another aspect of the present invention, a process is provided for preparing novel intermediates of the structure 57

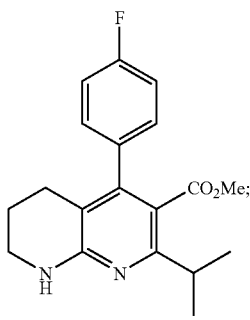

which includes the steps of reacting intermediate 66

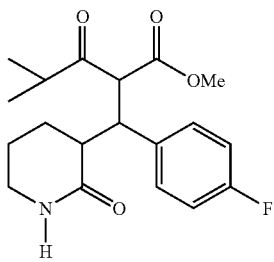

or reacting intermediate 65

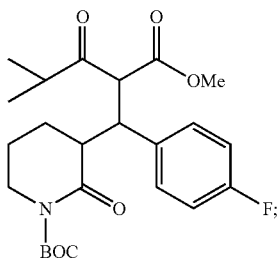

with PCl$_5$ in dichoroethane at a temperature within the range from about 50 to about 75, and 2) treating the reaction mixture wth ammonia in methanol with an oxidizing agent to form intermediate 57.

A more detailed description of the above process is described with respect to Scheme 27.

Compounds of the invention may be prepared by the following processes.

Additional functional groups and substituents as specified for compound I can be easily incorporated into the target molecules using modifications of the methods described. The steps involved to reach the desired target compounds are common organic transformations and are known to those skilled in the art of organic synthesis.

Scheme 1 summarizes the preparation of monocyclic intermediates 8, 9 and 10 which are used to prepare a subset of compounds of formula I or II of the invention.

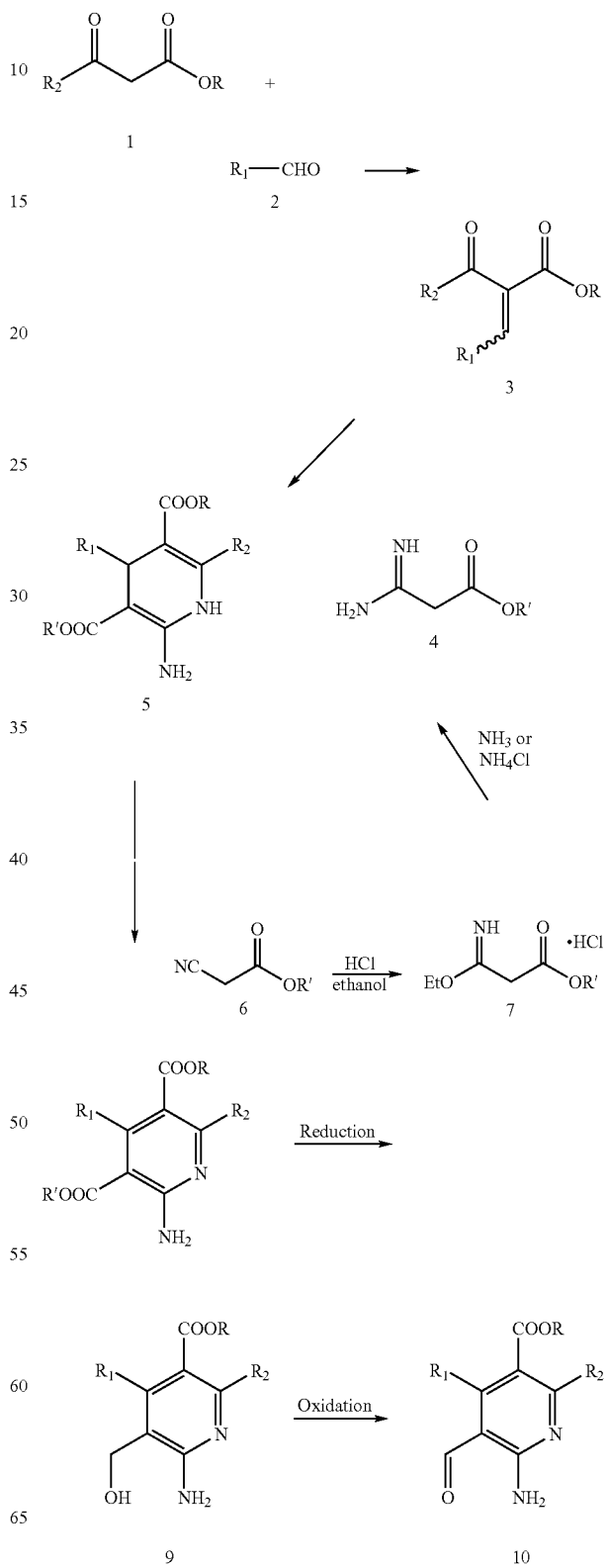

Knovenagel condensation of a 1,3-dicarbonyl compound such as 1 (wherein $R_2$ is defined as for formula I or II) with an aldehyde 2 (wherein $R_1$ is defined as for structure I or II) under standard conditions (for example, catalytic (cat.) amounts of acetic acid, cat. amounts of piperidine, toluene, reflux) provides adduct 3. This adduct is condensed with amidines of type 4 to provide dihydropyridine adducts of type 5. (The position of the double bonds in the ring system are drawn arbitrarily). This condensation can be carried out in an alcoholic solvent (such as ethanol) in the presence of an amine base such as triethylamine. The amidine may be employed in its free base form or as a salt form, such as a hydrochloride salt.

The required amidine 4 is first prepared from cyanoesters of type 6. Cyanoester 6 is first converted into its iminoether hydrochloride salt 7 by the action of HCl in an alcohol solvent. For example, ethanol is used when R' is ethyl. A co-solvent such as heptane may optionally be used. The HCl may be introduced as a gas or may be generated in situ by prior addition of acetyl chloride or phosphoryl chloride to the alcoholic solvent. Iminoether salt 7 or its free base form is reacted with ammonia or an ammonium salt in an alcoholic solvent to form amidine 4.

Subsequently, dihydropyridine 5 is converted to substituted pyridines of type 8 using DDQ or ceric ammonium nitrate. Reduction of compounds of type 8 with RedAl® (sodium bis(methoxyethoxy)aluminum hydride) or a similar hydride reducing agent in THF or other inert organic solvent such as dichloromethane, methyl-tert-butylether or toluene provides alcohols of type 9. The alcohol group in 9 is oxidized with manganese dioxide or other oxidizing agent such as TEMPO/KBr/NaOCl, sodium chlorite, DMSO/oxalyl chloride/Hunig's base or Dess-Martin reagent to provide compounds of type 10.

In this scheme, R and R' may be alkyl (such as methyl, ethyl, isopropyl, t-butyl), substituted alkyl (such as benzyl), alkenyl (such as allyl), aryl (phenyl), silyl (such as t-butyldimethylsilyl, triethylsilyl, t-butyldiphenylsilyl) or another group known to those skilled in the art of organic to be useful as a protecting group for carboxylic acids. Each of R and R' may chosen so as to provide one skilled in the art of organic synthesis the ability to selectively transform or functionalize one of the ester groups in the presence of the other; in the presence of other protecting groups which may be employed to prepare compounds of formula I or II; or in the presence of other functional groups which may be present in compounds of formula I or II or its synthetic precursors. For example, when R is benzyl and R' is methyl, hydrogenation in the presence of a catalyst (Pd/C, for example) converts the COOR ester group to a COOH group leaving the COOMe group unchanged. Transformations of the COOH group into other groups (such as $CH_2OH$ by reduction with borane, conversion to an acid chloride by reaction with oxalyl chloride or thionyl chloride) may then be accomplished. In some of the following schemes, other groups of similar utility are employed for carboxyl groups and/or other functional groups such as amino, hydroxy, carbonyl, amido, and the like. These cases will be recognized by those skilled in the art of organic synthesis.

Scheme 2 outlines the synthesis of advanced intermediate compounds with a fused 5-membered ring which are used to prepare a subset of compounds of formula I or II of the invention.

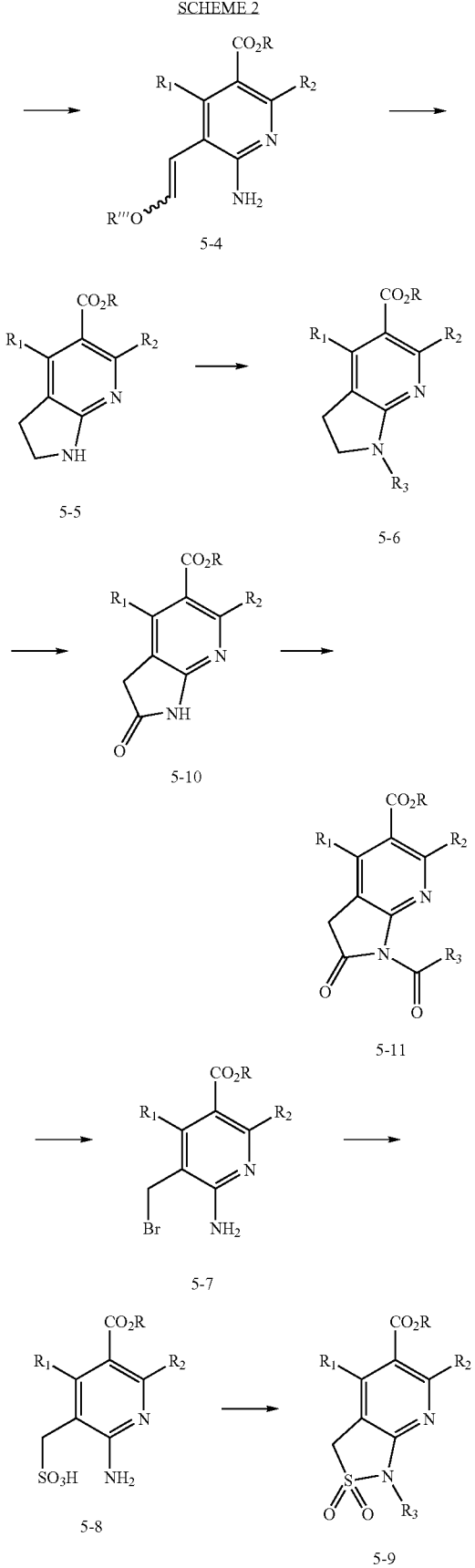

SCHEME 2

A Wittig or similar condensation reaction using (methoxymethyl) or (benzyloxymethyl)triphenylphosphonium bromide or a related reagent and a base such as potassium tert-butoxide provides compounds of type 5-4 from intermediate 10.

Additionally, treatment of 5-4 with an aqueous mineral acid such as HCl (or other acid) in THF provides compounds of type 5-5 after reduction of the intermediate indole with, for example, hydrogen/palladium catalyst, triethylsilane/TFA, or sodium cyanoborohydride/TFA. Compound 5-5 is then converted to 5-6 wherein $R_3$ is defined as for formula I or II or may be an amine protecting group compatible with subsequent transformations. The methods used for the preparation of 5-6 involve reaction of 5-5 with an $R_3$ reagent wherein the nature of $R_3$ would be known to those skilled in the art of organic synthesis. For example, an alkylation reaction ($R_3$—I, base) may be used when $R_3$ is alkyl; acylation or sulfonylation ($R_8$COCl or $R_8$SO$_2$Cl, base) when $R_3$ is acyl or sulfonyl.

Compound 5-4 may be converted by a multistep procedure into compound 5-10: the amino group is protected; the enol ether is treated with a mineral acid and the resultant aldehyde is oxidized to a carboxylic acid; the amine is deprotected; and the resultant amino acid is cyclized. These common transformations may be easily accomplished by those skilled in the art of organic synthesis using common reagents and procedures. Finally, 5-10 may be converted using ordinary procedures into 5-11 such as described with respect to preparation of 5-6 from 5-5.

Intermediate 9 may be used to prepare other advanced intermediates. Treatment of 9 with aqueous HBr provides a compound 5-7 as the hydrobromide salt. Treatment of 5-7 with sodium sulfite provides 5-8 which can be cyclized and functionalized with an $R_3$ reagent such as set out above to provide 5-9.

The advanced intermediates in Scheme 2 can be transformed to the compounds of formula I or II of the invention by using the methodology outlined in Schemes 3 and 4.

-continued

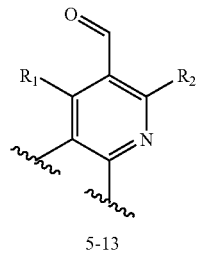

5-13

Compounds 5-6, 5-9, and 5-11 are reduced to provide a benzylic alcohol, 5-12. The transformation may be accomplished by direct reduction with a reducing agent such as Red-Al®, LAH, or DIBAL or the like or by a multistep procedure.

For example, the ester group may be converted to a carboxylic acid by hydrolysis (if R is alkyl), hydrogenolysis (if R is benzyl) or by treatment with a palladium catalyst (if R is allyl). The acid may be reduced directly to provide compounds of type 5-12 or, using common procedures, it may be converted to an acid chloride or mixed anhydride which provide compounds of type 5-12 by reduction. Additional multi-step procedures may be employed, the chemistry of which is consistent with the presence and choice of other protecting groups and/or functional groups.

Oxidation of 5-12 using Dess-Martin reagent, TEMPO/KBr/NaOCl, sodium chlorite, DMSO/oxalyl chloride/Hunig's base provides aldehydes of type 5-13.

SCHEME 3

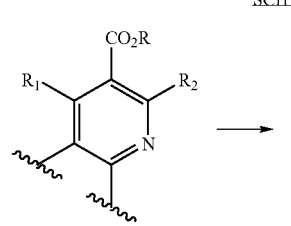

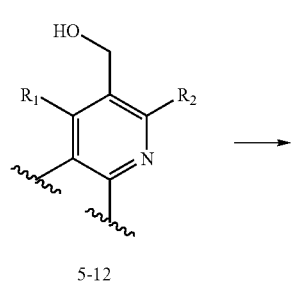

5-12

SCHEME 4

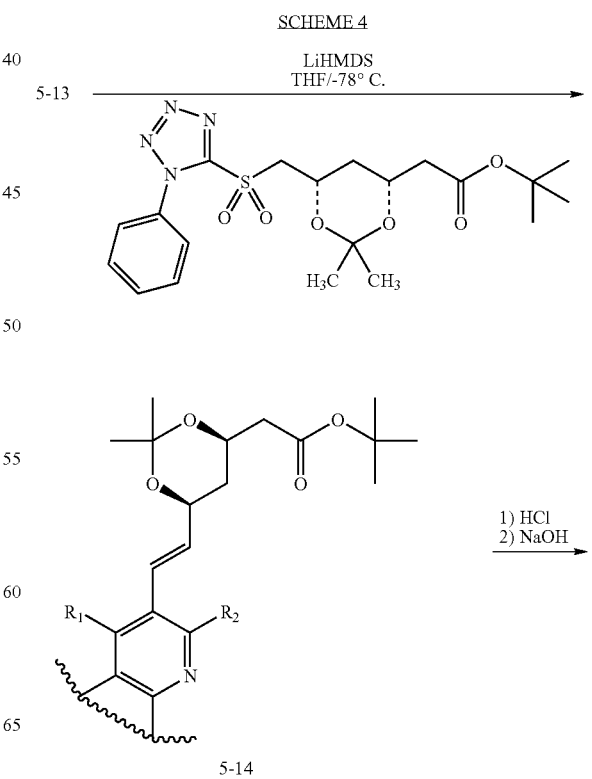

5-14

-continued

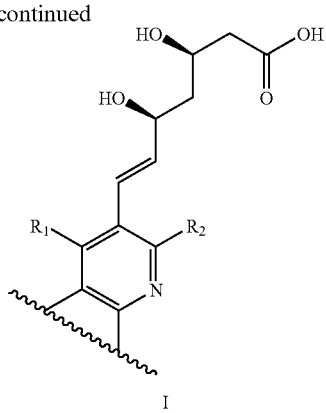

I

Compounds of type 5-13 are condensed with the known sulfone shown in the scheme in the presence of LiHMDS or similar base to provide compounds of type 5-14 which in turn are treated with an acid, such as aq HCl and base, such as sodium hydroxide to provide compounds of formula I or II of the invention.

Catalytic reduction of compounds of type 5-14 prior to acid and base treatment provide a subset of compounds of formula I in which C⁓⁓C is reduced.

Another subset of compounds of formula I or II of the invention contain a fused six-membered ring. These may be prepared as shown in the following schemes.

SCHEME 5

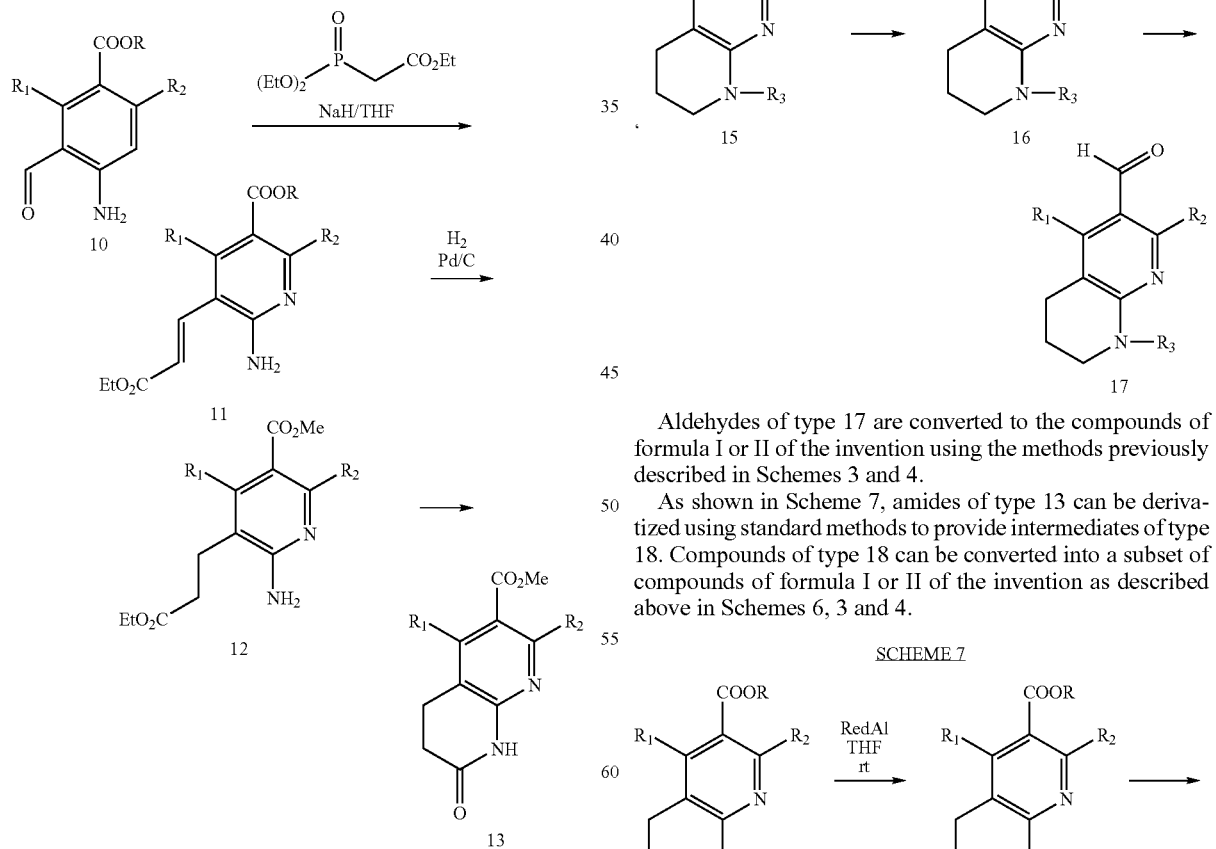

As seen in Scheme 5, monocyclic intermediates of type 10 are condensed with triethyl phosphonoacetate or a similar reagent in the presence of sodium hydride or a similar base to provide ester 11.

Ester 11 is reduced with hydrogen in the presence of palladium/carbon or a similar catalyst to provide 12. Aminoester 12 is then cyclized by heating in toluene, optionally in the presence of an acid catalyst (e.g. p-toluenesulfonic acid), to provide bicycle 13.

As shown in Scheme 6, amide 13 is reduced with RedAl® or a related reagent to provide aminopyridine 14. Reaction of 14 with an appropriate acylating, alkylating, sulfonylating reagent using standard methods provides compounds of type 15. Conversion of these compounds to aldehydes 17 can be accomplished using a two-step reduction oxidation procedure which uses DIBAL or a similar reagent to effect the reduction to 16 and TEMPO/NaOCl/KBr or an alternative oxidizing agent to effect oxidation to the aldehyde 17.

SCHEME 6

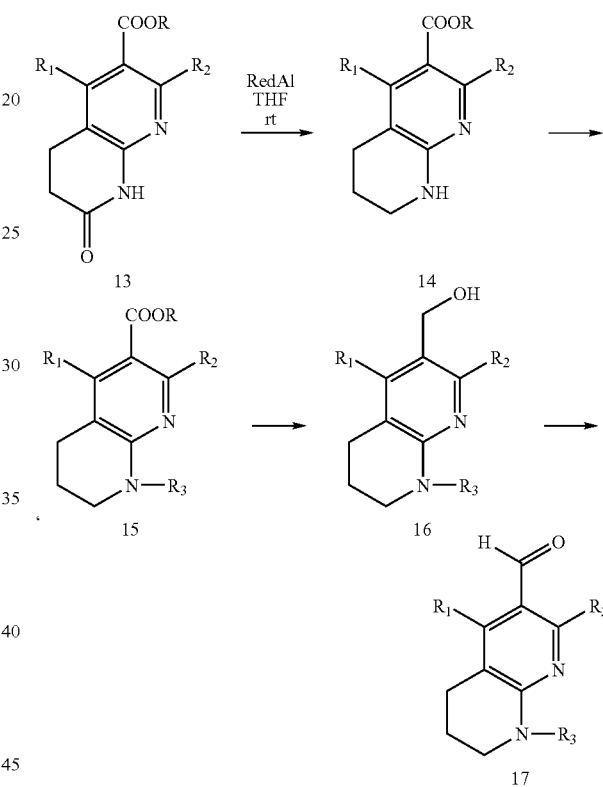

Aldehydes of type 17 are converted to the compounds of formula I or II of the invention using the methods previously described in Schemes 3 and 4.

As shown in Scheme 7, amides of type 13 can be derivatized using standard methods to provide intermediates of type 18. Compounds of type 18 can be converted into a subset of compounds of formula I or II of the invention as described above in Schemes 6, 3 and 4.

SCHEME 7

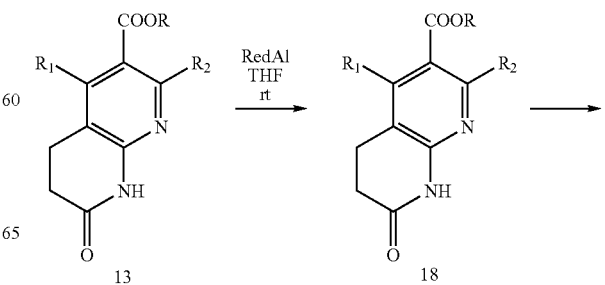

-continued

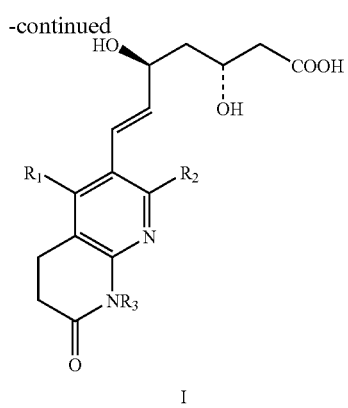

I

Another subset of the compounds of formula I or II of the invention can be prepared using the chemistry outlined in Scheme 8.

Another subset of the compounds of formula I or II of the invention may be prepared using the methods outlined in Scheme 9.

SCHEME 9

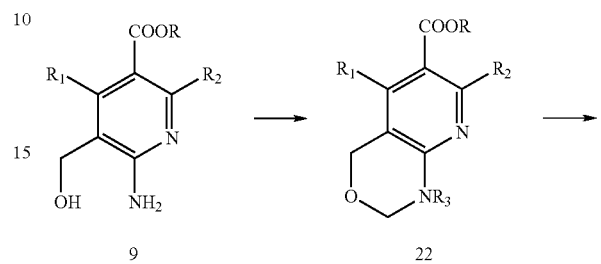

SCHEME 8

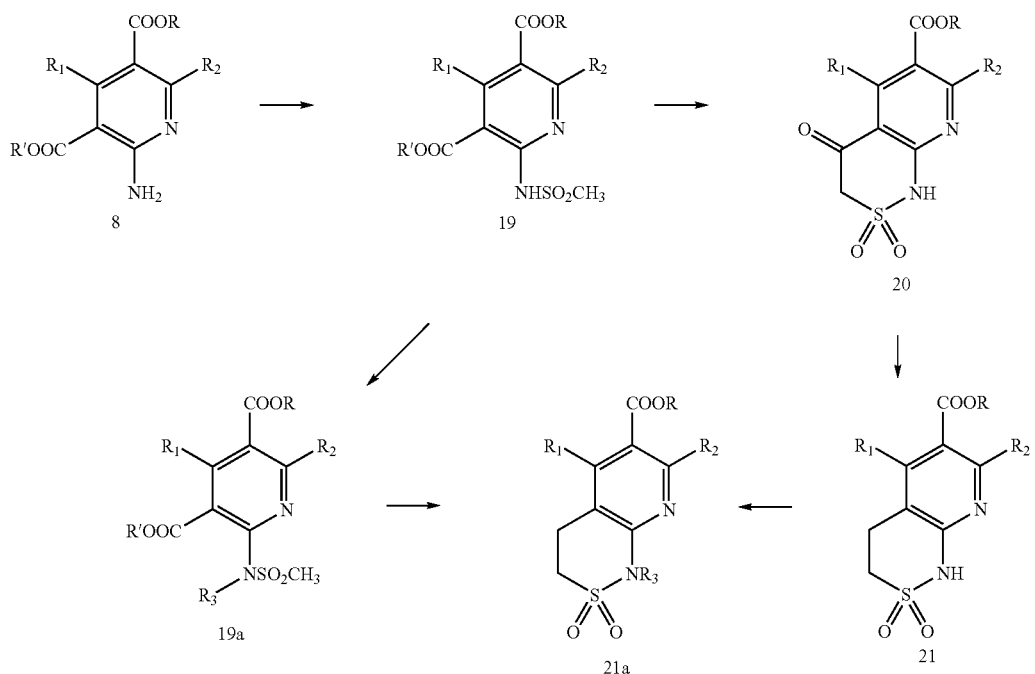

Aminodiester 8 is mesylated to provide intermediate 19 which is treated with a base such as sodium hydride to provide intermediate 20. This in turn is reduced (for example, sodium borohydride or the like), mesylated (for example, methanesulfonyl chloride/pyridine), treated with a base to effect elimination and then hydrogenated in the presence of a palladium or similar catalyst to provide an intermediate of type 21 which is treated with an $R_3$ reagent as described with respect to Scheme 2 to form 21a.

Alternatively, 19 may be treated with an $R_3$ reagent as described with respect to Scheme 2 to form 19a which is treated with base such as sodium hydride to form 21a.

-continued

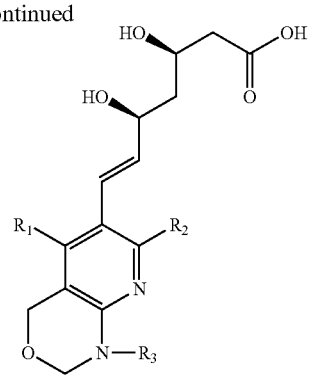

Condensation of aminoalcohol 9 with an aldehyde, e.g. formaldehyde, or ketone in the presence of an acid catalyst provides intermediates of type 22 which can be converted to the title compounds using the methods described above in Schemes 3 and 4.

Another subset of the compounds of formula I or II of the invention can be prepared using intermediate 20 as shown in Scheme 10.

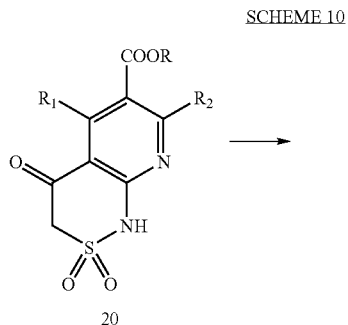

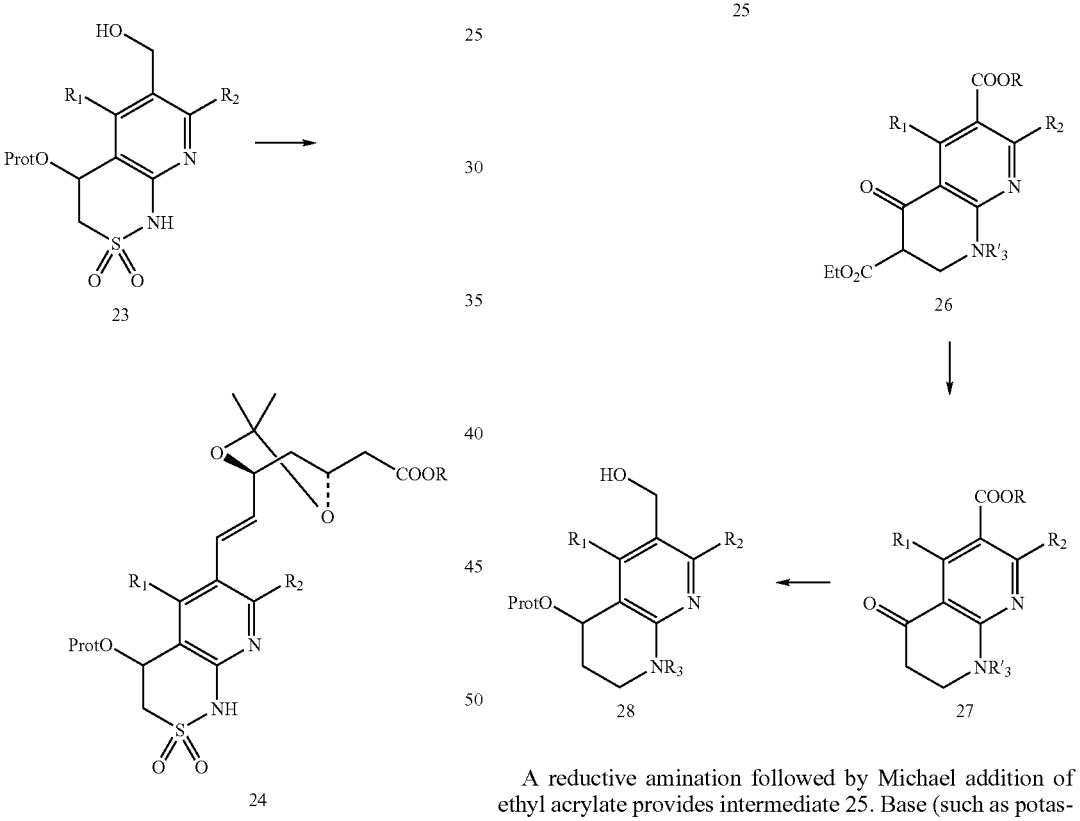

Intermediate 20 is subjected to reduction using LAH, DIBAL, RedAl® or a similar reagent followed by selective protection of the less hindered alcohol group with a silyl protecting group such as t-butyldimethylsilyl or the like. Transformation of this intermediate (23) as described above provides a differentially protected intermediate 24 which can be desilylated, oxidized and then fully deprotected to provide the compounds of formula I or II.

Another subset of the compounds of formula I or II of the invention can be prepared from intermediates of type 8 as shown in Scheme 11.

A reductive amination followed by Michael addition of ethyl acrylate provides intermediate 25. Base (such as potassium tert-butoxide) induced cyclization provides intermediate 26. Decarboxylation (for example, DMSO/NaCl/heat, NaOH then heat) and functional group manipulation as previously described provide intermediates 27 and 28 in turn. Final conversion of 28 to the compounds of the invention is accomplished as previously described in Scheme 4. R'$_3$ may be as defined for R$_3$ or may be a protecting group known to those skilled in the art which can be removed using standard methods (for example R'$_3$ may be CH$_2$Ph and may be removed by H$_2$/Pd—C). When R'$_3$ is a protecting group, it is removed as a step or steps in the preparation of 28 from 27. In these cases, R$_3$ is introduced using an R$_3$ reagent as set forth previously.

Another subset of the compounds of formula I or II of the invention can be prepared as described in Scheme 12. Compounds of type 29, which are known in the literature, may be condensed with an enone 29a to provide compounds of type 30. These latter compounds may also be prepared by chemistry known in the literature from compounds of type 31 which are also known in the literature. The preparation of compounds of type 31 from compounds of type 8 has been also reported in the literature.

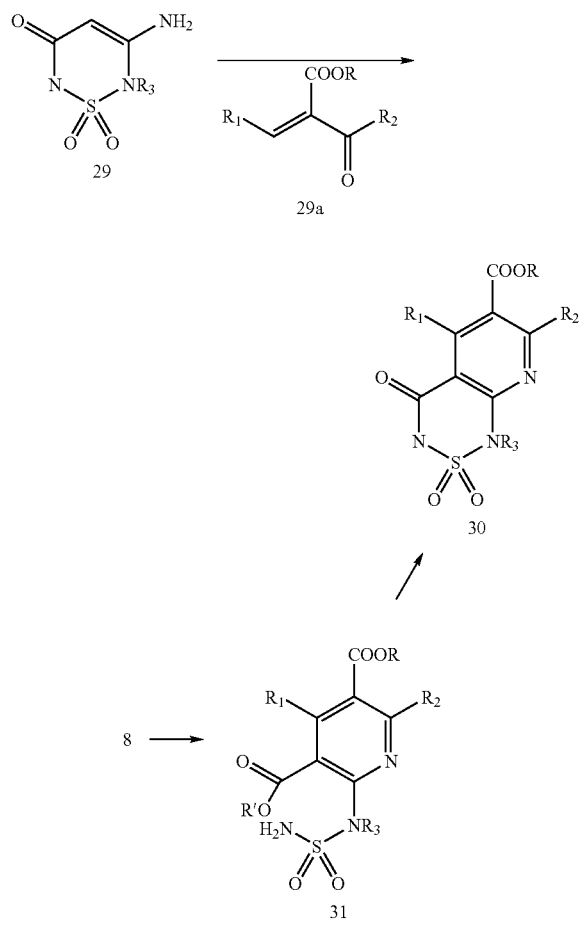

Another subset of compounds of formula I or II of the invention contain a 7-membered ring fused to the central pyridine ring. These may be prepared as described in the following schemes.

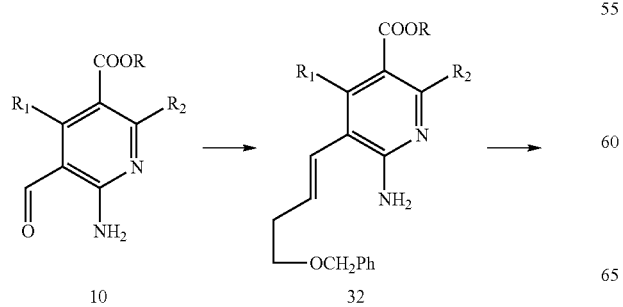

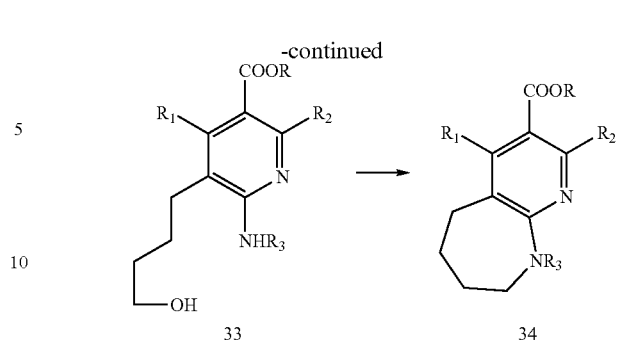

As shown in Scheme 13, intermediates of type 10 are converted to intermediates of type 32 by treatment with (3-(benzyloxy)propyl)triphenylphosphonium bromide or a related reagent and a base such as lithium hexamethyldisilazide. Hygrogenation of intermediate 32 in the presence of a palladium or related catalyst followed by reaction with a reagent appropriate for the introduction of the $R_3$ group (as described above) affords intermediates of type 33. Reaction of compounds of type 33 with an activating reagent such as mesyl chloride in the presence of an amine base followed by treatment with a base (such as potassium carbonate or the like) in a solvent such as DMF provides compounds of type 34. The conversion of compounds of type 34 to the compounds of formula I or II of the invention may be accomplished using procedures set out above such as in Schemes 3 and 4.

Another subset of compounds of formula I or II of the invention are prepared from intermediate 33 as shown in Scheme 14.

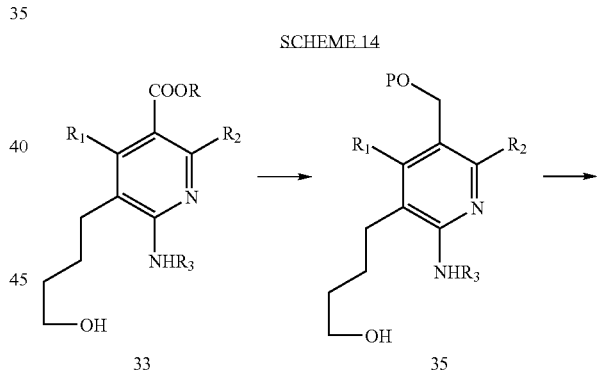

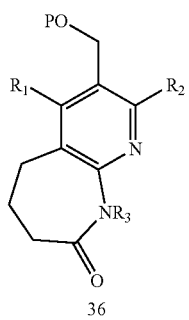

The hydroxy group of compounds of type 33 is protected (such as with a t-butyldimethylsilyl group), and the ester is reduced with LAH, DIBAL-H, or the like and the resultant carbinol is protected (for example, as an acetate, benzoate or more hindered silyl ether). The first alcohol protecting group is removed using common procedures to provide 35, the resultant alcohol is oxidized to the corresponding carboxylic acid and finally treatment with an amide forming reagent (DCC, BOP, WSC, etc) affords compounds of type 36. These compounds may then be converted to compounds of formula I or II of the invention as set out previously such as in Schemes 3 and 4 after removal of the remaining alcohol protecting group.

As shown in Scheme 15 a further subset of compounds of formula I or II of the invention may be prepared from intermediate 5-4.

Reduction of 39 with a selective reducing agent such as sodium borohydride followed by treatment with mesyl chloride/amine base and hydrogenation provides intermediates of type 40.

Reduction of 39 with LAH or a related reagent followed by protection of the unhindered alcohol (i.e., P') and subsequent protection of the hindered alcohol (i.e., P) affords an intermediate 41.

Both compounds 40 and 41 may be converted into compounds of formula I or II of the invention by methods previously described such as in Schemes 3 and 4.

Intermediate 8 may also be used to prepare other subsets of compounds of formula I or II of the invention as outlined in Scheme 16.

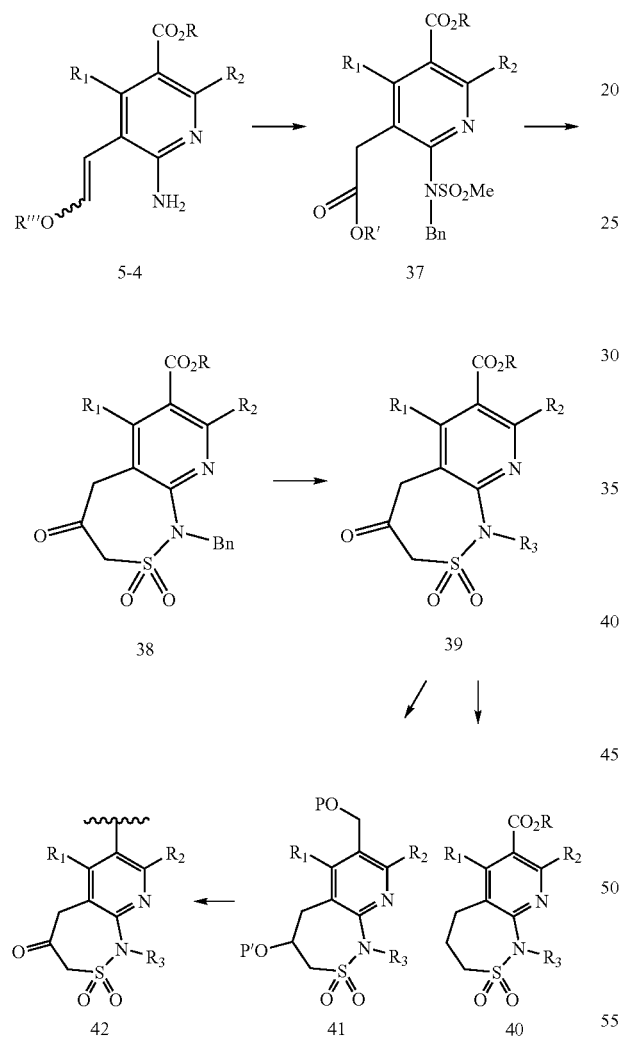

The amine group of 5-4 is mesylated (methanesulfonyl chloride/amine base) and benzylated (benzyl bromide, carbonate base). The resultant intermediate is then treated with a mineral acid, an oxidant and then esterified (diazomethane or methyl iodide/carbonate base) to provide an intermediate of type 37. Treatment of 37 with a base such as sodium hydride affords intermediate 38. The benzyl group of intermediate 38 is removed by hydrogenation in the presence of a palladium or related catalyst and the $R_3$ group is added as previously described to form 39.

Intermediates of type 8 are converted into compounds of type 43 by diazotization/fluorination (sodium nitrite/flouroboric acid/THF/water). Reaction of 43 with aminoethanol affords compounds of type 44 which are reduced with a hydride reagent such as LAH or RedAl® to afford compounds of type 45. Treatment of compounds of type 45 with an acid catalyst, such as p-toluenesulfonic acid or HCl afford cyclized intermediates of type 46. Compounds of type 46 can be transformed into compounds of formula I or II of the invention as described above such as in Schemes 3 and 4.

Preferred compounds of the invention of formula II wherein $R_3$=$SO_2R_8$ and U=bond and V, W and Y=$CH_2$ can be prepared using the preferred methods shown in Scheme 17.

SCHEME 17

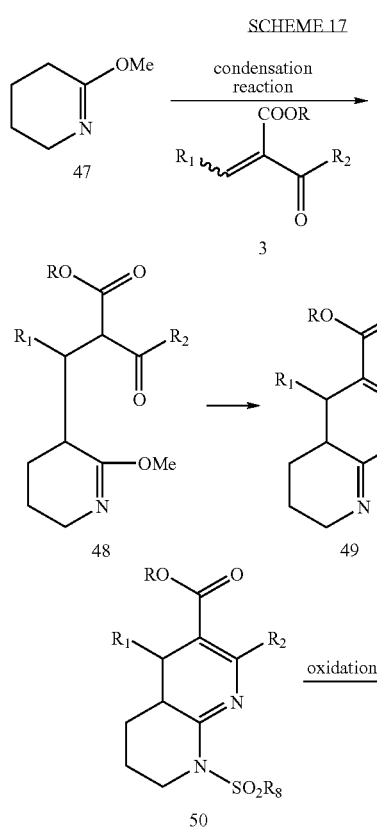

Known compound 47 is condensed with compound 3 employing a molar ratio of 3:47 within the range from about 1.2:1 and about 1.5:1, at low temperature such as from about −78° C. to about −70° C., preferably −78° C. to provide intermediate 48. A base such as lithium diisopropylamide or n-butyllithium or sec-butyllithium is used and the solvent may be THF, diethylether, or the like. Intermediate 48 is reacted with an ammonium salt such as ammonium chloride or ammonium acetate, employing a molar ratio of ammonium salt:48 within the range from about 1.25:1 to about 1.5:1, in a solvent such as methanol or ethanol to provide intermediate 49 (in which the position of the double bonds is drawn arbitrarily). Intermediate 49 is converted to compound 51 by a multistep procedure wherein 49 is first reacted with a sulfonylating agent (such as methanesulfonyl chloride when $R_3$ is methyl) in the presence of a base such as diisopropylethylamine (DIPEA), preferably triethylamine, to provide 50, employing a molar ratio of sulfonating agent:49 with the range from about 2:1 to about 2.5:1. Subsequent treatment of 50 mixture with DDQ or an alternate oxidizing reagent such as ceric ammonium nitrate provides intermediate 51. Intermediate 51 can be converted to compounds of formula II wherein $R_3$=$SO_2R_8$ and U=bond and V, W and Y=$CH_2$ using the methods described in Schemes 3 and 4.

A preferred method for the conversion of intermediate 47 to 51 shown in Scheme 17 (wherein $R_1$=4-fluorophenyl and $R_2$=isopropyl, R=methyl and $R_8$=methanesulfonyl) involves, first, adding 47 to a solution of 1 equivalent of sec-butyl lithium in cyclohexane-THF at around −60° C. or below. Reagent 3 (wherein $R_1$=4-fluorophenyl and $R_2$=isopropyl and R=methyl) is added to the mixture at the same temperature. After an ammonium chloride quench and extractive workup, ammonium chloride is added and the solvent is exchanged for methanol. The resultant mixture is stirred at or around 52° C. The solvent is exchanged for ethyl acetate. After filtration, the solution is treated with diisopropylethylamine at around −20° C. and then with methanesulfonyl chloride at or below 0° C. After an extractive workup the solution is oxidized with ceric ammonium nitrate in water at around 0° C. to 5° C. An extractive workup and crystallization provides compound 51 wherein wherein $R_1$=4-fluorophenyl and $R_2$=isopropyl, R=methyl and $R_8$=methanesulfonyl.

Other preferred procedures for the preparation of compounds of the invention of formula II wherein $R_1$=4-fluorophenyl, $R_2$=isopropyl, $R_3$=$SO_2CH_3$, U=bond, and V, W and Y=$CH_2$ is shown in Schemes 18-27.

Scheme 18

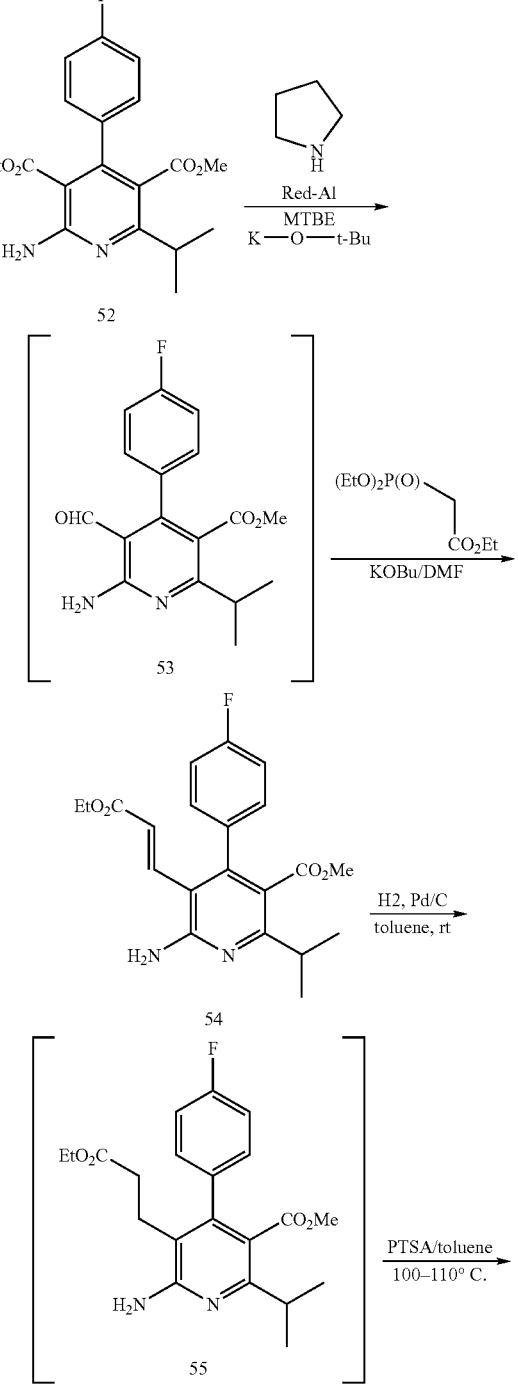

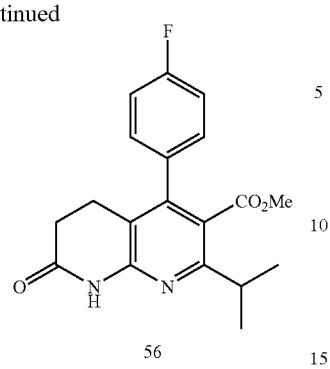

56

Compound 52 is reduced with Red-Al®/pyrrolidine/potassium tert-butoxide in MTBE below 0° C., preferably for about −5° C. to about −25° C., more preferably about −15° C., to provide compound 53. Compound 53 is then converted into compound 54 using triethylphosphonoacetate and potassium tert-butoxide in DMF below room temperature, preferably at 0-5° C. Compound 54 is then reduced to provide compound 55 using palladium on carbon as a catalyst, toluene as solvent and sparging hydrogen into the reaction mixture. A toluene solution of intermediate 55 is obtained by filtration of the reaction mixture through Celite® and this solution is mixed with p-toluenesulfonic acid and heated at 100-110° C. to provide compound 56.

As shown in Scheme 19, compound 56 is reduced with an excess of Red-Al® in toluene and THF at around 5° C. using a potassium sodium tartrate quench to provide compound 57. Compound 57 is then converted to intermediate 58 using methanesulfonic anhydride employing a molar ratio of anhydride:58 within the range from about 2:1 to about 2.5:1, in the presence of 3,5-lutidine in toluene and dichloromethane.

An additional preferred procedure for the transformation described in Scheme 19 is one in which the two steps are telescoped and intermediate 57 is not isolated. This is accomplished by distilling the residual THF from the organic layer containing intermediate 57 and then using the resultant toluene solution in the second step.

Scheme 19

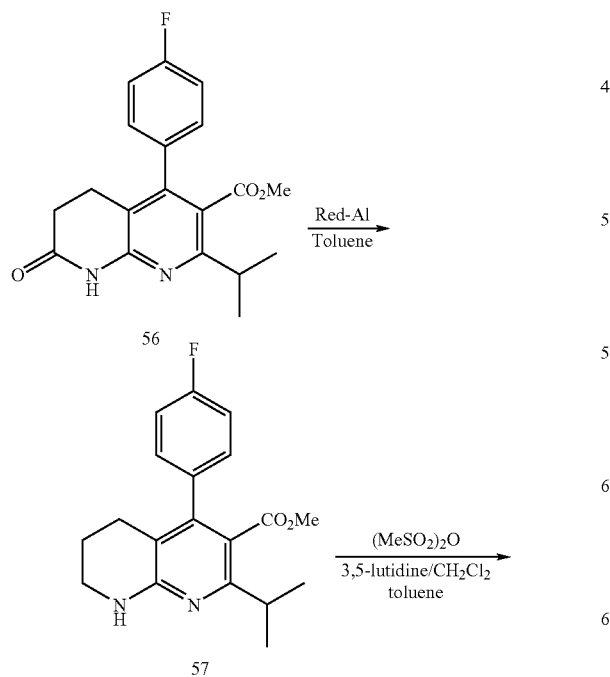

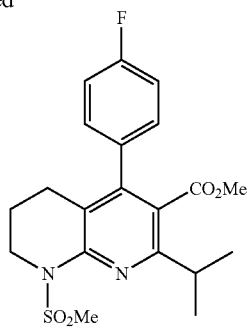

58

In continuation of the preferred procedures, as shown in Scheme 20, intermediate 58 is reduced with DIBAL in dichloromethane at around or below −10° C. to produce compound 59.

Without isolation, compound 59 is converted to aldehyde 60 using sodium hypochlorite/TEMPO/KBr at or around 4° C.

Scheme 20

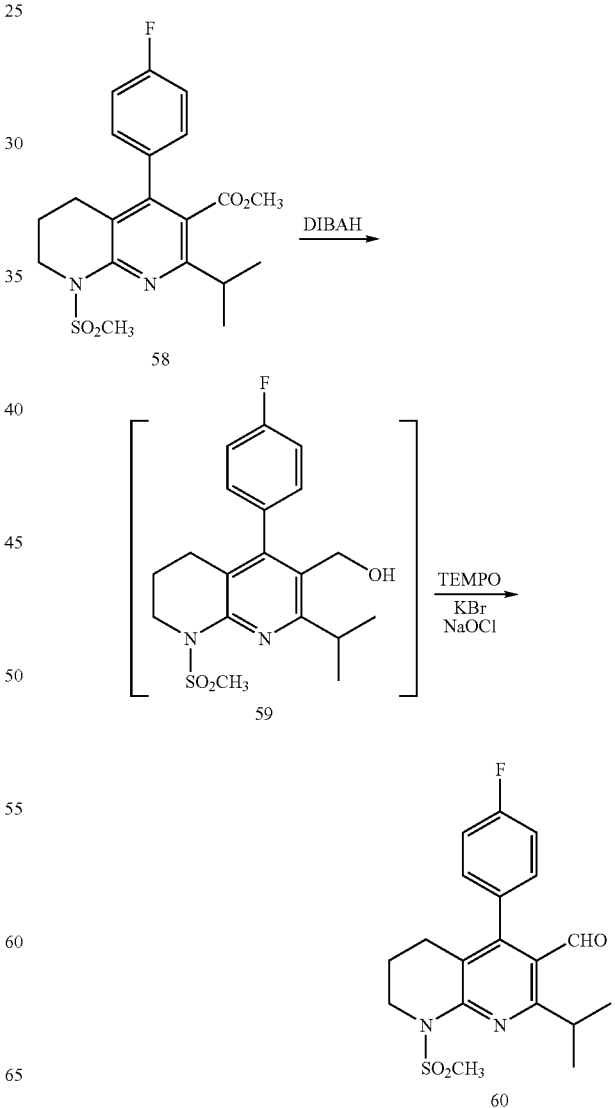

A preferred procedure for converting intermediate 60 to intermediate 62 is shown in Scheme 21. A 1:1 molar mixture of 60 and the known sulfone 61 is treated with 1 molar equivalent of lithium hexamethyldisilazide at or around −78° C. After the reaction is complete, an ammonium chloride quench, and an extractive workup provides 62 which is recrystallized, preferably from ethanol-water or, alternatively, from ethanol-hexanes.

Scheme 21

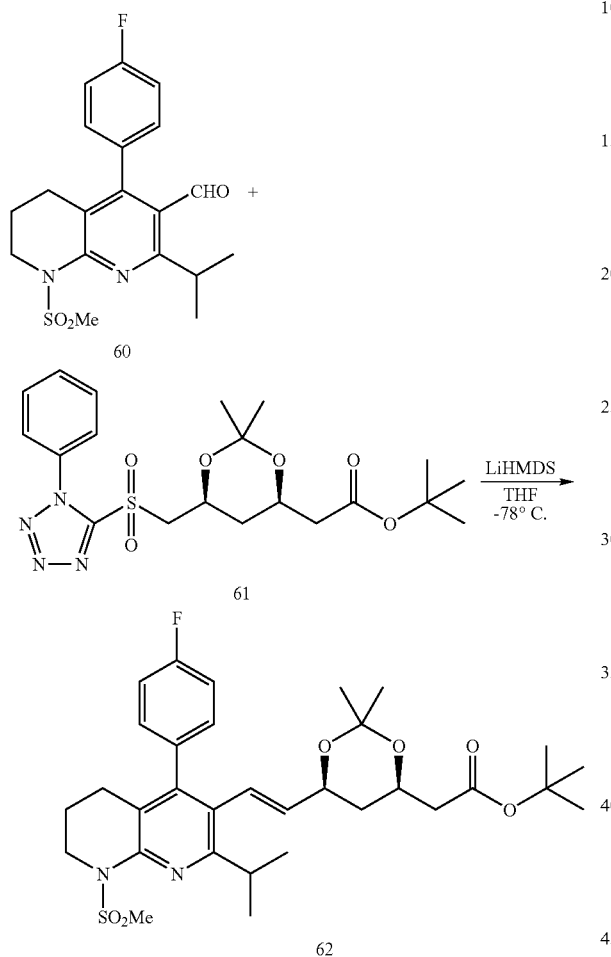

An additional preferred procedure is shown in Scheme 22. Intermediate 62 is treated with an aqueous mineral acid, preferably sulfuric acid, in THF at or around 50° C. to provide 63. This intermediate is useful in that it may be isolated and purified, for example, by recrystallization from ethanol-water.

Scheme 22

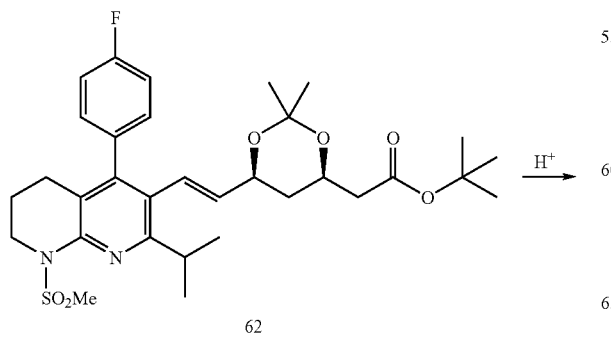

-continued

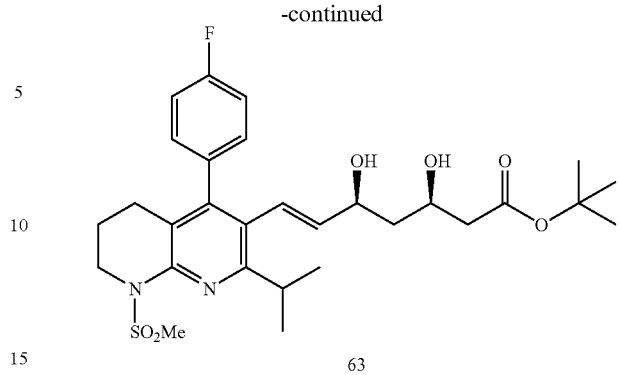

An additional preferred procedure is shown in Scheme 23. Intermediate 62 is treated with 3 equivalents of HCl in a THF-methanol mixture at or around 15° C. for about 2.5 h. The mixture is then treated with sodium hydroxide (5 equivalents) at the same temperature for about 1 h. After an extractive workup, acidification and crystallization a compound II of the invention (wherein $R_1$=4-fluorophenyl, $R_2$=isopropyl, $R_3$=$SO_2CH_3$, U=bond, and V, W and Y=$CH_2$) is obtained as the free carboxylic acid.

Scheme 23

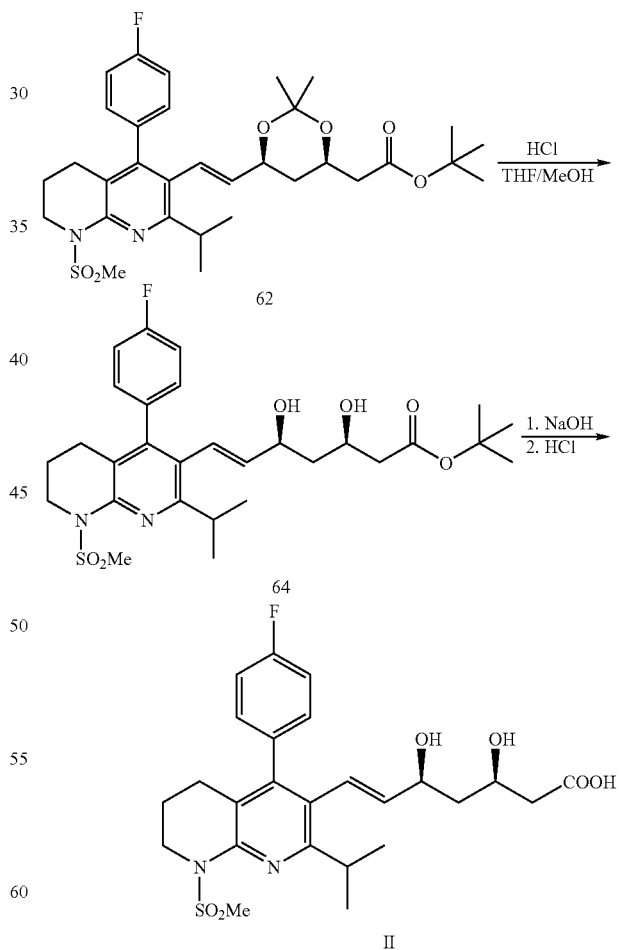

An additional preferred procedure for the preparation of a compound of structure II of the invention (wherein $R_1$=4-fluorophenyl, $R_2$=isopropyl, $R_3$=$SO_2CH_3$, U=bond, and V, W and Y=$CH_2$) as the calcium salt is shown in Scheme 24. Intermediate 62 is treated as described in Scheme 23. After the final acidification, the mixture is treated with calcium hydroxide and the mixture is crystallized to provide a compound of structure IIA of the invention (wherein $R_1$=4-fluorophenyl, $R_2$=isopropyl, $R_3$=$SO_2CH_3$, U=bond, and V, W and Y=$CH_2$).

Scheme 24

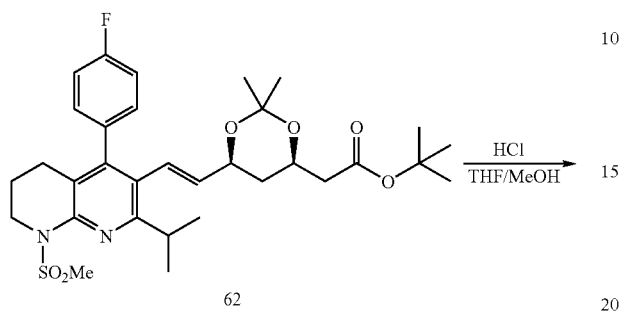

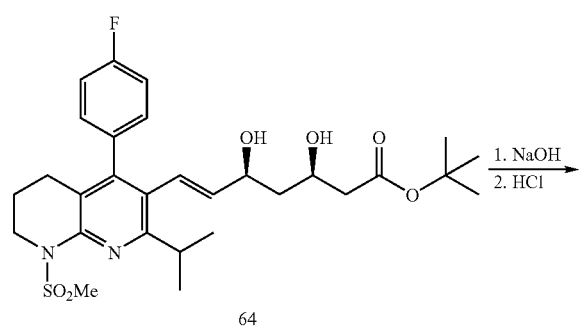

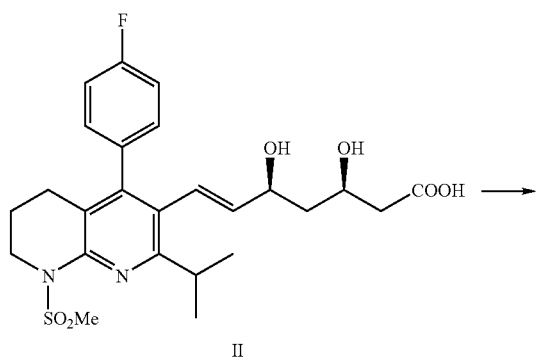

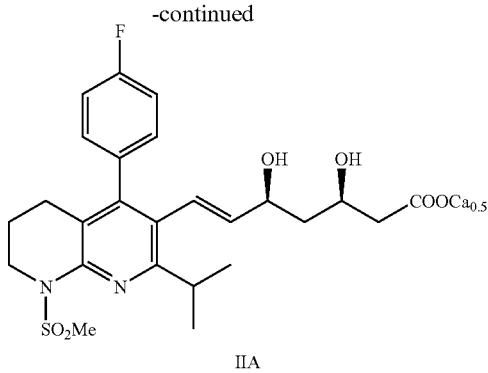

An alternate route to intermediate 58 is shown below in Scheme 25. A mixture of lactam 64 and a base such as lithium hexamethylsilazide, prepared at −25° C. to −35° C. in THF, MTBE or methanol-THF was added to reagent 3 (wherein $R_1$=4-fluorophenyl and $R_2$=isopropyl and R=methyl) employing a molar ratio of 3:64 within the range from about 1:1 to about 1.5:1, at a temperature within the range from about −25° C. to about −35° C., preferably about −20° C. After quenching extractive workup and crystallization from ethyl acetate-hexane, for example, intermediate 65 was obtained. Intermediate 65 was, in turn, treated with an acid, such as hydrochloric acid or p-toluenesulfonic acid, preferably trifluoroacetic acid, employing a molar ratio of acid:65 within the range from about 2.5:1 to about 1.5:1, to provide intermediate 66. Intermediate 66 is treated with an activating agent such as $PCl_5$ in an inert solvent such as dichloromethane or α, α, α-trifluorotoluene, preferably dichloroethane at elevated temperature, for example within the range from about 50 to about 60° C. preferably about 55° C., employing a molar ratio of $PCl_5$:66 within the range from about 1:1 to about 2.5:1, preferably about 1.2:1. After quenching and a basic workup, the intermediate was treated with ammonium acetate in a solvent such as methanol at elevated temperature, for example 55° C. The resultant intermediate (68) was treated with a) methanesulfonyl chloride (MSC) and b) diisopropylethylamine (DIPEA) in ethyl acetate below room temperature, within the range from about 15° C. to about 0° C., preferably about 0° C., employing a molar ratio of MSC:68 within the range from about 1.2:1 to about 2:1, and a molar ratio of DIPEA:MSC within the range from about 1.2:1 to about 2:1. The resulting product in ethyl acetate was then oxidized with manganese dioxide or DDQ, preferably aqueous ceric ammonium nitrate (CAN) to provide 58.

Scheme 25

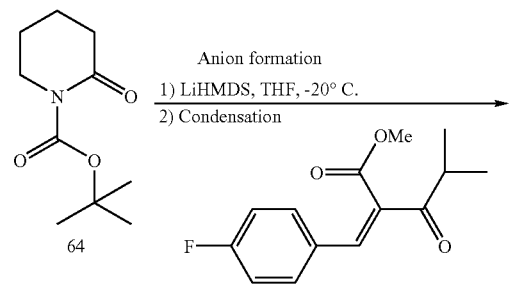

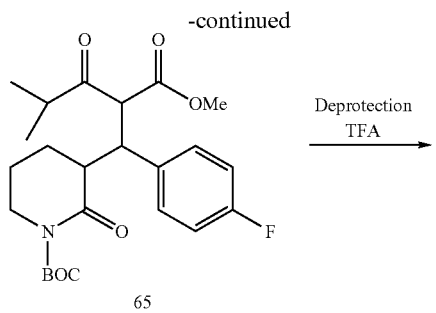

65

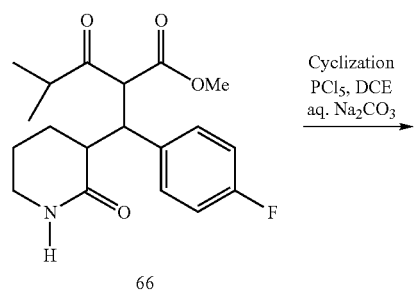

66

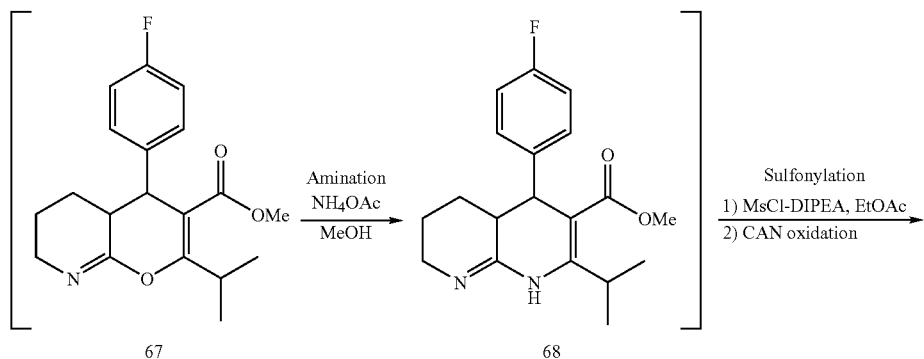

67                                68

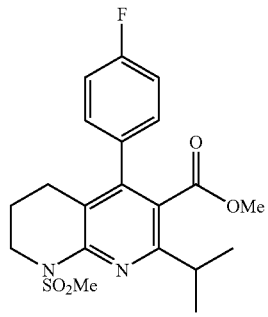

58

An alternative sequence to prepare intermediate 68 is shown in Scheme 26. Intermediate 66 is treated with PCl₅ in dichloromethane or α, α, α-trifluorotoluene, preferably dichloroethane, at elevated temperature, within the range from about 50° C. to about 75° C., preferably about 70° C., employing a molar ratio of PCl₅:66 within the range from about 1.2:1 to about 2.5:1. The reaction is quenched with ammonia in methanol below room temperature and filtered. When the resultant intermediate 67 is treated with ammonia/methanol or ammonium chloride, preferably ammonium acetate in ethanol or isopropanol, preferably methanol, at ambient temperature, employing a molar ratio of ammonium acetate:67 within the range from about 2:1 to about 6:1, preferably about 4:1, intermediate 69 may be obtained. The reaction mixture containing intermediate 69 can then be heated above room temperature, within the range from about 50° C. to about 65° C., preferably from about 60° C. to about 65° C., to effect conversion to intermediate 68.

Scheme 26

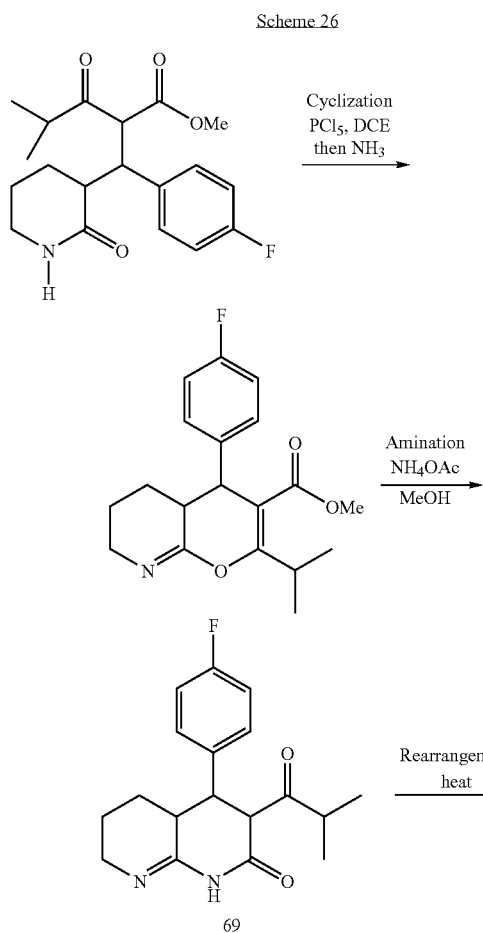

An alternate procedure to prepare intermediate 57 is shown in Scheme 27. Intermediate 66 (or equally well, intermediate 65) is treated with PCl$_5$ in dichloroethane, dichloromethane or α, α, α-trifluorotoluene, preferably dichloroethane, at elevated temperature within the range from about 60° C. to about 70° C., preferably about 65° C., employing a molar ratio of PCl$_5$:66 or 65 within the range from about 2.5:1 to about 1.2:1. The reaction is quenched with ammonia in methanol and worked up. The resultant intermediate is first treated with ammonium acetate in ethanol or isopropanol, preferably methanol at elevated temperature within the range from about 50° C. to 65° C., preferably about 60° C. and then with an oxidizing agent such as manganese acetate, preferably cupric acetate, at reflux. Compound 57 is obtained after workup and chromatography.

Scheme 27

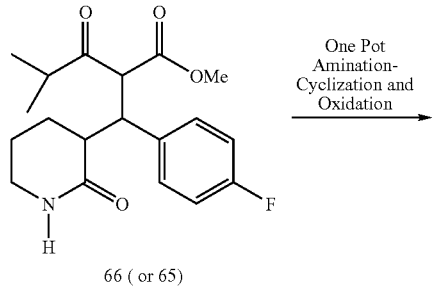

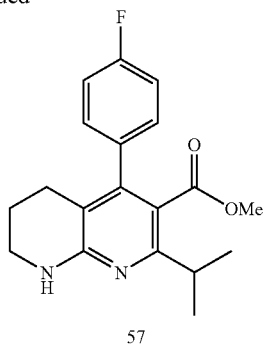

Compounds of the invention of structures I and II wherein n=1, i.e. pyridine N-oxides, may be prepared from intermediates 5-14. The pyridine ring may be oxidized with a variety of reagents such as hydrogen peroxide/acetic acid; an oxaziridine-based oxidant such as perfluoro-cis-2-butyl-3-propyloxaziridine; or a metal-catalyzed reagent mixture such as methylrhenium trioxide/hydrogen peroxide. The protecting groups may then be removed as described in Scheme 4.

An alternative route may be used wherein: 1) intermediate 5-14 is treated with acid under mild conditions to remove the acetonide group; 2) the diol is protected with a bulky silyl protecting group such as tert-butyldimethylsilyl or triethylsilyl; 3) the pyridine ring is oxidized as described in the preceding paragraph; and 4) the protecting groups are removed by sequential treatment with fluoride ion or hydrofluoroacid and then with base.

In the above schemes, the intermediates 9, 10, 48, 49, 50, 51, 53, 57, 58, 65, 66, 67, 68 and 69 are novel and form part of the present invention.

Compounds containing dihydroxy acid HMG-CoA binding domain side chains may be prepared in homochiral form, which is preferred, or may be prepared as racemic mixtures (3S*, 5R*) and may later be resolved to obtain the 3S, 5R isomer.

The compounds of the invention are inhibitors of 3-hydroxy-3-methyl-glutaryl coenzyme A (HMG-CoA) reductase and thus are useful in inhibiting cholesterol biosynthesis and/or in lowering triglycerides, in a manner similar to atorvastatin, pravastatin, simvastatin, lovastatin, cerivastatin, rosuvastatin, fluvastatin, pitavastatin, and the like.

A further aspect of the present invention is a pharmaceutical composition containing at least one of the compounds of formula I or II of the present invention in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations. Such dosage forms contain from 0.1 to 1500 mg of active compound per dosage, for use in the treatment. The dose to be administered depends on the unitary dose, the symptoms, and the age and the body weight of the patient.

The compounds of the present invention can be administered in a similar manner as known compounds suggested for use in inhibiting cholesterol biosynthesis, such as pravastatin, lovastatin, simvastatin, rosuvastatin, atorvastatin, cerivastatin, fluvastatin, pitavastatin, and the like, in mammalian species such as humans, dogs, cats and the like. Thus, the compounds of the invention may be administered in an amount from about 0.1 to 500 mg in a single dose or in the form of individual doses from 1 to 4 times per day, preferably 0.5 to 200 mg daily or in sustained release form.

The HMG CoA reductase inhibitors of formula I or II may be employed in combination with all therapeutic agents which are useful in combination with HMG CoA reductase inhibitors.

Thus, where desired, the compounds of structure I or II may be used in combination with one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-Alzheimer's agents, anti-dementia agents, antiosteoporosis agents, and/or hormone replacement therapeutic agents, and/ or other therapeutic agents, and/or other cardiovascular agents (including anti-anginal agents, anti-arrhythmic agents, anti-atherosclerosis agents, anti-inflammatory agents, antiplatelet agents, anti-heart failure agents), anti-cancer agents, anti-infective agents, hormone replacement agents, growth hormone secretagogues, selective androgen receptor modulators (SARMs), and/or other therapeutic agents which may be administered orally in the same dosage form or in a separate oral dosage form, or by injection.

The hypolipidemic agent or lipid-lowering agent or other lipid agent or lipid modulating agent which may be optionally employed in combination with the compounds of formula I of the invention may include 1, 2, 3 or more MTP inhibitors, rimonabant, squalene synthetase inhibitors, PPAR α agonists, PPAR dual α/γ agonists, PPAR δ agonists, fibric acid derivatives, ACAT inhibitors, lipoxygenase inhibitors, cholesterol absorption inhibitors, ileal Na$^+$/bile acid cotransporter inhibitors, upregulators of LDL receptor activity, cholesteryl ester transfer protein inhibitors, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712, 279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2, 2,2-trifluoroethyl)-9H-fluorene-9-carboxamide

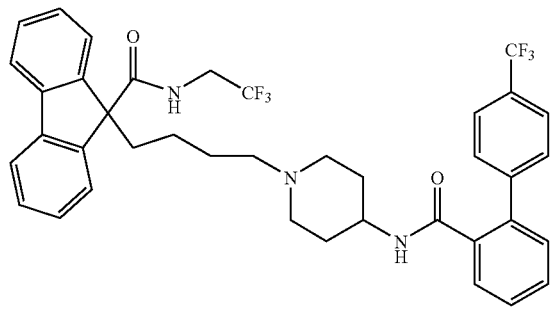

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp. 1869-1871, including isoprenoid (phosphinyl-methyl)phosphonates as well as other known squalene synthetase inhibitors, for example, as disclosed in U.S. Pat. Nos. 4,871,721 and 4,924, 024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., Ph.D. dissertation, June, 1987, Dept. Med. Chem. U of Utah, Abstract, Table of Contents, pp. 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, fenofibrate, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (ER niacin, Niaspan), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9-15 (1999), (Avasimibe); "The ACAT inhibitor, CI-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962

(Taisho Pharmaceutical Co. Ltd.), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd.) and LY295427 (Eli Lilly).

The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The other lipid agent or lipid-modulating agent may be a cholesteryl transfer protein inhibitor (CETP) such as Pfizer's CP-529,414 (torcetrapib) as well as those disclosed in WO/0038722 and in EP 818448 (Bayer) and EP 992496, and Pharmacia's SC-744 and SC-795 as well as CETi-1 and JTT-705.

The hypolipidemic agent may be an ileal $Na^+$/bile acid cotransporter inhibitor such as disclosed in Drugs of the Future, 24, 425-430 (1999).

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201;

a beta-lactam cholesterol absorption inhibitor such as disclosed in EP 675714;

an HDL upregulator such as an LXR agonist, a PPAR α-agonist and/or an FXR agonist;

an α-glucosidase inhibitor, an aldose reductase inhibitor and/or an LDL catabolism promoter such as disclosed in EP 1022272;

a sodium-proton exchange inhibitor such as disclosed in DE 19622222;

an LDL-receptor inducer or a steroidal glycoside such as disclosed in U.S. Pat. No. 5,698,527 and GB 2304106;

an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E;

isoniazid as disclosed in WO 97/35576;

a cholesterol absorption inhibitor, an HMG-CoA synthase inhibitor, or a lanosterol demethylase inhibitor as disclosed in WO 97/48701;

a PPAR δ agonist for treating dyslipidemia;

a PPAR α agonist for treating dyslipidemia;

a dual PPAR α/γ agonist such as muraglitazar (Bristol Myers-Squibb), tesaglitazar (AstraZeneca) or MK-767 (Merck/Kyorin/Banyu);

or a sterol regulating element binding protein-I (SREBP-1) as disclosed in WO 2000/050574, for example, a sphingolipid, such as ceramide, or neutral sphingomyelenase (N-SMase) or fragment thereof.

Preferred hypolipidemic agents are cholesterol absorption inhibitors such as ezetimibe, cholesterol ester transfer protein (CETP) inhibitors such as torcetrapib and JTT-705, dual PPAR α/δ agonists such as muraglitazar and tesaglitazar, as well as niacin and/or cholestagel.

The above-mentioned U.S. patents are incorporated herein by reference. The amounts and dosages employed will be as indicated in the Physician's Desk Reference and/or in the patents set out above or as otherwise known in the art.

The compounds of formula I of the invention will be employed in a weight ratio to the hypolipidemic agent (where present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent or other lipid agent or lipid modulating agent will be as disclosed in the various patents and applications discussed above.

The dosages and formulations for the other hypolipidemic agent or other lipid agent or lipid modulating agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 200 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The anti-atherosclerotic agent includes a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties," Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The antidiabetic agent which may be optionally employed in combination with the HMG-CoA reductase inhibitor of formula I may be 1, 2, 3 or more antidiabetic agents or antihyperglycemic agents including insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, aP2 inhibitors, PPAR α/γ dual agonists, dipeptidyl peptidase IV (DP4) inhibitors, SGLT2 inhibitors, glycogen phosphorylase inhibitors, and/or meglitinides, and/or glucagon-like peptide-1 (GLP-1), and/or a PTP-1B inhibitor (protein tyrosine phosphatase-1B inhibitor), as well as insulin and slow release insulin (Basulin™ (Flamel)).

The antidiabetic agent may be an oral antihyperglycemic agent preferably a biguanide such as metformin or phenformin or salts thereof, preferably metformin HCl.

Where the antidiabetic agent is a biguanide, the compounds of structure I or II will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I or II will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I or II will be employed in a weight ratio to the glucosidase inhibitor within the range from about 0.01:1 to about 100:1, preferably from about 0.05:1 to about 10:1.

The compounds of structure I or II may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I or II will be employed in a weight ratio to the thiazolidinedione in an amount within the range from about 0.01:1 to about 100:1, preferably from about 0.05:1 to about 10:1.

The sulfonyl urea and PPAR γ agonists in amounts of less than about 150 mg oral antidiabetic agent may be incorporated in a single tablet with the compounds of structure I or II.

The compounds of structure I or II may also be employed in combination with a antihyperglycemic agent such as insulin or slow release insulin (Basulin™), or with glucagon-like peptide-1 (GLP-1) or mimetic such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the PPAR anti-diabetic agent may be employed in amounts within the range from about 0.01 to about 2000 mg/day which may be administered in single or divided doses one to four times per day.

Where present insulin and other anti-diabetic agents as set out above may be employed in formulations, amounts and dosing as indicated by the Physician's Desk Reference.

Where present GLP-1 peptides or mimetics may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The antidiabetic agent or other lipid agent may also be a PPAR modulator such as a PPAR α/γ dual agonist such as tesaglitazar (Astra/Zeneca), muraglitazar (Bristol Myers-Squibb), MK-767 (Merck/Kyorin/Banyu), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), and in U.S. application Ser. No. 09/664,598, filed Sep. 18, 2000, (attorney file LA29) the disclosure of which is incorporated herein by reference, employing dosages as set out therein, which compounds designated as preferred are preferred for use herein.

The antidiabetic agent may be an SGLT2 inhibitor such as disclosed in U.S. Pat. Nos. 6,414,126 and 6,515,117, employing dosages as set out therein. Preferred are the compounds designated as preferred in the above patents.

The antidiabetic agent may be an aP2 inhibitor such as disclosed in U.S. Pat. No. 6,548,529, employing dosages as set out herein. Preferred are the compounds designated as preferred in the above patent.

The antidiabetic agent may be a DPP4 inhibitor such as disclosed in U.S. Pat. No. 6,395,767, U.S. Pat. No. 6,573,287, U.S. Pat. No. 6,395,767 (BMS-477118 (preferred), BMS-471211 and BMS 538305), WO99/38501, WO99/46272, WO99/67279 (PROBIODRUG), WO99/67278 (PROBIODRUG), WO99/61431 (PROBIODRUG), MK-431, NVP-LAF-237, NVP-DPP728A (1-[[[2-[(5-cyanopyridin-2-yl) amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537-1540, 2-cyanopyrrolidides and 4-cyanopyrrolidides as disclosed by Ashworth et al, Bioorg. & Med. Chem. Lett., Vol. 6, No. 22, pp. 1163-1166 and 2745-2748 (1996) employing dosages as set out in the above references.

The meglitinide which may optionally be employed in combination with the compound of formula I or II of the invention may be repaglinide or Starlix® (Novartis), nateglinide (Novartis) or KAD1229 (PF/Kissei), with repaglinide being preferred.

The antidiabetic compound may be a melanocortin receptor agonist such as a spiropiperidine as disclosed in WO 99/64002.

The HMG CoA reductase inhibitor of formula I or II will be employed in a weight ratio to the meglitinide, PPAR modulator such as a PPAR γ agonist, PPAR α agonist, PPAR δ agonist or antagonist, PPAR α/γ dual agonist, aP2 inhibitor, DPP4, inhibitor or SGLT2 inhibitor or other antidiabetic agent within the range from about 0.01:1 to about 100:1, preferably from about 0.05:1 to about 10:1.

The other type of therapeutic agent which may be optionally employed with the HMG CoA reductase inhibitor of formula I or II may be 1, 2, 3 or more of an anti-obesity agent including a beta 3 adrenergic agonist, a lipase inhibitor, a serotonin and/or dopamine modulator/mimic, norepinephrine (NE) modulator/mimic, an aP2 inhibitor, a thyroid receptor beta drug, a PTP-1B inhibitor, an anorectic agent, a PPAR modulator including PPAR γ antagonists, PPAR α agonists, PPAR δ agonists, a CCKA agonist, a CB1 antagonist, a leptin inhibitor such as a leptin receptor activator, a neuropeptide Y antagonist, a melanocortin-4-receptor (MC4R) agonist, a CB-1 inverse agonist, a fatty acid oxidation upregulator or inducer (such as Famoxin® Genset), a 5-HT2c agonist, and an acetyl CoA carboxylase (ACC) inhibitor.

The beta 3 adrenergic agonist which may be optionally employed in combination with a compound of formula I or II may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The neuropeptide Y antagonists which may be optionally employed in combination with a compound of formula I or II include those described in WO 0113917 (BMS) or in U.S. Pat. No. 6,218,408 (Synaptic) and in WO 0114376 (Banyu).

The lipase inhibitor which may be optionally employed in combination with a compound of formula I or II may be orlistat or ATL-962 (Alizyme), with orlistat being preferred.

The serotonin and dopoamine modulator/mimic and/or norepinephrine modulator/mimic which may be optionally employed in combination with a compound of formula I or II may be sibutramine.

The anorectic agent which may be optionally employed in combination with a compound of formula I or II may be topiramate, Axokine® (Regeneron) (analogue of Ciliary Neurotrophic Factor) dexamphetamine, phentermine, phenylpropanolamine or mazindol, with dexamphetamine or topiramate being preferred.

The thyroid receptor beta compound which may be optionally employed in combination with a compound of formula I or II may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

Examples of the ACC inhibitors which may be employed include those described in WO 03/072197.

Examples of the CB-1 inverse agonists which may be employed include SR-141716 (Sanofi) and FLV-319 (Folvay).

Examples of the 5-HT2c agonists which may be employed include compounds as disclosed in WO 00/77010.

The CCKA agonists which may be employed herein include Glaxo-SmithKline's GI-181,771 and Sanofi's SR146,131.

The PTP-1B inhibitor which may be an anti-obesity and/or an antidiabetic agent include those disclosed in WO 99/585, 521, WO 99/58518, WO 99/58522 and WO 99/61435.

The anti-obesity agent employed may also be Pfizer's P57 or CP-644,673 (licensed from Phytopharm).

The various anti-obesity agents described above may be employed in the same dosage form with the compound of formula I or II or in different dosage forms, in dosages and regimens as generally known in the art or in the PDR.

The antihypertensive agents which may be employed in combination with the HMG CoA reductase inhibitors of the invention include ACE inhibitors, angiotensin II receptor antagonists, MR agonist, NEP inhibitors such as candoxatril, NEP/ACE inhibitors, as well as calcium channel blockers (such as verapamil and amlodipine besylate), T-channel calcium antagonists (such as mibefradil), β-adrenergic blockers, diuretics, α-adrenergic blockers (such as doxazosin mesylate and terazosin HCl), dual action receptor antagonists (DARA), heart failure drugs such as digoxin, and other types of antihypertensive agents.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Preferred ACE inhibitors are captopril, fosinopril, enalapril, lisinopril, cetapril, cilazapril, indalapril, spirapril, perindopril, ceranapril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, U.S. Pat. No. 5,552,397, U.S. Pat. No. 5,504,080, U.S. Pat. No. 5,612, 359, U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, gemopatrilat ([S[(R*,R*)]-hexahydro-6-[(2-mercapto-1-oxo-3-phenylpropyl)amino]-2,2-dimethyl-7-oxo-1H-azepine-1-acetic acid) and CGS 30440.

The angiotensin II receptor antagonist (also referred to herein as angiotensin II antagonist or AII antagonist) suitable for use herein includes, but is not limited to, irbesartan, losartan, valsartan, candesartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

It will be appreciated that preferred dosages of ACE inhibitor and AII antagonist will be as set out in the latest edition of the Physician's Desk Reference (PDR).

Dual action receptor antagonists (DARA) suitable for use herein include those disclosed in U.S. application Ser. No. 09/513,779, filed Feb. 25, 2000, and Ser. No. 09/604,322, filed Jun. 26, 2000.

Other examples of preferred antihypertensive agents suitable for use herein include omapatrilat (Vanlev®), gemopatrilat, amlodipine besylate (Norvasc®), prazosin HCl (Minipress®), verapamil, nifedipine, diltiazem, felodipine, nisoldipine, isradipine, nicardipine, beta blockers such as nadolol, atenolol (Tenormin®), sotalol, terazosin, doxazosin, carvedilol, and propranolol, and clonidine HCl (Catapres®).

Diuretics which may be employed in combination with compounds of formula I or II include hydrochlorothiazide, torasemide, furosemide, spironolactone, and indapamide.

Antiplatelet agents which may be employed in combination with compounds of formula I or II of the invention include aspirin, clopidogrel, ticlopidine, dipyridamole, CS-747, (Lilly), abciximab, tirofiban, eptifibatide, anagrelide, and ifetroban, with clopidogrel and aspirin being preferred.

Anti-thrombotic agents which may be employed in combination with compounds of formula I or II of the invention include melagatran and ximelagatran (Exanta™ Astra Zeneca), warfarin and Factor Xa inhibitors such as razaxaban.

The antihypertensive agents, diuretics and antiplatelet drugs may be employed in amounts as indicated in the PDR. Ifetroban may be employed in amounts as set out in U.S. Pat. No. 5,100,889.

Anti-Alzheimer's agents or anti-dementia agents suitable for use herein with the HMG CoA reductase inhibitors of the invention include tacrine HCl (Cognex®) and donepezil (Aricept®), as well as γ-secretase inhibitors, β-secretase inhibitors and/or antihypertensive agents. Dosages employed will be as set out in the PDR.

Antiosteoporosis agents suitable for use herein in combination with the HMG CoA reductase inhibitors of the invention include parathyroid hormone or bisphosphonates, such as MK-217 (alendronate) (Fosamax®) as well as Ca receptor agonists and progestin receptor agonists. Dosages employed will be as set out in the PDR.

The hormone replacement therapeutic agents, where present, will be employed in dosages as set out in the latest edition of the PDR. Examples of such agents include selective estrogen receptor modulators (SERMs) such as raloxifen, tamoxifen or lasoxifen.

The HMG CoA reductase compound of the invention may also be employed in combination with a tyrosine kinase inhibitor such as disclosed in WO 2000/053605.

The selective androgen receptor modulator (SARM) suitable for use herein may be LGD-2226 (Ligand) or those compounds disclosed in WO 03/011824.

The antiarrhythmic agents suitable for use herein include β-blockers as set out herein including sotalol and amioderome, calcium channel blockers as set out herein including verapamil, nifedipine, amlodipine-besylate, and diltiazem, which may also be used in combination with a debrillator device such as a pace maker;

coenzyme Q sub. 10 such as disclosed in U.S. Pat. Nos. 5,316,765, 4,933,165, 4,929,437;

an agent that upregulates type III endothelial cell nitric acid syntase such as disclosed in WO 2000/003746;

a chondroprotective compound such as a polysulfated glycosaminoglycan (PSGAG), glucosamine, chondroitin sulfate (CS), hyaluronic acid (HA), pentosan polysulfate (PPS), doxycycline or minocycline, such as disclosed in EP 970694;

a cyclooxygenase (COX)-2 inhibitor, such as celecoxib (Celebrex® (Searle)) or rofecoxib (Vioxx® (Merck)) or a glycoprotein IIa/IIIb receptor antagonist such as disclosed in WO 99/45913 and tirofiban or abciximab;

a 5-HT reuptake inhibitor such as disclosed in WO 99/44609;

anti-anginal agents such as vasodilators, for example, isosorbide dinitrate, or nitroglycerin;

a growth hormone secretagogue such as disclosed in U.S. application Ser. No. 09/662,448, filed Sep. 14, 2000, and U.S. Provisional application 60/203,335, filed May 11, 2000, and MK-677 (Merck), Pfizer's CP-424391 and Lilly's LY 444, 711;

anti-atherosclerosis agents such as ACAT inhibitors and lipoxygenase inhibitors as described herein and phospholipase inhibitors;

anti-infective agents such as quinolones, for example, ciprofloxacin, ofloxacin, and Tequin® (Bristol-Myers Squibb), macrolides such as erythromycin and clarithromycin (Biaxin® (Abbott)), and azithromycin (Zithromax® (Pfizer)); or an immunosuppressant (for use in transplantations) such as cyclosporine, mycophenolate mofetil, azathioprine and the like.

As used herein, the phrase "antineoplastic agent" refers to compounds which prevent cancer cells from multiplying. In general, the antineoplastic agents used herein prevent cancer cells from multiplying by: (1) interfering with the cell's ability to replicate DNA, or (2) inducing apoptosis in the cancerous cells.

Examples of antineoplastic agents which are suitable for use in combinations of this invention include, but are not limited to, microtuble-stabilizing agents such as the taxanes, for example, paclitaxel (also known as Taxol®), docetaxel (also known as Taxotere®), 7-O-methylthio-methylpaclitaxel (disclosed in U.S. Pat. No. 5,646,176), 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 60/179,965 filed on Feb. 3, 2000, and example 17 herein), C-4 methyl carbonate paclitaxel (disclosed in WO 94/14787), the epothilone, such as epothilone A, epothilone B, epothilone C, epothilone D, desoxyepothilone A, desoxyepothilone B, [1S-[1R*,3R*(E),7R*,10S*,11R*,12R*, 16S*]]-7,11-dihydroxy-8,8,10,12,16-pentamethyl-3-[1-methyl-2-(2-methyl-4-thiazolyl)ethenyl]-4-aza-17-oxabicyclo [14.1.0]hepta-decane-5,9-dione (disclosed in WO 99/02514), [1S-[1R*,3R*(E),7R*, 110S*,11R*, 12R*, 16S*]]-3-[2-[2-(aminomethyl)-4-thiazolyl]-1-methylethenyl]-7,11-di-hydroxy-8,8,10,12,16-pentamethyl-4,17-dioxabicyclo[14.1.0]-heptadecane-5,9-dione (disclosed in U.S. Ser. No. 09/506, 481 filed on Feb. 17, 2000, and examples 7 and 8 herein), and derivatives thereof; microtuble-disruptor agents; alkylating agents; anti-metabolites; epidophyllotoxin; an antineoplastic enzyme; a topoisomerase inhibitor; procarbazine; mitoxantrone; platinum coordination complexes; biological response modifiers; growth inhibitors; hormonal/antihormonal therapeutic agents; and haematopoietic growth factors.

Other classes of antineoplastic agents suitable for use in the method of the present invention include, but are not limited to, the anthracycline family of drugs, the vinca drugs, the mitomycins, the bleomycins, the cytotoxic nucleosides, discodermolide, the pteridine family of drugs, diynenes, aromatase inhibitors, and the podophyllotoxins. Particularly useful members of those classes not previously mentioned include, for example, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, and the like. Other useful antineoplastic agents include estramustine, cisplatin, carboplatin, cyclophosphamide, bleomycin, tamoxifen, ifosfamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, and interleukins.

It will be appreciated that unless otherwise specified the dosage regiment for therapeutic agents used in combination with the compounds of the invention will be as specified in the PDR.

In carrying out the method of the invention for treating hypercholesterolemia, hyperlipidemia, hyperlipoproteinemia, hypertriglyceridemia, or atherosclerosis, and related diseases, or Alzheimer's disease or osteoporosis, or other disclosures as set out hereinbefore, a pharmaceutical composition will be employed containing the compounds of structure I, with or without other cholesterol lowering agents, osteoporosis agents, Alzheimer's agents, antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 0.1 to about 500 mg of a compound of formula I or II. The dose for adults is preferably between 0.5 and 1,000 mg per day, which can be administered in a single dose or in the form of individual doses from 1-4 times per day and also single dose once weekly (5 to 1000 mg).

A typical injectable preparation is produced by aseptically placing 250 mg of compounds of structure I or II into a vial, aseptically freeze-drying and sealing. For use, the contents of the vial are mixed with 2 mL of physiological saline, to produce an injectable preparation.

The following abbreviations are employed in the Examples and elsewhere herein:

μL=microliter
AcCN=acetonitrile
AIBN=2,2'-azobisisobutyronitrile
aq.=aqueous
Bn=benzyl
Boc=tert-butoxycarbonyl
bp=boiling point
brine=saturated aqueous sodium chloride
Cbz=carbobenzyloxy or carbobenzoxy or benzyloxycarbonyl
DDQ=2,3-Dichloro-5,6-dicyano-1,4-benzoquinone
DEAD=diethyl azodicarboxylate
Dess-Martin periodinane=1,1,1-tris(acetyloxy)-1,1-dihydro-1,2-Benziodoxol-3(1H)-one
DI water=deionized water
DIBAL=diisobutylaluminum hydride
DIPEA=diisopropyl ethylamine
DMF=N,N-dimethylformamide
DMPU=1,3-dimethyl-3,4,5,6-tetrahydro-2(1H)-pyrimidinone
EDAC=3-ethyl-3'-(dimethylamino)propyl-carbodiimide hydrochloride (or 1-[(3-(dimethyl)amino)propyl])-3-ethylcarbodiimide hydrochloride)
EDCI=1-[3-(dimethylamino)propyl]-3-ethylcarbodiimide hydrochloride.
Et=ethyl
$Et_2NH$=diethylamine
FMOC=fluorenylmethoxycarbonyl
g=gram(s)
h or hr=hour(s)
HOAc or AcOH=acetic acid
HOAT=1-hydroxy-7-azabenzotriazole
HOBT or $HOBT.H_2O$=1-hydroxybenzotriazole hydrate
HPLC=high performance liquid chromatography
i-Bu=iso-butyl
KF=Karl Fisher titration
L=liter
LC/MS=high performance liquid chromatography/mass spectrometry
LDA=lithium diisopropylamide
LiHMDS=lithium bis(trimethylsilyl)amide
$LiN(TMS)_2$=lithium bis(trimethylsilyl)amide
LRMS=low resolution mass spectrum
mCPBA=m-chloro-peroxy-benzoic acid
Me=methyl
meq=milliequivalent
mg=milligram(s)
min=minute(s)
mL=milliliter
mmol=millimole(s)
mol=moles
mp=melting point
MS or Mass Spec=mass spectrometry
MTBE=methyl t-butyl ether
NaHMDS=sodium bis(trimethylsilyl)amide
n-BuLi=n-butyllithium
NMM=N-methyl morpholine
NMO=methylmorpholine N-oxide
NMR=nuclear magnetic resonance
ODS=ccta decyl silyl
Pd/C=palladium on carbon
Ph=phenyl
$PPh_3$=triphenylphosphine
PS-PB-CHO=1% Cross linked polystyrene with (4-formyl-3-methoxyphenoxy)methyl linker.
$PtO_2$=platinum oxide
PTSH=N-phenylthiotetrazole
PyBOP reagent=benzotriazol-1-yloxy-tripyrrolidino phosphonium hexafluorophosphate
Red-AL=sodium bis(2-methoxyethoxy)aluminum hydride
RP=Reverse Phase
RT, rt=room temperature
sat or sat'd=saturated
TBAF=tetrabutylammonium fluoride
TEA=triethylamine
TEMPO=2,2,6,6-tetramethyl-1-piperidinyloxy free radical
TFA=trifluoroacetic acid TFFH=Tetramethylfluoroformamidinium hexafluorophosphate.
THF=tetrahydrofuran
TLC=thin layer chromatography
TMS=trimethylsilyl
TPAP=tetrapropylammonium perruthenate
WSC=1-[3-(dimethylamino)propyl]-3-ethylcarbodiimide hydrochloride.

The following RP-HPLC and LC-MS methods were employed:

Method 1: Phenomenex ODS S5 column, 4.6 mm×30 mm; 5 mL/min; detection at 220 nm; solvent A=90:10 water:methanol, solvent B=10:90 water:methanol (both containing 0.1% trifluoroacetic acid); 0% B to 100% B (2 min linear gradient) and then hold.

Method 2: column-Phenomenex-Prime (S5 ODS column) 4.6 mm×50 mm; detection at 220 nm; flow-4 mL/min; solvent—A=10:90 methanol:water+0.1% TFA, B=90:10 methanol:water+0.1% TFA; linear gradient, 0% B to 100% B over 4 min and 100% B for 2 min.

Method 3: column-YMC-ODS-A (S5) 4.6 mm×50 mm column; detection at 220 nm; flow-4 mL/min; solvent—A=10:90 methanol:water+0.2% phosphoric acid, B=90:10 methanol:water+0.2% phosphoric acid; linear gradient, 0% B to 100% B over 4 min and 100% B for 2 min.

Method 4: column-YMC-ODS-A (S3) 6 mm×150 mm column; detection at 220 nm; flow-1.5 mL/min; solvent—A=10:90 methanol:water+0.2% phosphoric acid, B=90:10 methanol:water+0.2% phosphoric acid; linear gradient, 0% B to 100% B over 30 min and 100% B for 7 min.

Method 5: column-Phenomenex (S5) 4.6 mm×50 mm column; detection at 220 nm; flow-4 mL/min; solvent—A=10:90 methanol:water+0.2% phosphoric acid, B=90:10 methanol:water+0.2% phosphoric acid; linear gradient, 0% B to 100% B over 4 min and 100% B for 2 min.

EXAMPLES

The following Examples represent preferred embodiments of the invention. Compound names cited in the examples, unless otherwise noted, can be converted to structure drawings using the AutoNom (v 2.1) feature in ChemDraw Ultra v 6.0.4. or the AutoNom feature of ChemDraw Ultra v 8.0.3.

Example 1

(E)-(3R,5S)-7-[4-(4-Fluorophenyl)-2-isopropyl-8-methanesulfonyl-5,6,7,8-tetrahydro-[1,8]naphthyridin-3-yl]-3,5-dihydroxyhept-6-enoic Acid, Sodium Salt

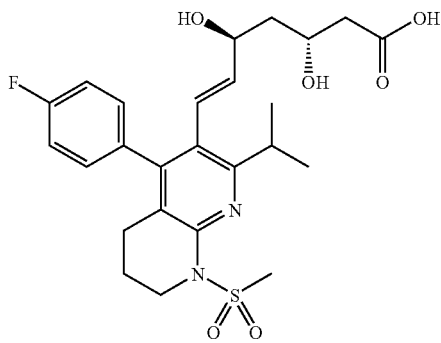

A. Methyl 6-amino-5-(3-ethoxy-3-oxopropenyl)-4-(4-fluorophenyl)-2-isopropylnicotinate To a slurry of 60% NaH in oil (6.55 g, 164 mmol) in THF (250 mL) at 0° C. was added triethyl phosphonoacetate (31.4 g, 140 mmol) over 25 min. The reaction mixture was then brought to room temperature for 20 min and cooled again to 0° C. A solution of methyl 6-amino-4-(4-fluorophenyl)-5-formyl-2-isopropyl-nicotinate (37.0 g, 117 mmol) in THF (100 mL) was added over 10 minutes and the reaction mixture was allowed to warm to room temperature. After an additional 40 minutes the reaction was quenched with water (400 mL) and then ethyl acetate (500 mL). The aqueous layer was extracted with an additional 200 mL of ethyl acetate and the combined extracts were dried with magnesium sulfate and concentrated to a residue (48 g). This material was crystallized from ether/hexane, and the crystalline material further purified by trituration with hot hexanes. The combined mother liquors from these steps were purified by silica gel chromatography using 0.2% methanol in methylene chloride. This yielded a total of 38.5 g (86%) of methyl 6-amino-5-(3-ethoxy-3-oxopropenyl)-4-(4-fluorophenyl)-2-isopropylnicotinate.

B. Ethyl 2-amino-4-(4-fluorophenyl)-6-isopropyl-5-methoxycarbonyl-3-pyridinepropanoate To a solution of the compound from Part A (37.4 g, 96.9 mmol) in ethyl acetate (400 mL) was added 2 g of 10% Pd/C. The mixture was placed under a 60 psig atmosphere of hydrogen. After 23 hours, the reaction mixture was passed through Celite® (60 mm dia.×50 mm) using an additional 500 mL of ethyl acetate to elute the product. The combined filtrates were concentrated in vacuo to provide ethyl 2-amino-4-(4-fluorophenyl)-6-isopropyl-5-methoxycarbonyl-3-pyridinepropanoate (37.3 g, 99%) as a pale yellow powder.

C. Methyl 4-(4-fluorophenyl)-2-isopropyl-7-oxo-5,6,7,8-tetrahydro-[1,8]naphthyridine-3-carboxylate A mixture of the compound from Part B (36.2 g, 93.3 mmol) and p-toluenesulfonic acid monohydrate (890 mg, 4.7 mmol) in toluene (300 mL) was heated to 100-110° C. for 3.5 hours. The solvent was removed in vacuo and the residue purified by silica gel chromatography (methanol/methylene chloride) to yield methyl 4-(4-fluorophenyl)-2-isopropyl-7-oxo-5,6,7,8-tetrahydro-[1,8]naphthyridine-3-carboxylate (29.4 g, 86.0 mmol, 92%) as a light tan powder.

D. Methyl 4-(4-fluorophenyl)-2-isopropyl-5,6,7,8-tetrahydro-[1,8]naphthyridine-3-carboxylate To a slurry of the compound from Part C (17 g, 50 mmol) in toluene (300 mL) was added 31.3 mL of 1.5 M RedAl® in toluene over 30 minutes. After an additional 110 minutes, the reaction was quenched by the slow addition of 3 mL of water followed by an additional 300 mL of water and 300 mL of ethyl acetate. The aqueous layer was extracted with an additional 2×150 mL of ethyl acetate. The combined ethyl acetate extracts were washed with brine (200 mL), and then dried with magnesium sulfate and concentrated. The residue was purified by silica gel chromatography (methylene chloride/hexane) to yield methyl 4-(4-fluorophenyl)-2-isopropyl-5,6,7,8-tetrahydro-[1,8]naphthyridine-3-carboxylate (12.8 g, 39 mmol, 78%) as a white solid.

E. Methyl 4-(4-fluorophenyl)-2-isopropyl-8-methanesulfonyl-5,6,7,8-tetrahydro-[1,8]naphthyridine-3-carboxylate To a solution of the compound from Part D (4.9 g, 15 mmol) and triethylamine (9.05 g, 89.6 mmol) in methylene chloride (60 mL) at −78° C. was added methanesulfonyl chloride (7.66 g, 67.2 mmol) over 10 minutes. A thick slurry ensued. An additional 2.0 equivalents of triethylamine and 2.5 equivalents of methanesulfonyl chloride were added. After a total of 80 minutes at −78° C., the reaction was quenched by the addition of saturated aqueous ammonium chloride (60 mL). The aqueous layer was extracted with an additional 2×60 mL of chloroform. The combined extracts were dried with magnesium sulfate, and the solution concentrated to 9.9 g of a light yellow oil. This residue was purified by silica gel chromatography (methanol/methylene chloride) to provide methyl 4-(4-fluorophenyl)-2-isopropyl-8-methanesulfonyl-5,6,7,8-tetrahydro-[1,8]naphthyridine-3-carboxylate (4.94 g, 12.16 mmol, 81%) as a white foam.

F. [4-(4-Fluorophenyl)-2-isopropyl-8-methanesulfonyl-5,6,7,8-tetrahydro-[1,8]naphthyridin-3-yl]-methanol To a solution of the compound from Part E (4.9 g, 12. mmol) in toluene (100 mL) at −78° C. was added 20.1 mL of 1.5 M DIBAL in toluene over 15 minutes. After 20 minutes, the reaction was quenched at −78° C. with 100 mL of saturated aqueous ammonium chloride and water (100 mL) was added to solubilize the solids formed. The aqueous layer was extracted with 2×150 mL of ethyl acetate. The combined extracts were dried over magnesium sulfate, and concentrated in vacuum to give 5.1 g of a white foam. This material was purified on a silica gel pad using 1% methanol in methylene chloride to yield [4-(4-fluorophenyl)-2-isopropyl-8-methanesulfonyl-5,6,7,8-tetrahydro-[1,8]naphthyridin-3-yl]-methanol (4.7 g, 103%) as white foam.

G. 4-(4-Fluorophenyl)-2-isopropyl-8-methanesulfonyl-5,6,7,8-tetrahydro-[1,8]naphthyridine-3-carboxaldehyde To a solution of the compound from Part F (4.491 g, 11.88 mmol) in methylene chloride (100 mL) was added KBr (141 mg, 1.19 mmol, 0.10 equiv) and TEMPO (92 mg, 0.59 mmol, 0.05 equiv). The solution was cooled to 0° C. and 19.8 mL of buffered bleach (Clorox® adjusted to pH 9.5 with solid NaHCO$_3$) was added over 5 minutes. Over the next 20 hours, the internal temperature was allowed to rise to 10° C. At this point, the reaction mixture was cooled to 0° C. and quenched with 100 mL of 10% Na$_2$S$_2$O$_3$ in water. The organic layer was then washed successively with 100 mL of 1 N NaOH and then twice with 100 mL of water. The organic layer was then passed directly through a silica gel column (60 mm dia.×90 mm) and eluted with methylene chloride. After collecting a forecut of 550 mL, the next 1000 mL were collected and concentrated to provide 4.0 g (90%) of 4-(4-fluorophenyl)-2-isopropyl-8-methanesulfonyl-5,6,7,8-tetrahydro-[1,8]naphthyridine-3-carboxaldehyde as a nearly white foam.

H. 1,1-Dimethylethyl(4R,6S)-(E)-6-{2-[4-(4-fluorophenyl)-2-isopropyl-8-methanesulfonyl-5,6,7,8-tetrahydro-[1,8]naphthyridin-3-yl]ethenyl}-2,2-dimethyl-[1,3]dioxan-4-acetate To a solution of the compound from Part G (4.0 g, 11 mmol) and 1,1-dimethylethyl(4R,6S)-2,2-dimethyl-6-(1-phenyl-1H-tetrazole-5-sulfonylmethyl)-[1,3]dioxan-4-yl-acetate (5.06 g, 11.2 mmol) in THF (100 mL) at −78° C. was added 13.83 mL of 1.0 M LiHMDS in THF over 5 minutes. After 20 minutes, the reaction was quenched at −78° C. by the addition of 100 mL of saturated aqueous sodium bicarbonate followed by the addition of ethyl acetate (200 mL). The aqueous layer was extracted with an additional 200 mL of ethyl acetate. The combined extracts were dried over magnesium sulfate and concentrated to 7.3 g of an off-white foam. This material was crystallized from ethanol/hexane to yield 1,1-dimethylethyl (4R,6S)-(E)-6-{2-[4-(4-fluorophenyl)-2-isopropyl-8-methanesulfonyl-5,6,7,8-tetrahydro-[1,8]naphthyridin-3-yl]ethenyl}-2,2-dimethyl-[1,3]dioxan-4-acetate (3.65 g, 6.06 mmol, 57%) as a white powder. The mother liquors were purified by silica gel chromatography (methanol/methylene chloride) and then by crystallization from ethanol/hexane to yield an additional 1.11 g (1.84 mmol, 17%).

I. (E)-(3R,5S)-7-[4-(4-Fluorophenyl)-2-isopropyl-8-methanesulfonyl-5,6,7,8-tetrahydro-[1,8]naphthyridin-3-yl]-3,5-dihydroxyhept-6-enoic Acid, Sodium Salt To a solution of the compound from Part H (4.73 g, 7.86 mmol) in THF (50 mL) was added 4.6 mL of 6 N aqueous HCl (28 mmol, 3.5 equiv). After 55 minutes, 26.6 mL of 2 N aqueous NaOH (47 mmol, 6.0 equiv) was added. After an additional 100 minutes, the THF was removed in vacuo to yield 35.2 g of a thick pale yellow slurry. This material was run directly through a column (50 mm dia.×65 mm) of 100 g of 40 μM C-18 silica gel (J.T. Baker catalog # 7025-00) eluting with 400 mL of water, followed by elution of product with 25% methanol in water (875 mL). The methanolic eluate was concentrated in vacuo. The residue was dissolved in ethanol and the mixture was filtered through a sintered funnel. The filtrate was concentrated in vacuo to provide the title compound (E)-(3R,5S)-7-[4-(4-fluorophenyl)-2-isopropyl-8-methanesulfonyl-5,6,7,8-tetrahydro-[1,8]naphthyridin-3-yl]-3,5-dihydroxyhept-6-enoic acid, sodium salt (3.28 g, 6.21 mmol, 79%) as a white foam: LS-MS (LRMS (ESI) m/z 507; method 1, $t_R$=1.53 min).

The Example 1 Part E compound was prepared using the following preferred method.

Example 1A

Methyl 4-(4-fluorophenyl)-2-isopropyl-8-methanesulfonyl-5,6,7,8-tetrahydro-[1,8]naphthyridine-3-carboxylate A. Methyl 2-[(4-fluorophenyl)-(2-methoxy-3,4,5,6-tetrahydro-pyridin-3-yl)-methyl]-4-methyl-3-oxo-pentanoate 6-Methoxy-2,3,4,5-tetrahydropyridine (102.7 g, 0.91 mole) was added over 25 min to a solution of lithium diisopropylamine (1.8 M, 505 mL, 0.91 mole) in THF (1.2 L) stirring at −60° C. under nitrogen. After stirring at −60° C. for 1 h, methyl 3-(4-fluorophenyl)-2-isobutyrylacrylate (175 g, 0.70 mole) was added over 75 min keeping the temperature below −50° C. The reaction was quenched with saturated ammonium chloride (750 mL) after the reaction had stirred at −60° C. for 35 min. After the reaction mixture had warmed to room temperature, ethyl acetate was added and the mixture transferred to a separatory funnel. The mixture was extracted with ethyl acetate (2×1 L). The combined organic layers were washed with 50% saturated ammonium chloride solution, water, and brine; dried over magnesium sulfate; and concentrated in vacuo to afford methyl 2-[(4-fluorophenyl)-(2-methoxy-3,4,5,6-tetrahydro-pyridin-3-yl)-methyl]-4-methyl-3-oxo-pentanoate (271 g).

B. Methyl 4-(4-fluorophenyl)-2-isopropyl-1,4,4a,5,6,7-hexahydro-[1,8]naphthyridine-3-carboxylate A mixture of Part A compound (271 g, 0.70 mol) and ammonium chloride (94 g, 1.75 mole) in methanol (2.3 L) was refluxed for 5.5 h. The reaction was then cooled to 4° C. and the solids present were removed by filtration. The filtrate was evaporated in vacuo. Methylene chloride was added to the residue and the resulting mixture was filtered again. Evaporation of the filtrate afforded methyl 4-(4-fluorophenyl)-2-isopropyl-1,4,4a,5,6,7-hexahydro-[1,8]naphthyridine-3-carboxylate (307 g): HPLC (method 1) $t_R$=1.6 min; LCMS (ESI, pos. ion spectrum) m/z 331 (M+H).

C. Methyl 4-(4-fluorophenyl)-2-isopropyl-8-methanesulfonyl-4,4a,5,6,7,8-hexahydro-[1,8]naphthyridine-3-carboxylate Methanesulfonyl chloride (75 ml, 0.97 mole) was added over 5 min to a solution of the compound from Part B (307 g, 0.70 mol) in methylene chloride (1.8 L) stirring at 0° C. Triethylamine (165 ml, 1.2 mole) was then added over 25 min keeping the temperature under 15° C. After 2.7 h, the reaction was quenched with water (1.2 L) and transferred to a separatory funnel. The mixture was extracted with methylene chloride (600 mL×2). The combined organic layers were dried over magnesium sulfate and concentrated in vacuo to afford methyl 4-(4-fluorophenyl)-2-isopropyl-8-methanesulfonyl-4,4a,5,6,7,8-hexahydro-[1,8]naphthyridine-3-carboxylate (327 g) after evaporation of the solvent: HPLC (method 1) $t_R$=2.3 min; LCMS (ESI, pos. ion spectrum) m/z 409 (M+H).

D. Methyl 4-(4-fluorophenyl)-2-isopropyl-8-methanesulfonyl-5,6,7,8-tetrahydro-[1,8]naphthyridine-3-carboxylate DDQ (159 g, 0.70 mole) was added to a stirring solution of the compound from Part C (327 g, 0.70 mol) in methylene chloride (2 L). After stirring at ambient temperature for 1 h, saturated NaHCO$_3$ (1 L) was added and the mixture stirred for 40 min. The reaction mixture was then transferred to a separatory funnel and extracted with methylene chloride. The organic layer was dried over magnesium sulfate and evaporated in vacuo and the residue (356 g) was purified by silica gel chromatography to afford title compound (124 g, 44% over the four steps): HPLC (method 1) $t_R$=2.2 min; LCMS (ESI, pos. ion spectrum) m/z 407 (M+H).

Example 2

7-[4-(4-Fluorophenyl)-5,6,7,8-tetrahydro-2-(1-methylethyl)-8-(phenylsulfonyl)-1,8-naphthyridin-3-yl]-3,5-dihydroxy-(3R,5S,6E)-6-heptenoic Acid, Monosodium Salt

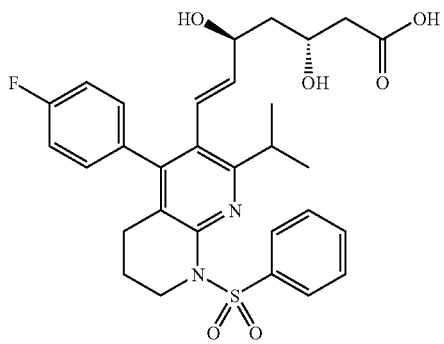

A. Methyl 4-(4-fluorophenyl)-2-(1-methylethyl)-8-(phenylsulfonyl)-5,6,7,8-tetrahydro-1,8-naphthyridine-3-carboxylate To a solution of the compound of Example 1 Part D (328 mg, 1.0 mmol) in 3 mL THF was added 1.5 mL of 1.0 M LiHMDS in THF over 1 min. After an additional 5 min, benzenesulfonyl chloride (0.17 mL, 231 mg, 1.3 mmol, 1.3 equiv) was added. After 35 min, the reaction was quenched with saturated ammonium chloride (4 mL) and water (1 mL). The aqueous solution was extracted with ethyl acetate (2×4 mL). The combined extracts were dried over magnesium sulfate and then concentrated to 438 mg of a tan solid. This residue was purified by silica gel flash chromatography using 0.3% methanol in methylene chloride to yield methyl 4-(4-fluorophenyl)-2-(1-methylethyl)-8-(phenylsulfonyl)-5,6,7,8-tetrahydro-1,8-naphthyridine-3-carboxylate (348 mg, 0.74 mmol, 74%) as an off-white foam: LC-MS (ESI, pos. ion spectrum) m/z 469 (M+H); LC method 1, $t_R$=1.89 min.

B. 7-[4-(4-Fluorophenyl)-5,6,7,8-tetrahydro-2-(1-methylethyl)-8-(phenylsulfonyl)-1,8-naphthyridin-3-yl]-3,5-dihydroxy-(3R,5S,6E)-6-heptenoic Acid, Monosodium Salt Using the procedures described in Example 1 Parts F-I, the title compound was prepared from the compound of Part A: LC-MS (ESI, pos. ion spectrum) m/z 569 (M+H); LC method 1, $t_R$=1.66 min.

Example 3

7-[4-(4-Fluorophenyl)-5,6,7,8-tetrahydro-2-(1-methylethyl)-8-[(1-methylethyl)sulfonyl]-1,8-naphthyridin-3-yl]-3,5-dihydroxy-(3R,5S,6E)-6-heptenoic Acid, Monosodium Salt

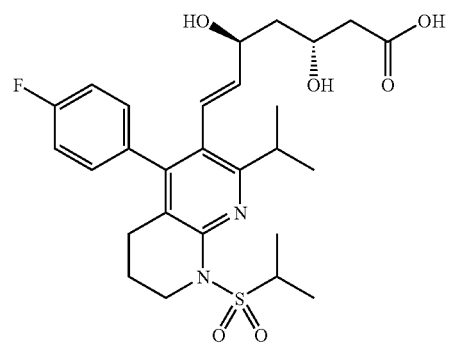

A. Methyl 8-(2-chloropropan-2-ylsulfonyl)-4-(4-fluorophenyl)-2-(1-methylethyl)-5,6,7,8-tetrahydro-1,8-naphthyridine-3-carboxylate To a solution of the compound of Example 1 Part D (328 mg, 1.0 mmol) in THF (5 mL) at 0° C. was added 1.3 mL of 1.0 M LiHMDS in THF over 30 sec. This mixture was then brought to room temperature for 5 min and recooled to 0° C. Isopropylsulfonyl chloride (0.124 mL, 157 mg, 1.1 mmol, 1.1 equiv) was added over 2 min. The reaction was brought to room temperature then quenched 65 min later with 5 mL of saturated ammonium chloride and 2 mL water. This mixture was extracted twice with ethyl acetate (10 mL, 15 mL). The combined extracts were dried with magnesium sulfate and concentrated to 407 mg of a yellow solid. This material was purified using silica gel chromatography eluting with methylene chloride to yield methyl 8-(2-chloropropan-2-ylsulfonyl)-4-(4-fluorophenyl)-2-(1-methylethyl)-5,6,7,8-tetrahydro-1,8-naphthyridine-3-carboxylate (224 mg, 0.48 mmol, 48%) as a white solid: LC-MS (ESI, pos. ion spectrum) m/z 469/471 (M+H); LC method 1, $t_R$=2.04 min.

B. Methyl 4-(4-fluorophenyl)-2-(1-methylethyl)-8-((1-methylethyl)sulfonyl)-5,6,7,8-tetrahydro-1,8-naphthyridine-3-carboxylate To a slurry of the compound of Part A (140 mg, 0.30 mmol) in 0.5 mL of tri-n-butyltin hydride were added 5 mg of AIBN and the reaction heated at 60° C. for 67 h. This material was purified directly by silica gel chromatography using 0.2% methanol in methylene chloride to give methyl 4-(4-fluorophenyl)-2-(1-methylethyl)-8-((1-methylethyl)sulfonyl)-5,6,7,8-tetrahydro-1,8-naphthyridine-3-carboxylate (90 mg, 70%): LC-MS (ESI, pos. ion spectrum) m/z 435 (M+H); LC method 1, $t_R$=1.92 min.

C. 7-[4-(4-Fluorophenyl)-5,6,7,8-tetrahydro-2-(1-methylethyl)-8-[(1-methylethyl)sulfonyl]-1,8-naphthyridin-3-yl]-3,5-dihydroxy-(3R,5S,6E)-6-heptenoic Acid, Monosodium Salt Using the procedures described in Example 1 Parts F-I the title compound was prepared from the compound of Part B: LC-MS (ESI, pos. ion spectrum) m/z 535 (M+H); LC method 1, $t_R$=1.71 min.

Example 4

7-[6-(4-Fluorophenyl)-1,2,3,5-tetrahydro-8-(1-methylethyl)-1-(methylsulfonyl)pyrido[2,3-e][1,4]oxazepin-7-yl]-3,5-dihydroxy-(3R,5S,6E)-6-heptenoic Acid, Monosodium Salt

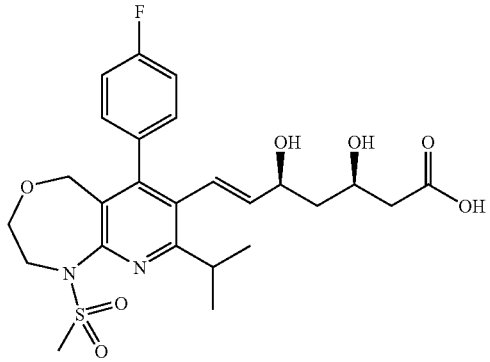

A. Dimethyl 2-fluoro-4-(4-fluorophenyl)-6-(1-methylethyl)pyridine-3,5-dicarboxylate To a solution of dimethyl 2-amino-6-(1-methylethyl)-4-phenyl-pyridine-3,5-dicarboxylate (70.0 g, 213 mmol) and 48% tetrafluoroboric acid in water (500 mL) in tetrahydrofuran (250 mL) at 0° C. was added sodium nitrite (51.5 g, 746 mmol) over 1 h. The reaction temperature was maintained between 0° C. and –5° C. After the reaction was stirred for an additional 1 h between 0° C. and –5° C. The mixture was poured into a cold solution of aqueous saturated sodium bicarbonate (1.0 L). The mixture was extracted with ethyl acetate (2×600 mL). The combined ethyl acetate layers were dried over sodium sulfate and concentrated. The crude product was dissolved in dichloromethane (50 mL) and hexane (50 mL), and was loaded onto a silica gel column (2.0 kg). The product was eluted with dichloromethane. The selected fractions were combined and concentrated to provide dimethyl 2-fluoro-4-(4-fluorophenyl)-6-(1-methylethyl)pyridine-3,5-dicarboxylate (43.00 g, 67%) as light brown oil.

B. Methyl 6-fluoro-4-(4-fluorophenyl)-5-(hydroxymethyl)-2-(1-methylethyl)nicotinate To a solution of the compound of Part A (35.0 g, 106 mmol) in dry tetrahydrofuran (200 mL) at –78° C. under nitrogen was added 1.0M lithium aluminum hydride in tetrahydrofuran (317 mL, 317 mmol). The reaction was warmed to 0° C. and was stirred at 0° C. for addition 1 h. Water (300 mL) was slowly added to the reaction mixture at –25° C. The mixture was extracted with ethyl acetate (2×300 mL). The combined ethyl acetate layers were dried over sodium sulfate and concentrated to provide methyl 6-fluoro-4-(4-fluorophenyl)-5-(hydroxymethyl)-2-(1-methylethyl)nicotinate (30 g, 93%) as brown oil.

C. Methyl 4-(4-fluorophenyl)-6-((2-hydroxyethyl)amino)-5-(hydroxymethyl)-2-(1-methylethyl)nicotinate A solution of the compound of Part B (30.00 g, 98.96 mmol), 2-aminoethanol (30.21 g, 494.8 mmol) and di(1-methylethyl)ethyl amine (34.47 mL, 197.9 mmol) in dimethylacetamide (150 mL) was heated at 120° C. for 5 h. The reaction mixture was cooled to room temperature. The mixture was diluted with ethyl acetate (300 mL) and was washed with a solution of aqueous saturated sodium bicarbonate (3×300 mL). The ethyl acetate layer was dried over sodium sulfate and concentrated to provide methyl 4-(4-fluorophenyl)-6-((2-hydroxyethyl)amino)-5-(hydroxymethyl)-2-(1-methylethyl)nicotinate (32 g, 94%) as brown gum.

D. Methyl 6-(4-fluorophenyl)-8-(1-methylethyl)-1,2,3,5-tetrahydropyrido[2,3-e][1,4]oxazepine-7-carboxylate A solution of the compound of Part C (32.00 g, 92.98 mmol) and p-toluenesulfonic acid monohydrate (17.68 g, 92.98 mmol) in toluene (500 mL) was refluxed for 6 h under a Dean-Stark trap. The reaction mixture was cooled to room temperature. The mixture was diluted with ethyl acetate (100 mL) and was washed with a solution of aqueous saturated sodium bicarbonate (2×500 mL). The organic layer was dried over sodium sulfate and concentrated. The crude product was dissolved in dichloromethane (50 mL) and was loaded onto a silica gel column. The product was eluted with 13% ethyl acetate in hexane. The product-containing fractions were combined and concentrated to provide methyl 6-(4-fluorophenyl)-8-(1-methylethyl)-1,2,3,5-tetrahydropyrido[2,3-e][1,4]oxazepine-7-carboxylate (15.4 g, 51%) as yellow solid.

E. Methyl 6-(4-fluorophenyl)-8-(1-methylethyl)-1-(methylsulfonyl)-1,2,3,5-tetrahydropyrido[2,3-e][1,4]oxazepine-7-carboxylate To a solution of the compound of Part D (15.40 g, 44.74 mmol) and pyridine (14.47 mL, 179.0 mmol) in dichloromethane (200 mL) at 0° C. under nitrogen was added a solution of methanesulfonic anhydride (15.60 g, 89.50 mmol) in dichloromethane (50 mL). The reaction mixture was stirred at room temperature for 3 days. The reaction mixture was washed with water (500 mL). The dichloromethane layer was dried over sodium sulfate and concentrated in vacuum to provide methyl 6-(4-fluorophenyl)-8-(1-methylethyl)-1-(methylsulfonyl)-1,2,3,5-tetrahydropyrido[2,3-e][1,4]oxazepine-7-carboxylate as a yellow solid.

F. (6-(4-Fluorophenyl)-8-(1-methylethyl)-1-(methylsulfonyl)-1,2,3,5-tetrahydropyrido[2,3-e][1,4]oxazepin-7-yl)methanol To a solution of the compound of Part E (17.00 g, 40.27 mmol) in dichloromethane (200 mL) at –78° C. was added 1.0 M DIBAL in dichloromethane (121 mL, 121 mmol) over 15 minutes. The reaction mixture was stirred at –78° C. for 1 h. The mixture was quenched at –78° C. with water (400 mL) and a solution of saturated Rochelle salt. The mixture was stirred at room temperature for 5 h. The mixture was extracted with dichloromethane (200 mL). The dichloromethane layer was dried over sodium sulfate and concentrated to provide (6-(4-fluorophenyl)-8-(1-methylethyl)-1-(methylsulfonyl)-1,2,3,5-tetrahydropyrido[2,3-e][1,4]oxazepin-7-yl)methanol (5.5 g, 97%) as light brown solid.

G. 6-(4-Fluorophenyl)-8-(1-methylethyl)-1-(methylsulfonyl)-1,2,3,5-tetrahydropyrido[2,3-e][1,4]oxazepine-7-carboxaldehyde To a solution of Part F (15.5 g, 39.3 mmol) in dichloromethane (250 mL) was added Dess-Martin periodinane (16.68 g, 39.32 mmol). The reaction mixture was stirred at room temperature for 2 h. The mixture diluted with dichloromethane (100 mL) and washed with a solution of aqueous saturated sodium bicarbonate (2×300 mL). The dichloromethane layer was dried over sodium sulfate and concentrated. The crude product was dissolved in dichloromethane (40 mL) and loaded onto a silica gel column (500 g). The product was eluted with 5% ethyl acetate in hexane. The product-containing fractions were combined and concentrated in vacuum to provide 6-(4-fluorophenyl)-8-(1-methylethyl)-1-(methylsulfonyl)-1,2,3,5-tetrahydropyrido[2,3-e][1,4]oxazepine-7-carboxaldehyde (14.5 g, 94%) as white solid.

H. 1,1-Dimethylethyl 2-((4R,6S)-6-((E)-2-(6-(4-fluorophenyl)-8-(1-methylethyl)-1-(methylsulfonyl)-1,2,3,5-tetrahydropyrido[2,3-e][1,4]oxazepin-7-yl)ethenyl)-2,2-dimethyl-1,3-dioxan-4-yl)acetate To a solution of the compound of Part G (14.5 g, 37.0 mmol) and 1,1-dimethylethyl(4R,6S)-2,2-dimethyl-6-(1-phenyl-1H-tetrazole-5-sulfonylmethyl)-[1,3]dioxan-4-yl-acetate (5.06 g, 44.4 mmol) in anhydrous THF (200 mL) at −78° C. under nitrogen was added 1.0 M LiHMDS in THF (44.4 mL, 44.4 mmol). The reaction mixture was stirred at −78° C. for 0.5 h. The mixture was diluted with a solution of aqueous saturated sodium bicarbonate (400 mL) and was extracted with ethyl acetate (2×300 mL). The ethyl acetate layer was dried over sodium sulfate and concentrated. The crude product was dissolved in dichloromethane (40 mL) and loaded onto a silica gel column (500 g). The product was eluted with 50% ethyl acetate in hexane. Selected product-containing fractions were combined and concentrated in vacuum to provide 1,1-dimethylethyl 2-((4R,6S)-6-((E)-2-(6-(4-fluorophenyl)-8-(1-methylethyl)-1-(methylsulfonyl)-1,2,3,5-tetrahydropyrido[2,3-e][1,4]oxazepin-7-yl)ethenyl)-2,2-dimethyl-1,3-dioxan-4-yl)acetate (19.0 g, 83%) as white solid.

I. 7-[6-(4-Fluorophenyl)-1,2,3,5-tetrahydro-8-(1-methylethyl)-1-(methylsulfonyl)pyrido[2,3-e][1,4]oxazepin-7-yl]-3,5-dihydroxy-(3R,5S,6E)-6-heptenoic Acid, Monosodium Salt To a solution of the compound of Part H (19.0 g, 30.7 mmol) in THF (500 mL) was added a solution of 6 N HCl in water (25.50 mL, 153.6 mmol). The reaction was stirred at room temperature for 2 h. A solution of aqueous 6 N NaOH (33.29 mL, 199.7 mmol) and methanol (100 mL) was added to the reaction mixture. The mixture was stirred for 2 h. The reaction was concentrated and dried under high vacuum. The crude product was dissolved in water (500 mL) and was loaded onto a C-18 column and chromatographed (Method A: Solvent A—water, solvent B—acetonitrite; flowrate-100 mL/min; Gradient—solvent A for 20 min then linear gradient from 0% B to 35% B in 30 min and then hold at 35% B for 10 min). The selected fractions were combined and concentrated. The residue was dissolved in water (400 mL) and was lyophilized to provide the title compound (15.50 g, 93%) as a white lyophilate: HPLC (method 4) $t_R$=19.8 min; LRMS (ESI, pos. ion spectrum) m/z 523 (M+H)

Example 5

7-[4-(4-Fluorophenyl)-5,6,7,8-tetrahydro-2-(1-methylethyl)-8-[(1-methyl-1H-imidazol-4-yl)sulfonyl]-1,8-naphthyridin-3-yl]-3,5-dihydroxy-(3R,5S,6E)-6-heptenoic Acid, Monosodium Salt

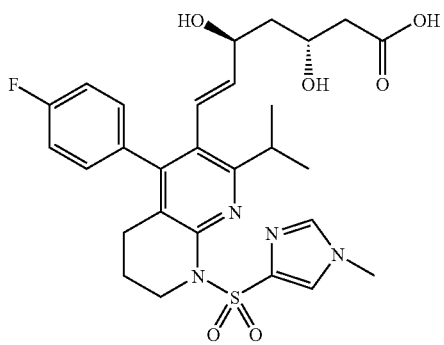

A. Methyl 4-(4-fluorophenyl)-2-(1-methylethyl)-8-(1-methyl-1H-imidazol-4-ylsulfonyl)-5,6,7,8-tetrahydro-1,8-naphthyridine-3-carboxylate To a solution of the compound of Example 1 Part D (328 mg, 1.0 mmol) in THF (3 mL) at room temperature was added 1.5 mL of 1.0 M LiHMDS/THF. After an additional 5 min 1-methyl-1H-imidazole-4-sulfonyl chloride (235 mg, 1.3 mmol, 1.3 equiv) was added. After 4 h, an additional 217 mg (1.20 mmol, 1.20 equiv) of the sulfonyl chloride was added. After an additional 16 h the reaction was quenched with saturated aqueous ammonium chloride (4 mL) plus water (1 mL) and extracted with ethyl acetate (3×5 mL). The combined organic extracts were dried over magnesium sulfate, concentrated, then purified by chromatography on basic alumina eluting with 1% methanol in methylene chloride followed by silica gel prep TLC using 2% methanol in methylene chloride. This provided methyl 4-(4-fluorophenyl)-2-(1-methylethyl)-8-(1-methyl-1H-imidazol-4-ylsulfonyl)-5,6,7,8-tetrahydro-1,8-naphthyridine-3-carboxylate (45 mg, 0.10 mmol, 10%) as a yellow oily solid: LC-MS (ESI, pos. ion spectrum) m/z 472 (M+H); LC method 1, $t_R$=1.66 min.

B. 7-[4-(4-Fluorophenyl)-5,6,7,8-tetrahydro-2-(1-methylethyl)-8-[(1-methyl-1H-imidazol-4-yl)sulfonyl]-1,8-naphthyridin-3-yl]-3,5-dihydroxy-(3R,5S,6E)-6-heptenoic Acid, Monosodium Salt Using the procedures described in Example 1 Parts F-I, the title compound was prepared from the compound of Part A: LC-MS (ESI, pos. ion spectrum) m/z 573 (M+H); LC method 1, $t_R$=1.34 min.

Example 6

7-[5-(4-Fluorophenyl)-1,4-dihydro-7-(1-methylethyl)-1-(methylsulfonyl)-2H-pyrido[2,3-d][1,3]oxazin-6-yl]-3,5-dihydroxy-(3R,5S,6E)-6-heptenoic Acid, Monosodium Salt

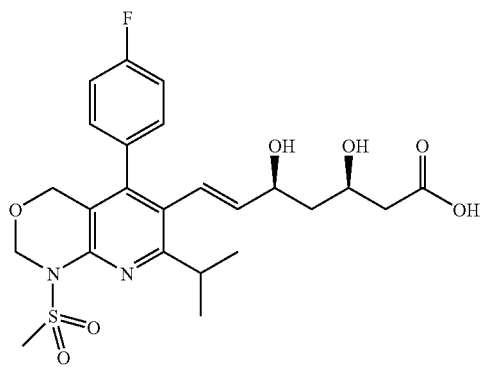

A. Dimethyl 4-(4-fluorophenyl)-2-(1-methylethyl)-6-((methylsulfonyl)amino)pyridine-3,5-dicarboxylate To a solution of the compound of Example 4 Part A (15.00 g, 42.96 mmol) and methanesulfonamide (15.70 g, 214.8 mmol) in anhydrous tetrahydrofuran (100 mL) and hexamethylphosphoramide (100 mL) at −78° C. under nitrogen was added a solution of 1.0 M LiHMDS in tetrahydrofuran (214.8 mL, 214.8 mmol), the reaction mixture warmed to room temperature and refluxed for 18 h. The mixture was cooled to room temperature and diluted with ethyl acetate (400 μL). The mixture was washed with a solution of aqueous sodium bicarbonate (3×300 mL). The ethyl acetate layer was dried over sodium sulfate and concentrated. The crude product was dissolved in dichloromethane (30 mL) and loaded onto a silica gel column (500 g). The product was eluted with 15% ethyl acetate in hexane. The selected fractions were combined and concentrated in vacuum to provide dimethyl 4-(4-fluorophenyl)-2-(1-methylethyl)-6-((methylsulfonyl)amino)pyridine-3,5-dicarboxylate (15.50 g, 85%) as white solid.

B. Methyl 4-(4-fluorophenyl)-5-(hydroxymethyl)-2-(1-methylethyl)-6-((methylsulfonyl)amino)nicotinate Using the procedure described in Example 4 part B, methyl 4-(4-fluorophenyl)-5-(hydroxymethyl)-2-(1-methylethyl)-6-((methylsulfonyl)amino)nicotinate was prepared from the compound of Part A.

C. Methyl 5-(4-fluorophenyl)-7-(1-methylethyl)-1-(methylsulfonyl)-2,4-dihydro-1H-pyrido[2,3-d][1,3]oxazine-6-carboxylate The solution of the compound from Part B (13.50 g, 34.08 mmol), p-toluenesulfonic acid monohydrate (1.29 g, 6.81 mmol) and 38% aqueous formaldehyde (25 mL) in xylene (200 mL) was heated to 125° C. in a sealed tube for 2 h. The mixture was diluted with ethyl acetate (300 mL) and washed with a solution of aqueous sodium bicarbonate (3×300 mL). The ethyl acetate layer was dried over sodium sulfate and concentrated. The crude product was dissolved in dichloromethane (30 mL) and was loaded onto a silica gel column (500 g). The product was eluted with 18% ethyl acetate in hexane. The selected fractions were combined and concentrated in vacuum to provide methyl 5-(4-fluorophenyl)-7-(1-methylethyl)-1-(methylsulfonyl)-2,4-dihydro-1H-pyrido[2,3-d][1,3]oxazine-6-carboxylate (10.9 g, 78%) as white solid.

D. 7-[5-(4-Fluorophenyl)-1,4-dihydro-7-(1-methylethyl)-1-(methylsulfonyl)-2H-pyrido[2,3-d][1,3]oxazin-6-yl]-3,5-dihydroxy-(3R,5S,6E)-6-heptenoic Acid, Monosodium Salt Using the procedures described in Example 4 Parts F-I, the title compound was prepared from the compound of Part C: LCMS (ESI, pos. ion spectrum) m/z 509 (M+H); LC method 4, $t_R$=20.6 min.

Example 7

7-[8-(Ethylsulfonyl)-4-(4-fluorophenyl)-5,6,7,8-tetrahydro-2-(1-methylethyl)-1,8-naphthyridin-3-yl]-3,5-dihydroxy-(3R,5S,6E)-6-heptenoic Acid, Monosodium Salt

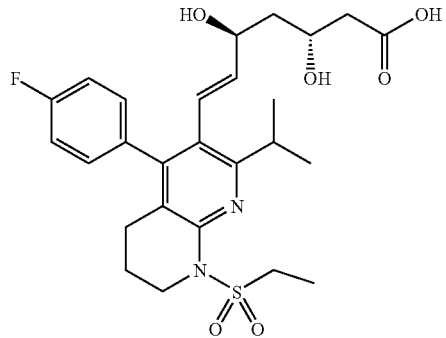

A. Methyl 8-(1-chloroethylsulfonyl)-4-(4-fluorophenyl)-2-(1-methylethyl)-5,6,7,8-tetrahydro-1,8-naphthyridine-3-carboxylate To a solution of the compound of Example 1 Part D (328 mg, 1.0 mmol) in THF (5 mL) at room temperature was added ethanesulfonyl chloride (129 mg, 1.0 mmol, 1.0 equiv). The reaction was cooled to −78° C. and then 1.0 mL of 1.0 M LiHMDS in THF was added. Additional ethanesulfonyl chloride (0.9 equiv) and LiHMDS (0.9 equiv) were later added. After 1.5 h, the reaction was quenched at −78° C. with 5 mL of saturated ammonium chloride plus 3 mL of water. The mixture was extracted with ethyl acetate (4×5 mL). The combined extracts were dried over magnesium sulfate and concentrated in vacuo. The residue was purified by silica gel chromatography eluting with 0.3% methanol in methylene chloride to provide methyl 8-(1-chloroethylsulfonyl)-4-(4-fluorophenyl)-2-(1-methylethyl)-5,6,7,8-tetrahydro-1,8-naphthyridine-3-carboxylate (310 mg, 0.68 mmol, 68%) as an off-white foam: LC-MS (ESI, pos. ion spectrum) m/z 455/457 (M+H); LC method 1, $t_R$=1.98 min.

B. Methyl 8-(ethylsulfonyl)-4-(4-fluorophenyl)-2-(1-methylethyl)-5,6,7,8-tetrahydro-1,8-naphthyridine-3-carboxylate A slurry of the compound of Part A (285 mg, 0.63 mmol), tri-n-butyltin hydride (2 mL), and AIBN (20 mg) was heated at 100° C. for 46 h. This mixture was then placed directly onto a silica gel column and eluted with 0.2% methanol in methylene chloride to yield methyl 8-(ethylsulfonyl)-4-(4-fluorophenyl)-2-(1-methylethyl)-5,6,7,8-tetrahydro-1,8-naphthyridine-3-carboxylate (114 mg, 0.27 mmol, 43%): LC-MS (ESI, pos. ion spectrum) m/z 421 (M+H); LC method 2, $t_R$=3.65 min.

C. 7-[8-(Ethylsulfonyl)-4-(4-fluorophenyl)-5,6,7,8-tetrahydro-2-(1-methylethyl)-1,8-naphthyridin-3-yl]-3,5-dihydroxy-(3R,5S,6E)-6-heptenoic Acid, Monosodium Salt Using the procedures described in Example 1 Parts F0-I, the title compound was prepared from the compound of Part A: LC-MS (ESI, pos. ion spectrum) m/z 521 (M+H); LC method 1, $t_R$=1.63 min.

Example 8

7-[4-(4-Fluorophenyl)-6,7,8,9-tetrahydro-2-(1-methylethyl)-9-(methylsulfonyl)-5H-pyrido[2,3-b]azepin-3-yl]-3,5-dihydroxy-(3R,5S,6E)-6-heptenoic Acid, Monosodium Salt

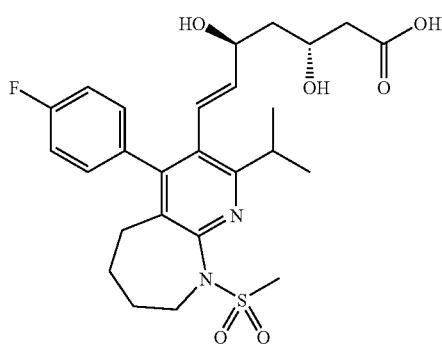

A. Methyl (E)-6-amino-5-(4-(phenylmethoxy)but-1-enyl)-4-(4-fluorophenyl)-2-(1-methylethyl)nicotinate To a suspension of (3-benzyloxypropyl)triphenyl-phosphonium bromide (8.55 g, 17.4 mmol) in tetrahydrofuran (15 mL) was added dropwise sodium bis(trimethylsilyl)amide (34.8 mL, 1.0 M in tetrahydrofuran) under nitrogen at −78° C. The reaction was stirred at −78° C. for 30 min, allowed to warm to room temperature and stirred for another 30 min. The mixture was then cooled to −78° C. and a solution of methyl 6-amino-4-(4-fluorophenyl)-5-formyl-2-(1-methylethyl)-3-pyridinecarboxylate (5.0 g, 15.8 mmol) in tetrahydrofuran (10 mL) was added dropwise over 45 min. The resulting mixture was stirred at −78° C. for 30 min, allowed to warm to room temperature and stirred for 2 h. The resulting mixture was then poured into a mixture of ice, ethyl acetate, saturated aqueous NH$_4$Cl and was extracted with ethyl acetate. The combined organic layers were washed with brine and evaporated. The residue was equally divided and portion was purified by a silica gel chromatography (120 g column), using 0% to 45% of ethyl acetate in hexanes. The collected fractions were concentrated to provide methyl (E)-6-amino-5-(4-(phenylmethoxy)but-1-enyl)-4-(4-fluorophenyl)-2-(1-methylethyl)nicotinate as a light orange oil (5.79 g, 82%): LCMS (ESI, pos. ion spectrum) m/z 449 (M+H); HPLC (method 3) $t_R$=3.2 min.

B. Methyl 6-amino-4-(4-fluorophenyl)-5-(4-hydroxybutyl)-2-(1-methylethyl)nicotinate To a solution of the compound of Part A (5.74 g, 12.8 mmol) and concentrated hydrochloric acid (3.2 mL) in methanol (150 mL) was added Pd/C (0.6 g, 10% wt. on carbon). The reaction bottle was placed under 50 psig of hydrogen. After 22 h, the mixture was filtered through a pad of Celite® and the pad was washed with methanol. The filtrates and washings were evaporated. To the residue in an ice bath was added 1N NaOH aqueous solution (40 mL). The resulting mixture was extracted with methylene chloride. The combined organic layers were washed with brine, dried (Na$_2$SO$_4$) and concentrated to give methyl 6-amino-4-(4-fluorophenyl)-5-(4-hydroxybutyl)-2-(1-methylethyl)nicotinate as a light yellow solid (2.24 g, 92%): LCMS (ESI, pos. ion spectrum) m/z 361 (M+H); HPLC (method 3) $t_R$=2.3 min.

C. Methyl 4-(4-fluorophenyl)-2-(1-methylethyl)-6-((methylsulfonyl)amino)-5-(4-(methylsulfonyloxy)butyl)nicotinate To a solution of the compound from Part B (1.9 g, 5.3 mmol) in methylene chloride (35 mL) was added pyridine (3.0 mL, 37.1 mmol) followed by addition of methanesulfonyl chloride (1.65 mL, 21.2 mmol). The reaction was stirred at room temperature for 40 min and then quenched with water (5 mL). The mixture was extracted with methylene chloride. The combined organic layers were washed with water, brine, dried (Na$_2$SO$_4$) and evaporated. The residue was purified by a silica gel chromatography, eluting with 0% to 100% of ethyl acetate in hexanes. The collected fractions were concentrated to give methyl 4-(4-fluorophenyl)-2-(1-methylethyl)-6-((methylsulfonyl)amino)-5-(4-(methylsulfonyloxy)butyl)nicotinate as a light orange solid (853 mg, 31%): LCMS (ESI, pos. ion spectrum) m/z 517 (M+H); HPLC (method 3) $t_R$=3.1 min.

D. Methyl 4-(4-fluorophenyl)-2-(1-methylethyl)-9-(methylsulfonyl)-6,7,8,9-tetrahydro-5H-pyrido[2,3-b]azepine-3-carboxylate A mixture of the compound of Part C (436 mg, 0.845 mmol) and potassium carbonate (233.5 mg, 1.69 mmol) in dimethylformamide (6.0 mL) was stirred at room temperature for 2.5 h and diluted with saturated aqueous NH$_4$Cl. The resulting mixture was extracted with ethyl acetate. The combined organic layers were washed with water, brine, dried (Na$_2$SO$_4$) and evaporated. Flash chromatography of the residue over silica gel, using 25% ethyl acetate in hexanes, gave methyl 4-(4-fluorophenyl)-2-(1-methylethyl)-9-(methylsulfonyl)-6,7,8,9-tetrahydro-5H-pyrido[2,3-b]azepine-3-carboxylate as a light yellow solid (320 mg, 90%): LCMS (ESI, pos. ion spectrum) m/z 421 (M+H); HPLC (method 3) $t_R$=3.4 min.

E. 7-[4-(4-Fluorophenyl)-6,7,8,9-tetrahydro-2-(1-methylethyl)-9-(methylsulfonyl)-5H-pyrido[2,3-b]azepin-3-yl]-3,5-dihydroxy-(3R,5S,6E)-6-heptenoic Acid, Monosodium Salt Using the procedures described in Example 1 Part F-I the title compound was prepared from the compound of Part D: LCMS (ESI, pos. ion spectrum) m/z 521 (M+H); HPLC (method 3) $t_R$=3.0 min.

Example 9

7-[4-(4-Fluorophenyl)-5,6,7,8-tetrahydro-2-(1-methylethyl)-1,8-naphthyridin-3-yl]-3,5-dihydroxy-(3R,5S,6E)-6-heptenoic Acid, Monosodium Salt

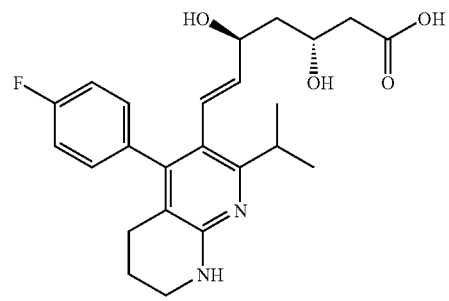

A. (4-(4-Fluorophenyl)-2-(1-methylethyl)-5,6,7,8-tetrahydro-1,8-naphthyridin-3-yl)methanol To a solution of the compound of Example 1 Part D (3.88 g, 11.8 mmol) in 100 mL of toluene at −78° C. was added 23.6 mL of 1.5 M DIBAL in toluene over 15 min. Over the course of the next 3-4 h, the reaction temperature was allowed to rise to −25° C. The reaction was cooled to −78° C. and quenched with 100 mL of saturated ammonium chloride plus 50 mL water. Ethyl acetate was added. An emulsion formed which was broken by passing the mixture through a 3 cm pad of Celite® (~5 cm diameter). The pad was rinsed with additional ethyl acetate (200 mL) and water (100 mL). The layers of the combined filtrates were separated. The aqueous layer was extracted with an additional 200 mL of ethyl acetate. The combined organic extracts were dried over magnesium sulfate and then concentrated. The residue was purified by silica gel chromatography using 1% methanol in methylene chloride to yield (4-(4-fluorophenyl)-2-(1-methylethyl)-5,6,7,8-tetrahydro-1,8-naphthyridin-3-yl)methanol (3.1 g, 88%): LC-MS (ESI, pos. ion spectrum) m/z 301 (M+H); LC method 1, $t_R$=1.21 min.

B. 2-(Trimethylsilyl)ethyl 5-(4-fluorophenyl)-6-(hydroxymethyl)-7-(1-methylethyl)-3,4-dihydro-1,8-naphthyridine-1(2H)-carboxylate To a solution of the compound of Part A (3.1 g, 10.3 mmol) in THF (20 mL) were added triethylamine (2.09 g, 20.7 mmol, 2.0 equiv) and 4-nitrophenyl 2-(trimethylsilyl)ethyl carbonate (4.09 g, 14.5 mmol, 1.4 equiv). The reaction was heated at 70° C. for 6 h, cooled to room temperature, and mixed with ethyl acetate (100 mL). This mixture was then washed successively with 2×100 mL each of saturated ammonium chloride then saturated sodium bicarbonate, followed by drying with magnesium sulfate and concentration. Purification by silica gel chromatography eluting with 0.5% methanol in methylene chloride gave 2-(trimethylsilyl)ethyl 5-(4-fluorophenyl)-6-(hydroxymethyl)-7-(1-methylethyl)-3,4-dihydro-1,8-naphthyridine-1(2H)-carboxylate (3.56 g, 8.0 mmol, 78%) as an off-white foam: LC-MS (ESI, pos. ion spectrum) m/z 445 (M+H); LC method 1, $t_R$=1.69 min.

C. 2-(Trimethylsilyl)ethyl 5-(4-fluorophenyl)-6-formyl-7-(1-methylethyl)-3,4-dihydro-1,8-naphthyridine-[(2H)-carboxylate 2-(trimethylsilyl)ethyl 5-(4-fluorophenyl)-6-formyl-7-(1-methylethyl)-3,4-dihydro-1,8-naphthyridine-[(2H)-carboxylate was prepared from the compound of Part B using the procedure described in Example 1 Part G. The crude product was purified by silica gel chromatography eluting with 5% ethyl acetate in hexane. From the compound of Part B (3.53 g, 7.95 mmol) was obtained 2-(trimethylsilyl)ethyl 5-(4-fluorophenyl)-6-formyl-7-(1-methylethyl)-3,4-dihydro-1,8-naphthyridine-1 (2H)-carboxylate (2.21 g, 63%) as a nearly colorless oil which crystallized upon cooling: LC-MS (ESI, pos. ion spectrum) m/z 443 (M+H); LC method 1, $t_R$=1.97 min.

D. 2-(Trimethylsilyl)ethyl 6-((E)-2-((4S,6R)-6-(1,1-dimethylethoxy-2-oxoethyl)-2,2-dimethyl-1,3-dioxan-4-yl)ethenyl)-5-(4-fluorophenyl)-7-(1-methylethyl)-3,4-dihydro-1,8-naphthyridine-1(2H)-carboxylate 2-(Trimethylsilyl)ethyl 6-((E)-2-((4S,6R)-6-(1,1-dimethylethoxy-2-oxoethyl)-2,2-dimethyl-1,3-dioxan-4-yl)ethenyl)-5-(4-fluorophenyl)-7-(1-methylethyl)-3,4-dihydro-1,8-naphthyridine-[(2H)-carboxylate was prepared from the compound of Part C using the procedure described in Example 1 Part H: LC-MS (ESI, pos. ion spectrum) m/z 669 (M+H); LC method 1, $t_R$=2.03 min.

E. 1,1-Dimethylethyl 2-((4R,6S)-6-((E)-2-(4-(4-fluorophenyl)-2-(1-methylethyl)-5,6,7,8-tetrahydro-1,8-naphthyridin-3-yl)ethenyl)-2,2-dimethyl-1,3-dioxan-4-yl)acetate To a solution of the compound of Part D (120 mg, 0.18 mmol) in THF (1 mL) was added 0.54 mL of 1.0 M TBAF/THF. After 3 h, the reaction was quenched with saturated ammonium chloride (3 mL) and extracted with ethyl acetate (4 mL). The ethyl acetate layer was backwashed with saturated ammonium chloride (3 mL) and then water (3 mL), dried over magnesium sulfate and concentrated in vacuo. The residue was purified by passage through a 2 gram column of reverse phase C-18 silica gel eluting with 0 to 100% methanol in water. This provided 1,1-dimethylethyl 2-((4R,6S)-6-((E)-2-(4-(4-fluorophenyl)-2-(1-methylethyl)-5,6,7,8-tetrahydro-1,8-naphthyridin-3-yl)ethenyl)-2,2-dimethyl-1,3-dioxan-4-yl)acetate (59 mg, 0.111 mmol, 63%) as an off-white solid: LC-MS (ESI, pos. ion spectrum) m/z 525 (M+H); LC method 1, $t_R$=1.89 min.

F. 7-[4-(4-Fluorophenyl)-5,6,7,8-tetrahydro-2-(1-methylethyl)-1,8-naphthyridin-3-yl]-3,5-dihydroxy-(3R,5S,6E)-6-heptenoic Acid, Monosodium Salt The title compound was prepared from the compound of Part E using the procedure described in Example 1 Part I: LC-MS (ESI, pos. ion spectrum) m/z 429 (M+H); LC method 1, $t_R$=1.19 min.

Example 10

7-[8-Acetyl-4-(4-fluorophenyl)-5,6,7,8-tetrahydro-2-(1-methylethyl)-1,8-naphthyridin-3-yl]-3,5-dihydroxy-(3R,5S,6E)-6-heptenoic Acid, Monosodium Salt

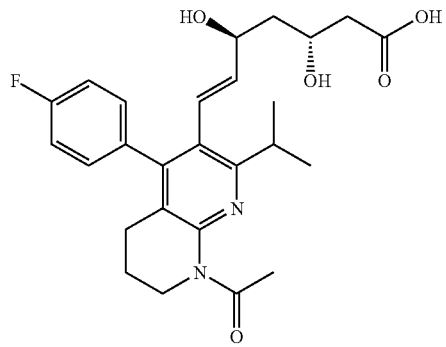

A. 1,1-Dimethylethyl 2-((4R,6S)-6-((E)-2-(8-acetyl-4-(4-fluorophenyl)-2-(1-methylethyl)-5,6,7,8-tetrahydro-1,8-naphthyridin-3-yl)ethenyl)-2,2-dimethyl-1,3-dioxan-4-yl)acetate The compound of Example 9 Part E (255 mg, 0.49 mmol) was dissolved in 2 mL of acetic anhydride and the mixture heated at 78° C. for 35 min. The excess acetic anhydride was removed in vacuo and the residue purified by silica gel chromatography eluting with 0.5% methanol in methylene chloride to give 1,1-dimethylethyl 2-((4R,6S)-6-((E)-2-(8-acetyl-4-(4-fluorophenyl)-2-(1-methylethyl)-5,6,7,8-tetrahydro-1,8-naphthyridin-3-yl)ethenyl)-2,2-dimethyl-1,3-dioxan-4-yl)acetate (258 mg, 0.46 mmol, 93%) as a tan solid: LC-MS (ESI, pos. ion spectrum) m/z 567 (M+H); LC method 1, $t_R$=1.98 min.

B. 7-[8-Acetyl-4-(4-fluorophenyl)-5,6,7,8-tetrahydro-2-(1-methylethyl)-1,8-naphthyridin-3-yl]-3,5-dihydroxy-(3R,5S,6E)-6-heptenoic Acid, Monosodium Salt The title compound was prepared from the compound of Part A using the procedure described in Example 1 Part I: LC-MS (ESI, pos. ion spectrum) m/z 471 (M+H); LC method 1, $t_R$=0.10 min.

Example 11

7-[5-(4-Fluorophenyl)-3,4-dihydro-1-methyl-7-(1-methylethyl)-2,2-dioxido-1H-pyrido[2,3-c][1,2]thiazin-6-yl]-3,5-dihydroxy-(3R,5S,6E)-6-heptenoic Acid, Monosodium Salt

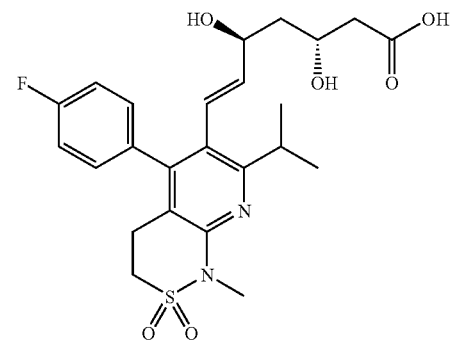

A. 3-Ethyl 5-methyl 4-(4-fluorophenyl)-6-(1-methylethyl)-2-(bis(methylsulfonyl)amino)pyridine-3,5-dicarboxylate To a solution of 3-ethyl 5-methyl 2-amino-4-(4-fluorophenyl)-6-(1-methylethyl)-3,5-pyridinedicarboxylic acid (9.0 g, 25.0 mmol) in methylene chloride (200 mL) at −78° C. was added triethylamine (20.9 mL, 150.0 mmol) followed by addition of methanesulfonyl chloride (8.47 mL, 113 mmol). The reaction was stirred at −78° C. for 5 h and then quenched with water. The mixture was extracted with methylene chloride. The combined organic layers were washed with water, brine, dried (Na$_2$SO$_4$) and evaporated. The residue was purified with a silica gel column (330 g, 1% to 50% of ethyl acetate in hexanes). The collected fractions were concentrated to give 3-ethyl 5-methyl 4-(4-fluorophenyl)-6-(1-methylethyl)-2-(bis(methylsulfonyl)amino)pyridine-3,5-dicarboxylate as a white solid (9.11 g, 78%): LCMS (ESI, pos. ion spectrum) m/z 517 (M+H); HPLC (method 3) $t_R$=3.4 min.

B. 3-Ethyl 5-methyl 4-(4-fluorophenyl)-6-(1-methylethyl)-2-((methylsulfonyl)amino)pyridine-3,5-dicarboxylate To a solution of the compound of Part A (530 mg, 1.03 mmol) in methanol (5 mL) was added sodium ethoxide (73.3 mg, 1.08 mmol). After 15 min, the reaction was quenched with saturated aqueous NH₄Cl. The resulting mixture was extracted with ethyl acetate. The combined organic layers were washed with water, brine, dried (Na₂SO₄) and concentrated in vacuo to give 3-ethyl 5-methyl 4-(4-fluorophenyl)-6-(1-methylethyl)-2-((methylsulfonyl)amino)pyridine-3,5-dicarboxylate as a white solid (440 mg, 98%): LCMS (ESI, pos. ion spectrum) m/z 439 (M+H); HPLC (method 3) $t_R$=3.4 min.

C. 3-Ethyl 5-methyl 4-(4-fluorophenyl)-6-(1-methylethyl)-2-((methylsulfonyl)methylamino)pyridine-3,5-dicarboxylate To a solution of the compound of Part B (8.18 g, 18.7 mmol) in dimethylformamide (100 mL) was added potassium carbonate (5.16 g, 37.4 mmol) and methyl iodide (1.51 mL, 24.3 mmol). The reaction was stirred at room temperature for 5 h and then diluted with water (175 mL). The resulting mixture was extracted with ethyl acetate (3×200 mL). The combined organic extracts were washed with water, brine, dried (Na₂SO₄) and concentrated in vacuo to provide 3-ethyl 5-methyl 4-(4-fluorophenyl)-6-(1-methylethyl)-2-((methylsulfonyl)methylamino)pyridine-3,5-dicarboxylate as a white solid (7.75 g, 92%): LCMS (ESI, pos. ion spectrum) m/z 453 (M+H); HPLC (method 3) $t_R$=3.3 min.

D. Methyl 2,2-dioxido-3,4-dihydro-5-(4-fluorophenyl)-1-methyl-7-(1-methylethyl)-4-oxo-1H-pyrido[2,3-c][1,2]thiazine-6-carboxylate To a solution of the compound from Part C (7.72 g, 17.1 mmol) in dimethylformamide (100 m]L) was added sodium hydride (0.95 g, 38 mmol) in one portion. The resulting suspension was stirred at room temperature for 5.5 h and more sodium hydride (0.22 g, 9.2 mmol) was added. The mixture was stirred for another 40 min, quenched with methanol (25 mL) at 0° C. and then diluted with water (175 mL). The resulting mixture was extracted with ethyl acetate. The combined organic layers were washed with saturated aqueous NH₄Cl, dried (Na₂SO₄) and passed through a pad of silica. The filtrates and washings were evaporated to yield methyl 2,2-dioxido-3,4-dihydro-5-(4-fluorophenyl)-1-methyl-7-(1-methylethyl)-4-oxo-1H-pyrido[2,3-c][1,2]thiazine-6-carboxylate as a pale orange solid (6.52 g, 94%): LCMS (ESI, pos. ion spectrum) m/z 407 (M+H); HPLC (method 3) $t_R$=3.4 min.

E. Methyl 2,2-dioxido-3,4-dihydro-5-(4-fluorophenyl)-1-methyl-7-(1-methylethyl)-4-hydroxy-1H-pyrido[2,3-c][1,2]thiazine-6-carboxylate To a suspension of the compound of Part D (6.43 g, 15.84 mmol) in methanol (120 mL) at 0° C. under nitrogen was added sodium borohydride (1.2 g, 32 mmol) in several portions. The resulting mixture was stirred at 0° C. for 40 min, quenched with saturated aqueous NH₄Cl (125 mL) and passed through a Celite® pad. The filtrates were extracted with ethyl acetate. The combined organic layers were washed with brine, dried (Na₂SO₄), passed through a pad of silica and evaporated. The residue was dissolved in methylene chloride, filtered and concentrated in vacuo to give methyl 2,2-dioxido-3,4-dihydro-5-(4-fluorophenyl)-1-methyl-7-(1-methylethyl)-4-hydroxy-1H-pyrido[2,3-c][1,2]thiazine-6-carboxylate as a off-white solid (6.82 g, quantitative): LCMS (ESI, pos. ion spectrum) m/z 409 (M+H); HPLC (method 3) $t_R$=3.3 min.

F. Methyl 2,2-dioxido-5-(4-fluorophenyl)-1-methyl-7-(1-methylethyl)-1H-pyrido[2,3-c][1,2]thiazine-6-carboxylate To a mixture of the compound of Part E (6.43 g, 15.8 mmol) and triethylamine (9.9 mL, 71 mmol) in methylene chloride (150 mL) at 0° C. was added dropwise methanesulfonyl chloride (3.06 mL, 39.4 mmol) over 4 min. The reaction was stirred at 0° C. for 5 min, at room temperature for 30 min and then quenched with methanol (30 mL) at 0° C. The resulting mixture was diluted with methylene chloride (200 mL) and then washed with water, brine, dried (Na₂SO₄) and passed through a pad of silica. The filtrate was concentrated in vacuo to provide methyl 2,2-dioxido-5-(4-fluorophenyl)-1-methyl-7-(1-methylethyl)-1H-pyrido[2,3-c][1,2]thiazine-6-carboxylate as a light yellow solid (5.89 g, 96%): LCMS (ESI, pos. ion spectrum) m/z 391 (M+H); HPLC (method 3) $t_R$=3.6 min.

G. Methyl 2,2-dioxido-3,4-dihydro-5-(4-fluorophenyl)-1-methyl-7-(1-methylethyl)-1H-pyrido[2,3-c][1,2]thiazine-6-carboxylate A solution of the compound of Part F (5.6 g, 14 mmol) and trifluroroacetic acid (3.32 mL, 43.1 mmol) in ethyl acetate (150 mL) was added to a reaction bottle containing Pd/C (2.8 g, 10 wt. % on carbon). The bottle was placed under 50 psig of hydrogen. After 20 h, more Pd/C (2.8 g, 10 wt. % on carbon) and trifluroroacetic acid (3.8 mL) were added. The mixture was continually stirred under hydrogen for 1.5 h. The resulting mixture was filtered through a Celite® pad and the filtrate was evaporated. The residue was dissolved in methylene chloride, filtered through a pad of silica and concentrated in vacuo to provide methyl 2,2-dioxido-3,4-dihydro-5-(4-fluorophenyl)-1-methyl-7-(1-methylethyl)-1H-pyrido[2,3-c][1,2]thiazine-6-carboxylate as a light yellow solid (5.64 g, 100%): LCMS (ESI, pos. ion spectrum) m/z 393 (M+H); HPLC (method 3) $t_R$=3.5 min.

H. 7-[5-(4-Fluorophenyl)-3,4-dihydro-1-methyl-7-(1-methylethyl)-2,2-dioxido-1H-pyrido[2,3-c][1,2]thiazin-6-yl]-3,5-dihydroxy-(3R,5S,6E)-6-heptenoic Acid, Monosodium Salt Using the procedures described in Example 1 Parts F-I, the title compound was prepared from the compound of part G: LCMS (ESI, pos. ion spectrum) m/z 493 (M+H); HPLC (method 3) $t_R$=3.0 min.

Example 12

7-[4-(4-Fluorophenyl)-2,3-dihydro-6-(1-methylethyl)-1-(methylsulfonyl)-1H-pyrrolo[2,3-b]pyridin-5-yl]-3,5-dihydroxy-(3R,5S,6E)-6-heptenoic Acid, Monosodium Salt

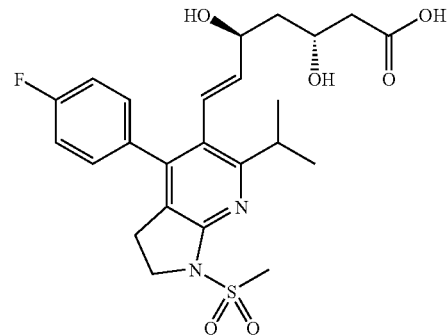

A. Methyl 6-amino-4-(4-fluorophenyl)-2-(1-methylethyl)-5-(2-methoxyethenyl)nicotinate To a suspension of (methoxymethyl)triphenyl-phosphonium chloride (260 mg, 0.75 mmol) in tetrahydrofuran (0.3 mL) was added, dropwise, a solution of potassium tert-butoxide (0.75 mL, 1.0 M in tetrahydrofuran). After 15 min, a solution of methyl 6-amino-4-(4-fluorophenyl)-5-formyl-2-(1-methylethyl)-3-pyridinecarboxylate (95 mg, 0.3 mmol) in tetrahydrofuran (0.3 mL) was added to the above mixture. The resulting mixture was stirred at room temperature for 2.5 h, diluted with ethyl acetate (15 mL) and washed with brine, dried ($Na_2SO_4$) and evaporated. The residue was purified by a silica gel chromatography (45 g column), eluting with 15% to 20% of ethyl acetate in hexanes to provide methyl 6-amino-4-(4-fluorophenyl)-2-(1-methylethyl)-5-(2-methoxyethenyl)nicotinate as a E/Z mixture (80 mg, 77%): LCMS (ESI, pos. ion spectrum) m/z 345 (M+H); HPLC (method 3) $t_R$=2.4 min.

B. Methyl 4-(4-fluorophenyl)-6-(1-methylethyl)-1H-pyrrolo[2,3-b]pyridine-5-carboxylate To a suspension of the compound of Part A (2.1 g, 6.1 mmol) in tetrahydrofuran (2.0 mL) was added concentrated hydrochloric acid (2.03 mL). Additional tetrahydrofuran (0.5 mL) was added after 20 min. At 2.5 h, the mixture was diluted with ethyl acetate (40 mL) and neutralized with saturated aqueous $NaHCO_3$ (35 mL). The resulting layers were separated and the aqueous layer was extracted with ethyl acetate. The combined organic extracts were washed with brine, dried ($Na_2SO_4$) and concentrated to give methyl 4-(4-fluorophenyl)-6-(1-methylethyl)-1H-pyrrolo[2,3-b]pyridine-5-carboxylate as a light brown solid (1.93 g, quantitative): LCMS (ESI, pos. ion spectrum) m/z 313 (M+H); HPLC (method 3) $t_R$=3.4 min.

C. Methyl 4-(4-fluorophenyl)-6-(1-methylethyl)-2,3-dihydro-1H-pyrrolo[2,3-b]pyridine-5-carboxylate A solution of the compound of Part B (21.0 g, 67.3 mmol) and concentrated hydrochloric acid (17.0 mL) was added to a reaction bottle containing palladium hydroxide (22 g, 20 wt. % Pd on carbon). The bottle was placed under 50 psig of hydrogen. After 3 days, more concentrated hydrochloric acid (2.5 mL) was added. At 4 days, the mixture was filtered through a pad of Celite® and the filtrate was concentrated to give a pale yellow solid. The solid was dissolved in methylene chloride and then water was added. To the mixture was added sodium bicarbonate solid to neutralize the acid. The organic layer was washed with brine, passed through a pad of silica and the pad was washed with 10% methanol in methylene chloride and 100% methanol. The collected filtrates and washings were concentrated to give methyl 4-(4-fluorophenyl)-6-(1-methylethyl)-2,3-dihydro-1H-pyrrolo[2,3-b]pyridine-5-carboxylate as an off-white solid (21 g, 99%): LCMS (ESI, pos. ion spectrum) m/z 315 (M+H); HPLC (method 3) $t_R$=2.3 min.

D. Methyl 4-(4-fluorophenyl)-6-(1-methylethyl)-1-(methylsulfonyl)-2,3-dihydro-1H-pyrrolo[2,3-b]pyridine-5-carboxylate To a solution of the compound of Part C (108 mg, 0.34 mmol) in chloroform (8 mL) was added pyridine (0.139 mL, 1.72 mmol) followed by addition of methanesulfonic anhydride (150 mg, 0.86 mmol). The reaction was stirred for 3 h and then quenched with water at 0° C. The mixture was extracted with methylene chloride. The combined organic layers were washed with water, brine, dried and passed through a pad of Celite®. The pad was washed with 1% methanol in methylene chloride. The combined filtrates and washings were concentrated. The residue was purified by a silica gel chromatography (40 g column), eluting with 0.5% methanol in methylene chloride. The collected fractions were concentrated in vacuo to give methyl 4-(4-fluorophenyl)-6-(1-methylethyl)-1-(methylsulfonyl)-2,3-dihydro-1H-pyrrolo[2,3-b]pyridine-5-carboxylate as a glassy material (114 mg, 84%): LCMS (ESI, pos. ion spectrum) m/z 393 (M+H); HPLC (method 3) $t_R$=3.3 min.

E. 7-[4-(4-Fluorophenyl)-2,3-dihydro-6-(1-methylethyl)-1-(methylsulfonyl)-1H-pyrrolo[2,3-b]pyridin-5-yl]-3,5-dihydroxy-(3R,5S,6E)-6-heptenoic Acid, Monosodium Salt Using the procedures described in Example 1 Parts F-I, the title compound was prepared from the compound of Part D: LCMS (ESI, pos. ion spectrum) m/z 493 (M+H); HPLC (method 3) $t_R$=2.8 min.

Example 13

7-[(3R)-6-(4-Fluorophenyl)-1,2,3,5-tetrahydro-3-methyl-8-(1-methylethyl)-1-(methylsulfonyl)pyrido[2,3-e][1,4]oxazepin-7-yl]-3,5-dihydroxy-(3R,5S,6E)-6-heptenoic Acid, Monosodium Salt

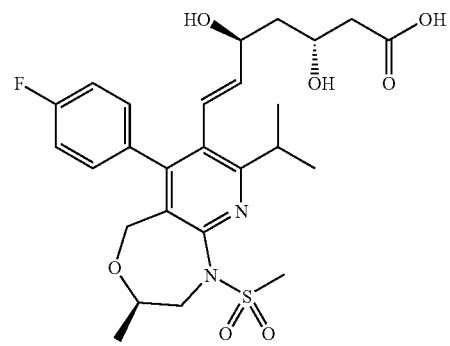

The title compound was prepared using the procedure described for Example 4: HPLC (method 4) $t_R$=21.3 min; LRMS (ESI, pos ion spectrum) m/z 537 (M+H).

Example 14

7-[4-(4-Fluorophenyl)-5,6,7,8-tetrahydro-8-methyl-2-(1-methylethyl)-1,8-naphthyridin-3-yl]-3,5-dihydroxy-(3R,5S,6E)-6-heptenoic Acid, Monosodium Salt

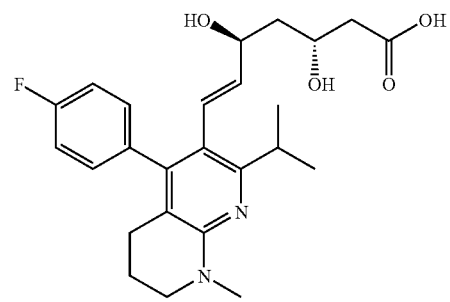

A. 1,1-Dimethylethyl 2-((4R,6S)-6-((E)-2-(4-(4-fluorophenyl)-2-(1-methylethyl)-8-methyl-5,6,7,8-tetrahydro-1,8-naphthyridin-3-yl)ethenyl)-2,2-dimethyl-1,3-dioxan-4-yl)acetate To a solution of the compound of Example 9 Part E (207 mg, 0.40 mmol) in THF (1 mL) at −78° C. were added 0.88 mL of 1.0 M LiHMDS/THF (0.88 mmol, 2.2 equiv) and methyl iodide (136 mg, 0.96 mmol, 2.4 equiv) in sequence. The reaction mixture was warmed to room temperature. After 14 h at room temperature the reaction was quenched with saturated aqueous sodium bicarbonate (1 mL) and extracted with ethyl acetate (2 mL). The ethyl acetate layer was washed with water (1 mL), dried with magnesium sulfate and concentrated. The residue was purified by silica gel chromatography eluting with 0.3% methanol in methylene chloride to provide 1,1-dimethylethyl 2-((4R,6S)-6-((E)-2-(4-(4-fluorophenyl)-2-(1-methylethyl)-8-methyl-5,6,7,8-tetrahydro-1,8-naphthyridin-3-yl)ethenyl)-2,2-dimethyl-1,3-dioxan-4-yl) acetate (75 mg, 0.14 mmol, 35%) as a yellow/orange foam: LC-MS (ESI, pos. ion spectrum) m/z 539 (M+H); LC method 1, $t_R$=1.87 min.

B. 7-[4-(4-Fluorophenyl)-5,6,7,8-tetrahydro-8-methyl-2-(1-methylethyl)-1,8-naphthyridin-3-yl]-3,5-dihydroxy-(3R,5S,6E)-6-heptenoic Acid, Monosodium Salt The title compound was prepared from the compound of Part A using the procedure described in Example 1 Part I: LC-MS (ESI, pos. ion spectrum) m/z 443 (M+H); LC method 1, $t_R$=1.14 min.

Example 15

7-[(2R)-6-(4-Fluorophenyl)-1,2,3,5-tetrahydro-2-methyl-8-(1-methylethyl)-1-(methylsulfonyl)pyrido [2,3-e][1,4]oxazepin-7-yl]-3,5-dihydroxy-(3R,5S,6E)-6-heptenoic Acid, Monosodium Salt

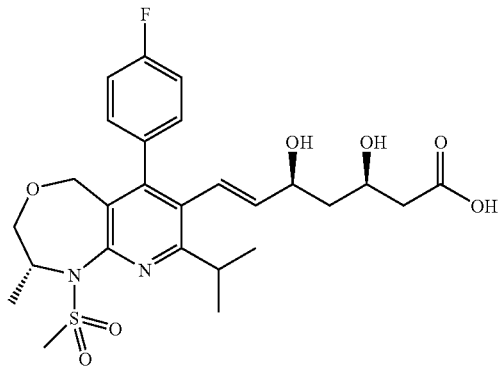

The title compound was prepared using the procedure described for Example 4: HPLC (method 4) $t_R$=20.8 min; LRMS (ESI, pos. ion spectrum) m/z 537 (M+H).

Example 16

7-[4-(4-Fluorophenyl)-6,7,8,9-tetrahydro-9-methyl-2-(1-methylethyl)-8-oxo-5H-pyrido[2,3-b]azepin-3-yl]-3,5-dihydroxy-(3R,5S,6E)-6-heptenoic Acid, Monosodium Salt

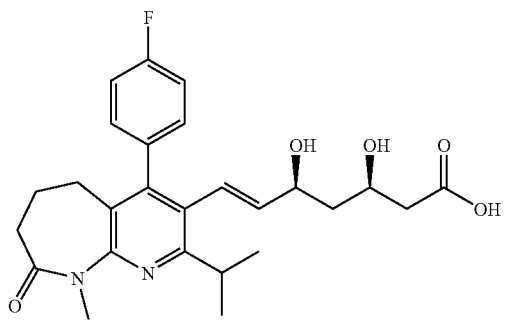

A. Methyl 4-(4-fluorophenyl)-2-(1-methylethyl)-5,6,7,8-tetrahydroquinoline-3-carboxylate A NaHMDS solution in THF (112 mL, 1.0 M) was diluted with 50 mL of dry THF and cooled to −78° C. A solution of cyclohexanone (10.6 mL, 102 mmol) in 50 mL of dry THF was added dropwise over 10 min. After the addition, the mixture was allowed to warm to room temperature and stirred at 0° C. for 15 min before it was cooled to −78° C. again. A pre-cooled solution of methyl 2-[(4-fluorophenyl)methylene]-4-methyl-3-oxo-pentanoic acid (30.7 g, 123 mmol) in 30 mL of dry THF at −78° C. was added quickly via a cannula. The reaction mixture was stirred at −78° C. for 3 h and quenched with acetic acid (30 mL, 524 mmol) in 30 mL of THF. After warming to room temperature the reaction was diluted with 50 mL of water and extracted with ethyl acetate (3×100 mL). The organic fractions were combined, washed with saturated aqueous sodium chloride solution (100 mL), dried over magnesium sulfate, filtered and concentrated in vacuum to provide methyl 4-fluoro-α-(1-oxo-2-methylpropyl)-β-(2-oxocyclohexyl)benzenepropanoate a pale yellow oil: LCMS (method 5) $t_R$=2.1 min; (ESI, pos. ion spectrum) m/z 349 (M+H).

To a solution of the preceding compound in 200 mL of absolute ethanol was added ammonium acetate (65.4 g, 816 mmol) and p-toluenesulfonic acid monohydrate (970 mg, 5 mmol). The reaction was refluxed for 14 h and the solvent was evaporated to dryness in vacuo. The white residue was dissolved in 100 mL of methylene chloride and filtered. The filtrate was concentrated to afford methyl 4-(4-fluorophenyl)-2-(1-methylethyl)-4,4a,5,6,7,8-hexahydroquinoline-3-carboxylate (and/or its double bond isomers) as a yellow oil: LCMS (method 5) $t_R$=2.1 min; (ESI, pos. ion spectrum) m/z 330 (M+H).

To a solution of the preceding compound in methylene chloride (150 mL) at 0° C. was added 2,3-dichloro-5,6-dicyano-1,4-benzoquinone (26.4 g, 116 mmol). The reaction was stirred for 2 h at room temperature and diluted with 100 mL dichloromethane. The mixture was washed with saturated aqueous sodium bicarbonate solution (3×100 mL). The organic layer was dried over magnesium sulfate, filtered and concentrated in vacuum. Flash chromatography of the residue on a silica gel column with 5% of ethyl acetate/hexanes as the eluant gave 30.8 g (92% yield) of methyl 4-(4-fluorophenyl)-2-(1-methylethyl)-5,6,7,8-tetrahydroquinoline-3-carboxylate: HPLC (method 6) $t_R$=3.3 min; LRMS (ESI, pos. ion spectrum) m/z 328 (M+H).

B. [4-(4-Fluorophenyl)-2-(1-methylethyl)-5,6,7,8-tetrahydroquinolin-3-yl]methanol To a solution of the compound of Part A (31 g, 94 mmol) in 300 mL of dry methylene chloride at 0° C. was added diisobutylaluminum hydride in methylene chloride (1 N, 217 mL, 217 mmol) dropwise. The reaction was stirred for 1 h at 0° C. and was quenched by the dropwise addition of methanol at −78° C. until no more gas evolved. The mixture was diluted with 300 mL of 25% aqueous solution of potassium sodium tartrate and was stirred at room temperature overnight. The organic layer was separated and dried over magnesium sulfate, filtered and concentrated to afford the crude product. Flash chromatography on a silica gel column with 20% ethyl acetate/hexanes as the eluant provided 25 g (89% yield) of [4-(4-fluorophenyl)-2-(1-methylethyl)-5,6,7,8-tetrahydroquinolin-3-yl]methanol: HPLC (method 6) $t_R$=2.45 min; LRMS (ESI, pos. ion spectrum) m/z 300 (M+H).

C. (8-Benzylidene-4-(4-fluorophenyl)-2-(1-methylethyl)-5,6,7,8-tetrahydroquinolin-3-yl)methyl Acetate A mixture of the compound of Part B (23.4 g, 78.3 mmol), benzaldehyde (11.9 mL, 117 mmol) and acetic anhydride (37 mL, 391.5 mmol) was heated to reflux (170° C.) under nitrogen for 13 h. The solvent was then removed in vacuo. The residue was recrystallized from 50 mL of hot ethanol to afford 27.5 g of (8-benzylidene-4-(4-fluorophenyl)-2-(1-methylethyl)-5,6,7,8-tetrahydroquinolin-3-yl)methyl acetate. The mother liquor was concentrated and the residue was chromatographed on a silica gel column with 5% of ethyl acetate/hexanes as the eluent to afford an additional 4.5 g of (8-benzylidene-4-(4-fluorophenyl)-2-(1-methylethyl)-5,6,7,8-tetrahydroquinolin-3-yl)methyl acetate (combined 95% yield): LCMS (method 5) $t_R$=2.3 min; (ESI, pos. ion spectrum) m/z 430 (M+H).

D. (4-(4-Fluorophenyl)-2-(1-methylethyl)-8-oxo-5,6,7,8-tetrahydroquinolin-3-yl)methyl Acetate Ozone was passed through a solution of the compound of Part C (32 g, 74.6 mmol) in 200 mL of methylene chloride at −78° C. until the blue-purple color persisted. Nitrogen was then passed through the reaction to remove the excess ozone. Dimethyl sulfide (10 mL) was added and the reaction was warmed to room temperature and stirred overnight. The mixture was concentrated and the residue was chromatographed on a silica gel column with 20-50% ethyl acetate/hexanes as the eluent to afford 21.6 g (82% yield) of (4-(4-fluorophenyl)-2-(1-methylethyl)-8-oxo-5,6,7,8-tetrahydroquinolin-3-yl) methyl acetate: HPLC (method 6) $t_R$=3.59 min; LRMS (ESI, pos. ion spectrum): m/z 300 (M+H).

E. (E)-(4-(4-Fluorophenyl)-8-(hydroxyimino)-2-(1-methylethyl)-5,6,7,8-tetrahydroquinolin-3-yl)methyl Acetate To a solution of the compound of Part D (21.6 g, 60.8 mmol) in 50 mL of absolute ethanol was added pyridine (50 mL) and hydroxylamine hydrochloride (12.6 g, 183 mmol). The mixture was heated to 80° C. and refluxed under nitrogen for 1.5 h. The reaction was evaporated to dryness on a rotary evaporator. The residue was dissolved in 500 mL of methylene chloride and 100 mL of water. The organic layer was separated and washed with water (2×100 mL), saturated aqueous sodium chloride solution (100 mL), dried over magnesium sulfate, filtered and concentrated in vacuum to afford the a 45:55 mixture of E- and Z- (4-(4-fluorophenyl)-8-(hydroxyimino)-2-(1-methylethyl)-5,6,7,8-tetrahydroquinolin-3-yl)methyl acetate (22 g, 98% yield): HPLC (method 6) $t_R$=3.71 min; LRMS (ESI, pos. ion spectrum): m/z 371 (M+H).

To the oxime mixture (22 g, 59.5 mmol) in 500 mL of methylene chloride was added an ether solution of HCl (2.0 M, 56 mL, 112 mmol) dropwise. The mixture was allowed to stir for 16 h. The reaction was cooled to 0° C. and was neutralized with saturated aqueous sodium bicarbonate solution until its pH value was 7-8. The organic layer was separated, washed with saturated aqueous sodium chloride solution (200 mL), dried over magnesium sulfate, filtered and concentrated. The residue was recrystallized from methylene chloride-hexanes to afford 19.3 g (86%) of (E)-(4-(4-fluorophenyl)-8-(hydroxyimino)-2-(1-methylethyl)-5,6,7,8-tetrahydroquinolin-3-yl)methyl acetate: HPLC (method 6) $t_R$=3.09 min; LRMS (ESI, pos. ion spectrum) m/z 371 (M+H).

F. (4-(4-Fluorophenyl)-2-(1-methylethyl)-8-oxo-6,7,8,9-tetrahydro-5H-pyrido[2,3-b]azepin-3-yl)methyl Acetate To a solution of the compound of Part E (19.3 g, 52.1 mmol) in 150 mL of dry methylene chloride at 0° C. was added 4-(trifluoromethyl)benzenesulfonyl chloride (19.1 g, 78.1 mmol) and triethylamine (10.9 mL, 78.1 mmol). The mixture was allowed to stir for 16 h and was concentrated to dryness on a rotary evaporator. The residue was dissolved in a solution of pyridine (100 mL), iso-propanol (30 mL) and water (100 mL), and was heated to 80° C. for 4 h. The reaction was evaporated to dryness on a rotary evaporator. The residue was partitioned in saturated aqueous sodium bicarbonate solution (100 mL) and ethyl acetate (300 mL). The organic layer was separated, washed with saturated aqueous sodium chloride solution (100 mL), dried over magnesium sulfate, filtered and concentrated to afford the crude product. Flash chromatography on a silica gel column with 20-50% of ethyl acetate/hexanes as the eluent to afford 16 g (83% yield) of (4-(4-fluorophenyl)-2-(1-methylethyl)-8-oxo-6,7,8,9-tetrahydro-5H-pyrido[2,3-b]azepin-3-yl)methyl acetate: HPLC (method 6) $t_R$=3.56 min; LRMS (ESI, pos. ion spectrum): m/z 371 (M+H).

G. 4-(4-Fluorophenyl)-3-(hydroxymethyl)-2-(1-methylethyl)-9-methyl-6,7-dihydro-5H-pyrido[2,3-b]azepin-8 (9H)-one To a solution of the compound of Part F (12.6 g, 33.9 mmol) in 600 mL of THF at −78° C. was added lithium bis(trimethylsilyl)amide (40.7 mL, 1.0 M in THF, 40.7 mmol) and the mixture was stirred for 30 min. Methyl iodide (6.35 mL, 102 mmol) was added dropwise over 10 min. The reaction was warmed to room temperature within 30 min, and stirred for additional 30 min. The reaction was cooled to 0° C. and was quenched with saturated aqueous sodium bicarbonate solution (100 mL) and extracted with ethyl acetate (4×100 mL). The organic fractions were combined, washed with saturated aqueous sodium chloride solution (200 mL), dried over magnesium sulfate, filtered and concentrated.

To the residue in 150 mL of THF and 50 mL of methanol was added potassium hydroxide solution (100 mL, 1.0 M). The mixture was stirred for 1 h. The organic solvent was removed in vacuo, and the mixture was neutralized with 1N HCl to pH~8 at 0° C. The reaction was extracted with ethyl acetate (3×100 mL) and the organic fractions combined, washed with saturated aqueous sodium chloride solution (200 mL), dried over magnesium sulfate, filtered and concentrated in vacuum. Flash chromatography of the residue on a silica gel column with 20-40% of ethyl acetate/hexanes as the eluent afforded 4-(4-fluorophenyl)-3-(hydroxymethyl)-2-(1-methylethyl)-9-methyl-6,7-dihydro-5H-pyrido[2,3-b]azepin-8(9H)-one (10 g, 86%): HPLC (method 6) $t_R$=3.55 min; LRMS (ESI, pos. ion spectrum): m/z 343 (M+H).

H. 4-(4-Fluorophenyl)-2-(1-methylethyl)-9-methyl-8-oxo-6,7,8,9-tetrahydro-5H-pyrido[2,3-b]azepine-3-carboxaldehyde To a solution of the compound of Part G (10 g, 29 mmol) in 200 mL of methylene chloride was added Dess-Martin periodinane (18.9 g, 44.5 mmol). The reaction was stirred for 45 min. The reaction was diluted with water (200 mL) and methylene chloride (200 mL). The organic layer was separated, washed with water (100 mL), dried over magnesium sulfate, filtered and concentrated to afford the crude product. Flash chromatography on a silica gel column with 10-20% ethyl acetate/hexanes as the eluant gave 8.5 g (86% yield) of 4-(4-fluorophenyl)-2-(1-methylethyl)-9-methyl-8-oxo-6,7,8,9-tetrahydro-5H-pyrido[2,3-b]azepine-3-carboxaldehyde: HPLC (method 6) $t_R$=3.98 min; LRMS (ESI, pos. ion spectrum): m/z 341 (M+H).

I. 1,1-Dimethylethyl 2-((4R,6S)-6-((E)-2-(4-(4-fluorophenyl)-2-(1-methylethyl)-9-methyl-8-oxo-6,7,8,9-tetrahydro-5H-pyrido[2,3-b]azepin-3-yl)ethenyl)-2,2-dimethyl-1,3-dioxan-4-yl)acetate To a solution of the compound of Part H (8.5 g, 25 mmol) and 1,1-dimethylethyl(4R,6S)-2,2-dimethyl-6-(1-phenyl-1H-tetrazole-5-sulfonylmethyl)-[1,3]dioxan-4-yl-acetate (13.6 g, 30 mmol) in THF (250 mL) at −78° C. was added LiHMDS (30 mL, 1.0 M in THF, 30 mmol) dropwise over 10 minutes. After 1 h, the reaction was quenched at −78° C. by the addition of 100 mL of saturated aqueous ammonium chloride solution followed by the addition of ethyl acetate (200 mL). The aqueous layer was extracted with an additional 200 mL of ethyl acetate. The organic fractions were combined, washed with saturated aqueous sodium chloride solution (100 mL), dried over magnesium sulfate, filtered, and concentrated in vacuum. Purification of the residue by flash chromatography on a silica gel column with 15-20% ethyl acetate/hexanes as the eluant provided 1,1-dimethylethyl 2-((4R,6S)-6-((E)-2-(4-(4-fluorophenyl)-2-(1-methylethyl)-9-methyl-8-oxo-6,7,8,9-tetrahydro-5H-pyrido[2,3-b]azepin-3-yl)ethenyl)-2,2-dimethyl-1,3-dioxan-4-yl)acetate (14 g, 99%): HPLC (method 6) $t_R$=4.64 min; LRMS (ESI, pos. ion spectrum) m/z=567 (M+H).

J. 7-[4-(4-Fluorophenyl)-6,7,8,9-tetrahydro-9-methyl-2-(1-methylethyl)-8-oxo-5H-pyrido[2,3-b]azepin-3-yl]-3,5-dihydroxy-(3R,5S,6E)-6-heptenoic Acid, Monosodium Salt To a stirred solution of the compound of Part 1 (14.0 g, 24.7 mmol) in tetrahydrofuran (100 mL) was added aqueous HCl (14.8 mL, 6.0 N, 88.8 mmol). After 70 minutes, aqueous NaOH (23 mL, 6.0 N, 138 mmol) was added. Methanol (40 mL) was added to ensure a homogeneous reaction mixture. After stirring for 20 minutes, the mixture was neutralized with aqueous HCl (1.0 N) solution to pH~8. The organic solvent was removed in vacuo to yield a thick, pale-yellow slurry. This material was dissolved in 200 mL of water and loaded onto a C-18 silica gel column (J.T. Baker catalog # 7025-00, 40 μM, 300 g, 55 mm id×200 mm). The column was eluted consecutively with water (1000 mL), 5% methanol in water (1000 mL), 10% methanol in water (2000 mL), 25% methanol in water (1000 mL) and then 50% methanol in water (2000 mL). The product-containing fractions (fractions between 10-25% methanol in water) were combined and concentrated in vacuo to dryness. The residue was dissolved in methanol (100 mL) and filtered through a sintered funnel. The filtrate was concentrated to dryness and the residue was redissolved in 100 mL of water and lyophilized to afford 7-[4-(4-fluorophenyl)-6,7,8,9-tetrahydro-9-methyl-2-(1-methylethyl)-8-oxo-5H-pyrido[2,3-b]azepin-3-yl]-3,5-dihydroxy-(3R,5S,6E)-6-heptenoic acid, monosodium salt (10.6 g, 87%) as a white solid: HPLC (method 6) $t_R$=3.4 min; MS (pos. ion spectrum) m/z 471 (M+H).

Example 17

7-[(2S)-6-(4-Fluorophenyl)-1,2,3,5-tetrahydro-2-methyl-8-(1-methylethyl)-1-(methylsulfonyl)pyrido [2,3-e][1,4]oxazepin-7-yl]-3,5-dihydroxy-(3R,5S, 6E)-6-heptenoic Acid, Monosodium Salt

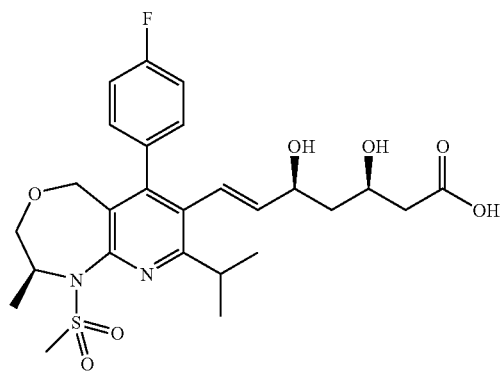

The title compound was prepared using the procedure described for Example 4: HPLC (method 4) $t_R$=20.5 min; LRMS (ESI, pos. ion spectrum) m/z 537 (M+H).

Example 18

7-[(3S)-6-(4-Fluorophenyl)-1,2,3,5-tetrahydro-3-methyl-8-(1-methylethyl)-1-(methylsulfonyl)pyrido [2,3-e][1,4]oxazepin-7-yl]-3,5-dihydroxy-(3R,5S, 6E)-6-heptenoic Acid, Monosodium Salt

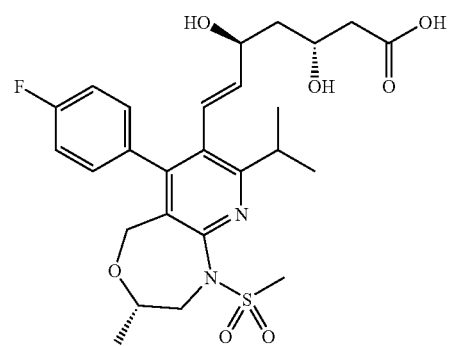

The title compound was prepared using the procedure described for Example 4: HPLC (method 4) $t_R$=21.2 min; LRMS (ESI, pos. ion spectrum) m/z 537 (M+H).

Example 19

7-[1-(Ethylsulfonyl)-6-(4-fluorophenyl)-1,2,3,5-tetrahydro-8-(1-methylethyl)pyrido[2,3-e][1,4]oxazepin-7-yl]-3,5-dihydroxy-(3R,5S,6E)-6-heptenoic Acid, Monosodium Salt

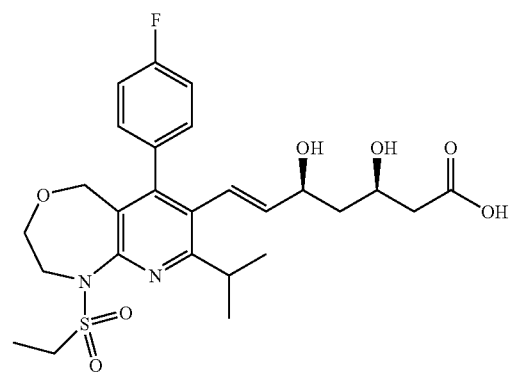

The title compound was prepared using the procedure described for Example 4: HPLC (method 4) $t_R$=21.2 min; LRMS (ESI, pos. ion spectrum) m/z 537 (M+H).

Example 20

7-[4-(4-Fluorophenyl)-5,6,7,8-tetrahydro-2-(1-methylethyl)-8-(methylsulfonyl)-1,8-naphthyridin-3-yl]-3,5-dihydroxy-(3R,5R,6E)-6-heptenoic Acid, Monosodium Salt

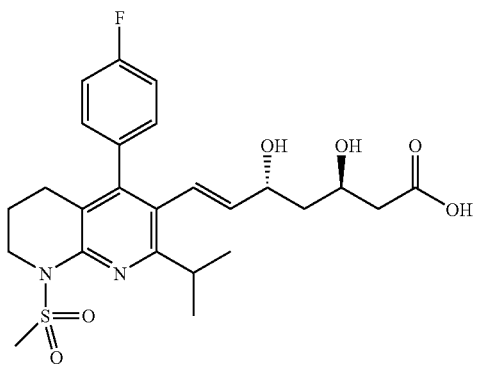

A solution of the title compound of Example 1 (1.5 g, 2.83 mmol) in tetrahydrofuran (6 mL), water (5 mL) and aqueous 6N HCl (5 mL, 30.00 mmol) was stirred for 3 days. To the mixture was added a solution of aqueous 4 N NaOH (8.5 mL, 34 mmol) and the mixture was concentrated. The residue was dissolved in water (10 mL) and a 3-mL portion of the solution was purified by C-18 column. (Solvent A—water, solvent B—acetonitrite; flow rate-100 mL/min; Gradient—solvent A for 20 min then a linear gradient from 0% B to 25% B over 30 min and then hold at 25% B for 10 min). Pure product-containing fractions were collected and concentrated in vacuo. The residue was dissolved in water (5 mL) and was lyophilized to provide 7-[4-(4-fluorophenyl)-5,6,7,8-tetrahydro-2-(1-methylethyl)-8-(methylsulfonyl)-1,8-naphthyridin-3-yl]-3,5-dihydroxy-(3R,5R,6E)-6-heptenoic acid, monosodium salt: 70 mg as white lyophilate: LCMS (ESI, pos. ion spectrum) m/z 507 (M+H); LC method 4, $t_R$=25.7 min.

Example 21

7-[(2S)-1-(Ethylsulfonyl)-6-(4-fluorophenyl)-1,2,3,5-tetrahydro-2-methyl-8-(1-methylethyl)pyrido[2,3-e][1,4]oxazepin-7-yl]-3,5-dihydroxy-(3R,5S,6E)-6-heptenoic Acid, Monosodium Salt

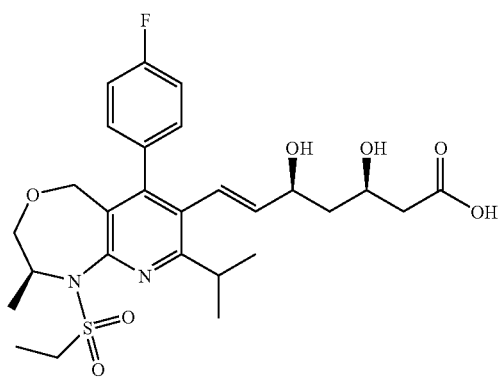

The title compound was prepared using the procedure described for Example 4: HPLC (method 4) $t_R$=22.1 min; LRMS (ESI, pos. ion spectrum) m/z 551 (M+H).

Example 22

Preparation of (E)-(3R,5S)-7-[4-(4-Fluorophenyl)-2-isopropyl-8-methanesulfonyl-5,6,7,8-tetrahydro-[1,8]naphthyridin-3-yl]-3,5-dihydroxyhept-6-enoic Acid

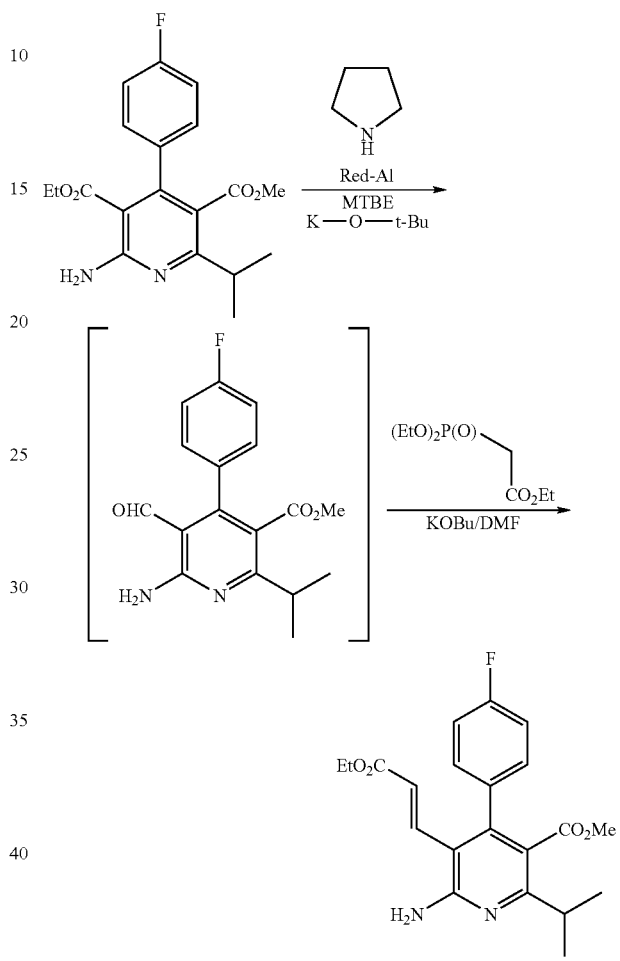

A. Preparation of methyl 6-amino-5-(3-ethoxy-3-oxopropenyl)-4-(4-fluorophenyl)-2-isopropylnicotinate To a solution of Red-Al (65% wt in toluene, 2.29 kg, 7.36 mol) in THF (2.25 L) was charged dropwise a solution of pyrrolidine (0.61 kg, 8.6 mol) in MTBE (0.70 L) at −20° C. to −5° C. under nitrogen. Off-gassing was observed during the addition. The solution was stirred at room temperature (19° C.) overnight. Potassium t-butoxide (1M in THF, 0.52 L, 0.52 mol) was added in one portion and the mixture was stirred at room temperature for 1 h to give a clear solution. This solution was added dropwise to a suspension of 3-ethyl 5-methyl 2-amino-4-(4-fluorophenyl)-6-(1-methylethyl)-3,5-pyridinedicarboxylate (0.85 kg, 2.36 mol) in MTBE (8.50 L) at −16° C. to −13° C. After stirring at −15° C. for an additional 30 min, the mixture was quenched with 1N NaOH (7.0 L) below 5° C. and then warmed to 20° C. The organic layer was separated and washed with 1N HCl (7.0 L), aqueous NaHCO₃ (saturated, 7.0 L) and water (7.0 L). Concentration in vacuo to remove most of the solvents was followed by a solvent exchange with DMF (2.0 L) which gave a clear solution of ethyl 6-amino-4-(4-fluorophenyl)-5-formyl-2-isopropylnicotinate in DMF (KF <0.1%) at 40° C. In another reactor was charged potassium t-butoxide (1M in THF, 3.5 L, 3.5 mol) in DMF (7.0 L) at 10° C. under nitrogen. To this solution was added triethylphosphonacetate (0.64 kg, 2.8 mol) slowly maintaining the temperature below 20° C. The mixture was stirred at 18-20° C. for 30 min, then cooled to −5° C. to 0° C. The solution of 6-amino-4-(4-fluorophenyl)-5-formyl-2-isopropylnicotinate in DMF was added dropwise to this mixture at 0-5° C. The mixture was stirred for additional 45 min and then quenched with 6% aqueous $KH_2PO_4$ solution (8.20 L) at 0-10° C. The resulting slurry was stirred at room temperature for 2 h. The solid was collected by filtration, washed with water (10.0 L) and dried in vacuo for two days at 50-60° C. to provide methyl 6-amino-5-(3-ethoxy-3-oxopropenyl)-4-(4-fluorophenyl)-2-isopropylnicotinate (740.0 g, yield: 81.2%) as a yellow solid: mp 160.13° C. (DSC); $^1H$ NMR (400 MHz, $CDCl_3$) δ 1.16-1.30 (m, 9H), 2.92-3.05 (m, 1H), 3.38-3.51 (s, 3H) 4.10-4.23 (m, 2H), 4.95-5.10 (b, 2H), 6.15-6.24 (d, 1H), 7.02-7.20 (m, 4H), 7.23-7.36 (d, 2H); $^{13}C$ NMR (100 MHz, $CDCl_3$) δ 14.20, 22.09, 22.21, 33.38, 51.90, 60.61, 110.50, 115.24, 115.46, 120.66, 121.99, 130.61, 130.69, 140,32, 148.62, 156.38, 161.37, 163.52, 163.83, 166.53, 169.17. Anal. Calcd for $C_{21}H_{23}FN_2O_4$: C, 65.27; H, 5.99; N, 7.25; F, 4.91. Found: C, 65.11; H, 6.21; N, 7.11; F, 4.77.

water wet, 27.0 g) at room temperature (18.0° C.). The mixture was purged with nitrogen for 15 min, and then hydrogenated by sparging hydrogen into the reactor at room temperature. The reaction was monitored by HPLC until <1% of the starting material was left (2 h). The Pd/C was removed by filtration through a pad of Celite®. The pad was washed with toluene (0.4 L). The filtrate was stirred at 100-110° C. in the presence of p-toluenesulfonic acid monohydrate (7.4 g, 0.04 mol) for 3 h. After cooling to 60° C., the mixture was washed with water (350 mL). The organic layer was concentrated in vacuo to ·400 mL. Heptane (170 mL) was added and the slurry stirred at 20° C. for 2 h. Filtration followed by a toluene/heptane wash (1:1, 500 mL) and drying in vacuo at 45° C. for 3 days provided methyl 4-(4-fluorophenyl)-2-isopropyl-7-oxo-5,6,7,8-tetrahydro-[1,8]naphthyridine-3-carboxylate (211.5 g, yield: 88.4%) as an off-white solid: mp 190.75° C. (DCS); $^1H$ NMR (400 MHz, $CDCl_3$) δ 1.19-1.28 (m, 6H), 2.52-2.62 (m, 2H), 2.65-2.73 (m, 2H), 2.94-3.07 (m, 1H), 3.47-3.56 (s, 3H), 7.08-7.28 (m, 4H), 7.85-7.96 (b, 1H); $^{13}C$ (100 MHz, $CDCl_3$) δ 21.70, 22.23, 30.40, 30.52, 33.30, 52.08, 113.70, 115.46, 115.68, 124.33, 130.04, 130.12, 132.04, 146.50, 150.74, 161.35, 163.87, 168.75, 170.79. Anal. Calcd for $C_{19}H_{19}FN_2O_3$: C, 66.65; H, 5.59; N, 8.18; F, 5.54. Found: C, 66.49; H, 5.45; N, 8.13; F 5.59.

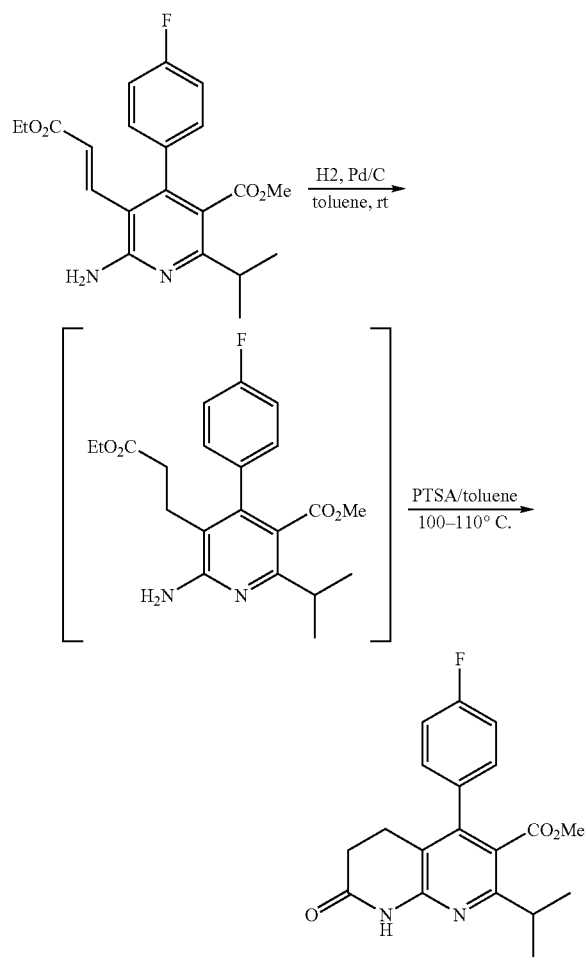
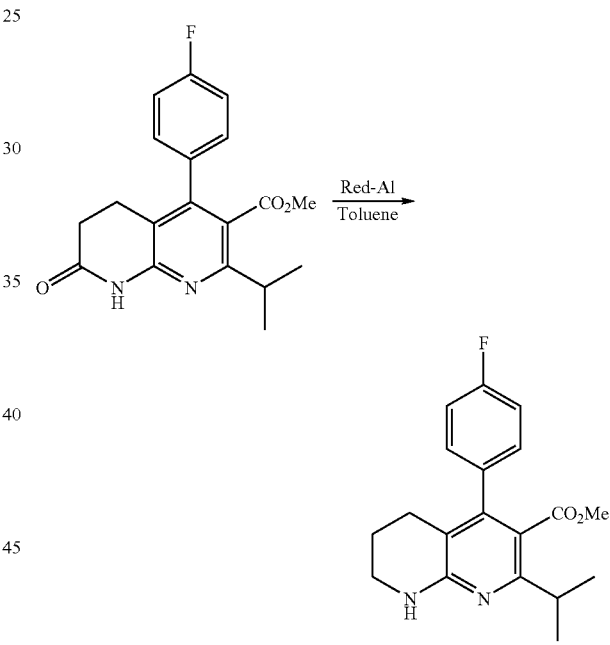

B. Methyl 4-(4-fluorophenyl)-2-isopropyl-7-oxo-5,6,7,8-tetrahydro-[1,8]naphthyridine-3-carboxylate To a suspension of the compound from Part A (270.0 g, 0.70 mol) in toluene (2.25 L) was added 10% Pd/C (50%

C. Methyl 4-(4-fluorophenyl)-2-isopropyl-5,6,7,8-tetrahydro-[1,8]naphthyridine-3-carboxylate A solution of Red-Al (185 mL, 0.613 mol, 65 weight % in toluene) in anhydrous toluene (250 mL) was cooled to 5° C. A solution of Part B methyl 4-(4-fluorophenyl)-2-isopropyl-7-oxo-5,6,7,8-tetrahydro-[1,8]naphthyridine-3-carboxylate (100. g, 0.292 mol) in anhydrous THF (500 mL) was added over 30 min. The reaction mixture was stirred at 5° C. for 3 h. The reaction was quenched by adding a solution of potassium sodium tartrate (10%, 200 mL) slowly. After toluene (100 mL) was added, the two phases were separated. The organic phase was washed with $NaH_2PO_4$ (5%, 200 mL), followed by $H_2O$ (200 m]L), and brine (200 m]L), dried over $MgSO_4$, and filtered. The solvent was removed under reduced pressure and the obtained solid dried at 40° C. under vacuum to provide 88.27 g (92% yield) of methyl 4-(4-fluorophenyl)-2-isopropyl-5,6,7,8-tetrahydro-[1,8]naphthyridine-3-carboxylate as an off-white solid: mp 168-170° C.; $^1$H NMR (400 MHz, CDCl$_3$) δ 1.23 (d, J=7.0 Hz, 6H), 1.79 (m, 2H), 2.37 (t, J=6.4 Hz, 2H), 2.99 (m, 1H), 3.39 (m, 2H), 3.40 (s, 3H), 5.07 (s, 1H), 7.03-7.16 (m, 4H); $^{13}$C NMR (100 MHz, CDCl$_3$) δ 169.5, 162.9, 160.4, 155.7, 146.1, 133.8, 129.9, 117.9, 115.1, 114.9, 110.6, 52.0, 41.9, 33.4, 25.3, 23.0, 22.0; HRMS calcd for C$_{19}$H$_{22}$FN$_2$O$_2$ (M+1) 329.1665, found 329.1666.

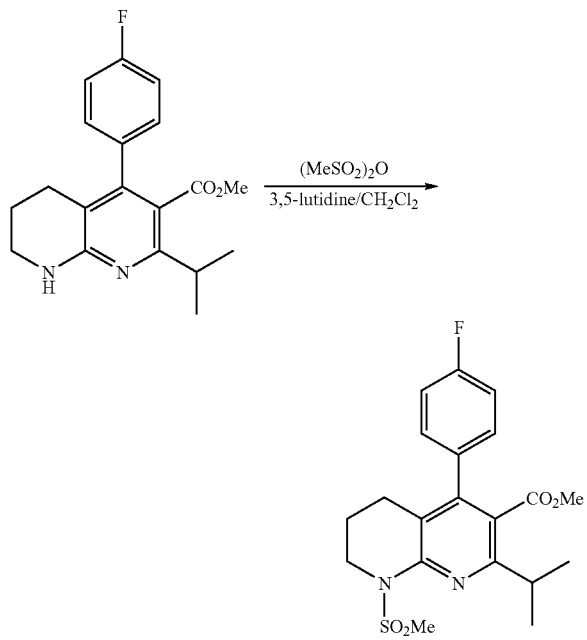

D. Methyl 4-(4-fluorophenyl)-2-isopropyl-8-methanesulfonyl-5,6,7,8-tetrahydro-[1,8]naphthyridine-3-carboxylate A solution of (MeSO$_2$)$_2$O (15.9 g, 0.091 mol) in anhydrous CH$_2$Cl$_2$ (50 mL) was added to a solution of Part C methyl 4-(4-fluorophenyl)-2-isopropyl-5,6,7,8-tetrahydro-[1,8] naphthyridine-3-carboxylate (10. g, 0.030 mol) and 3,5-lutidine (20.9 mL, 0.182 mol) in anhydrous toluene (100 mL) at room temperature. The reaction mixture was stirred at room temperature for 3 days. Ethyl acetate (200 mL) and H$_2$O (50 mL) were added, and the resulting two phases were separated. The organic phase was washed with aqueous NaHCO$_3$ (5%, 50 mL), followed by half-saturated brine (50 mL). The solvent was removed under reduced pressure to afford a yellowish oil which solidified slowly. The crude material was recrystallized from i-PrOH/H$_2$O (85:15, 45 mL) to afford 10.5 g (85% yield) of methyl 4-(4-fluorophenyl)-2-isopropyl-8-methanesulfonyl-5,6,7,8-tetrahydro-[1,8]naphthyridine-3-carboxylate as a off-white solid.

E. Alternative preparation of methyl 4-(4-fluorophenyl)-2-isopropyl-8-methanesulfonyl-5,6,7,8-tetrahydro-[1,8]naphthyridine-3-carboxylate To a solution of Red-Al (65 wt. % in toluene, 2480 g, 7.95 mol) in anhydrous toluene (5.5 L) at −10° C. was added a pre-mixed solution of Part B methyl 4-(4-fluorophenyl)-2-isopropyl-7-oxo-5,6,7,8-tetrahydro-[1,8]naphthyridine-3-carboxylate (1107 g, 3.23 mol) over a period of 75 min, while the temperature was maintained between 0 to 5° C. Once the reaction was complete as monitored by HPLC, the reaction mixture was quenched with a cold Rochelle's salt solution (10%, 3.0 L), and toluene (2.5 L) was added. The two phases were separated, and the organic layer was washed with NaH$_2$PO$_4$ (5%, 2×2.0 L), water (2.0 L), and brine (50%, 2.0 L). The organic layer was distilled under reduced pressure to remove THF and water until a volume of 9.5 L was obtained. A solution of 3,5-lutidine (2.0 L, 17.9 mol) was added over a period of 15 min, followed by a solution of methanesulfonic anhydride (1.30 kg, 7.46 mol) in CH$_2$Cl$_2$ (3.0 L). The reaction was stirred at ambient temperature for 3 days. The reaction mixture was then quenched by adding water (5.0 L). The organic phase was separated, washed with NaH$_2$PO$_4$ (5%, 5.0 L), NaHCO$_3$ (5%, 5.0 L), and brine (50%, 5.0 L). The solvent was removed under reduced pressure to give an oil which was dried under vacuum overnight. The crude solid thus obtained was dissolved in i-PrOH/H$_2$O (85:15, 5.0 L), heated to 75° C. and gradually cooled to 0° C. over a period of 16 h to afford 947.0 g (78% yield) of methyl 4-(4-fluorophenyl)-2-isopropyl-8-methanesulfonyl-5,6,7,8-tetrahydro-[1,8]naphthyridine-3-carboxylate as a pale yellow solid: mp 160-162° C.; $^1$H NMR (400 MHz, CDCl$_3$) δ 7.07-7.15 (m, 4H), 3.90 (dd, J=11.2, 5.8 Hz, 2H), 3.60 (s, 3H), 3.47 (s, 3H), 3.04 (septet, J=6.8 Hz, 1H), 2.42 (dd, J=12.7, 6.4 Hz, 2H), 1.88-1.94 (m, 2H), 1.30 (d, J=6.8 Hz, 6H); $^{13}$C NMR (100 MHz, CDCl$_3$) δ 168.2, 163.2, 160.8, 159.1, 150.6, 147.4, 132.4, 129.8, 123.5, 116.7, 115.5, 52.4, 45.6, 44.3, 34.1, 25.9, 23.3; HRMS calcd for C$_{19}$H$_{24}$FN$_2$O$_4$S (M+1) 407.1441, found 407.1449.

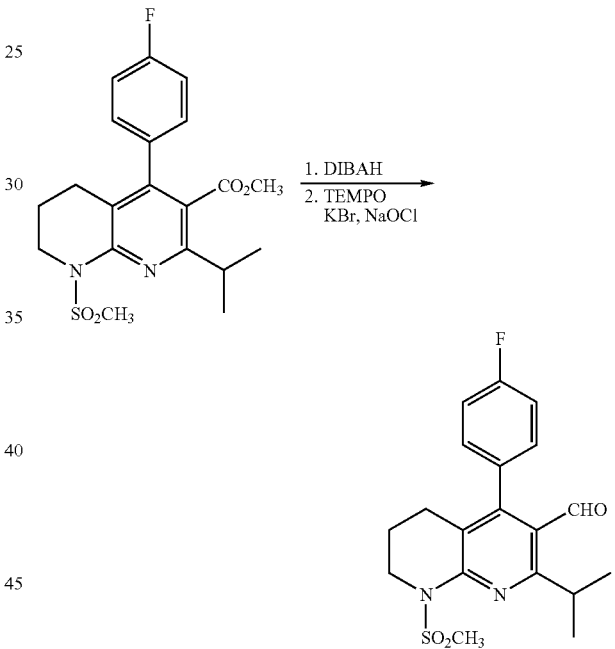

F. Preparation of 4-(4-Fluorophenyl)-2-isopropyl-8-methanesulfonyl-5,6,7,8-tetrahydro-[1,8]naphthyridine-3-carboxaldehyde To a stirred solution of 480 g (1.18 mol) of the compound from Part E in 4.8 L of dry methylene chloride (KF<0.01) cooled to −10 to −15° C. was added 2.95 L (2.5 mol eq) of a 1.0M solution of DIBAL in methylene chloride maintaining the temperature below −10° C. The addition took 2 h. After the addition was complete HPLC analysis showed complete reduction. The excess DIBAL was quenched by the addition of 500 mL of isopropyl alcohol. Considerable off-gasing was observed. The rich methylene chloride stream was transferred to a carboy and 580 g (3.01 mol) of citric acid was charged to the reactor followed by 2.5 L of water (~1.2 M citric acid). The mixture was stirred until complete dissolution was obtained (~15 min). The citric acid solution was cooled to −5° C. and the rich methylene chloride stream charged back into the reactor maintaining the temperature below 5° C. The addition took 1.5 h. To the resulting emulsion (pH 1.2) was added 600 mL of 10 N sodium hydroxide over a 0.5 h period to a pH endpoint of 7.0 (range 7.0-7.5). Agitation was stopped and a clean phase split was obtained after 15 min. The lower rich methylene chloride stream was drawn off for further processing and the spent aqueous stream was discarded. The rich methylene chloride stream was washed again with 1.5 L of a 1.2 M citric acid solution. After pH adjustment to 7.1 with 10 M sodium hydroxide a clean phase split was obtained. The volume of the rich methylene chloride stream was reduced to ~4.8 L via distillation at atmospheric pressure. Then 14.1 g (0.118 mol, 0.1 mol eq) of KBr and 9.5 g (0.059 mol, 0.05 mol eq) of TEMPO were added and the resulting solution was cooled to −10 to −15° C. Then, 2 L of bleach (about 1.4 eq of 6 wt % NaOCl previously adjusted to pH 9.5 with NaHCO$_3$) was added over a 2 h period maintaining the temperature below 4° C. After the bleach addition was complete, HPLC analysis showed complete conversion to Example 22 Compound F. The solution was cooled to 0 to 5° C. and 2 L of 1N Na$_2$S$_2$O$_3$ was added over a 10 min period maintaining the temperature below 10° C. The biphasic mixture was agitated for 15 min. Agitation was stopped and the layers separated. The rich methylene chloride stream was washed with 2 L of 0.5 M sodium hydroxide and 2 L of half-saturated brine. The rich methylene chloride stream was concentrated to minimum agitation volume and 2.3 L of isopropyl alcohol was added. The resulting slurry was warmed just to reflux at which time complete dissolution was observed. The solution was cooled to room temperature over a 0.5 h period (crystallization commenced at 40° C.) and then to 0-5° C. The crystal slurry was held at this temperature for 1 h. The crystals were collected via filtration and the cake washed with ~1 cake volume of ice cold isopropyl alcohol (~400 mL). The cake was deliquored for 1 h and then dried under vacuum at 50-55° C. for 16 h to yield 410 g (91.7% overall) of Example 1 Compound F as a white solid. HPLC analysis indicated a purity of 97.7%; mp 142-144° C.; $^1$H NMR (400 MHz, CDCl$_3$) δ 1.31 (d, J=7.1 Hz, 6H), 1.93 (m, 2H), 2.37 (t J=6.4 Hz, 2H,), 3.62 (s, 3H), 3.93 (t, J=5.7 Hz, 2H), 3.99 (m, 1H), 7.15 (m, 4H), 9.69 (s, 1H); $^{13}$C NMR(100 MHz, CDCl$_3$) δ 191.4, 165.0, 163.5, 161.0, 153.3, 152.1, 131.1, 130.3, 122.5, 116.9, 116.1, 115.9, 45.7, 44.2, 32.1, 25.6, 23.1, 22.8; HRMS calcd for C$_{19}$H$_{22}$FN$_2$O$_3$S (M+1) 377.1335, found 377.1334.

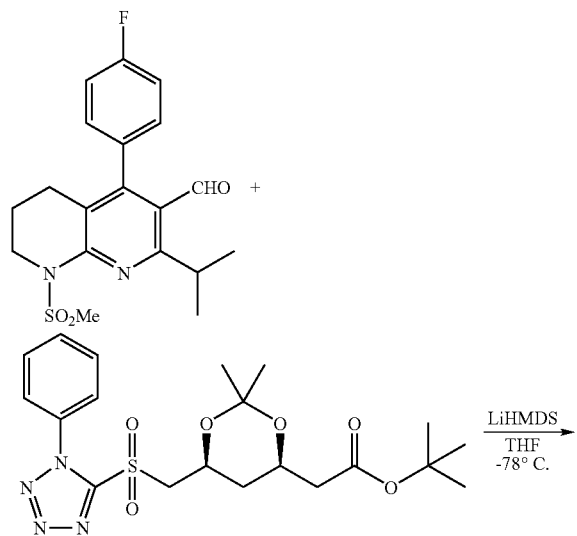

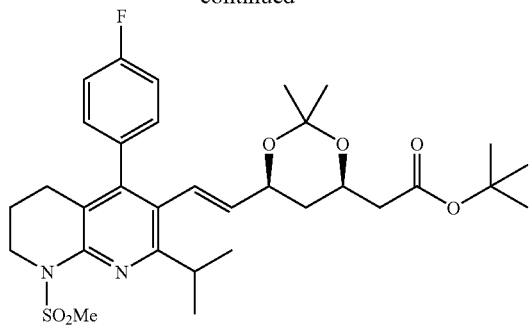

G. 1,1-Dimethylethyl(4R,6S)-(E)-6-{2-[4-(4-fluorophenyl)-2-isopropyl-8-methanesulfonyl-5,6,7,8-tetrahydro-[1,8]naphthyridin-3-yl]ethenyl}-2,2-dimethyl-[1,3]dioxan-4-acetate To a solution of Part F 4-(4-fluorophenyl)-2-isopropyl-8-methanesulfonyl-5,6,7,8-tetrahydro-[1,8]naphthyridine-3-carboxaldehyde (8.05 g, 0.021 mol) and 1,1-dimethylethyl ((4R,6S)-2,2-dimethyl-6-(1-phenyl-1H-tetrazole-5-sulfonylmethyl)-[1,3]dioxan-4-yl)acetate (11.13 g, 0.025 mol) in anhydrous THF (80 mL) cooled to −78° C. was added LiHMDS (1 M in THF, 24.6 mL, 0.025 mol) over 30 min at −78° C. The reaction mixture was stirred for 1.5 h at −78° C. The reaction was quenched with an aqueous solution of NH$_4$Cl (7.5%, 35 mL). After the mixture was warmed to room temperature, ethyl acetate (150 mL) was added, and the two phases were separated. The organic phase was washed with aqueous NaHCO$_3$ (5%, 50 mL), followed by H$_2$O (50 mL), and half-saturated brine (50 mL), and was then dried over MgSO$_4$. The solvent was removed under reduced pressure to afford a crude product which was recrystallized from EtOH/H$_2$O (75:25, 260 mL) to give 11.7 g (91% yield) of 1,1-dimethylethyl(4R,6S)-(E)-(6-{2-[4-(4-fluorophenyl)-2-isopropyl-8-methanesulfonyl-5,6,7,8-tetrahydro-[1,8]naphthyridin-3-yl]ethenyl}-2,2-dimethyl-[1,3]dioxan-4-acetate as a white solid: mp 167-169° C.; $^1$H NMR (400 MHz, CDCl$_3$) δ 0.88 (q, J=12.0 Hz, 1H), 1.22-1.24 (m, 1H), 1.27 (d, J=6.9 Hz, 6H), 1.33 (s, 3H), 1.41 (s, 3H), 1.44 (s, 9H), 1.87-1.90 (m, 1H), 2.23 (dd, J=6.4, 6.4 Hz, 1H), 2.23-2.40 (m, 4H), 3.29-3.36 (m, 1H), 3.62 (s, 3H), 3.81-3.94 (m, 2H), 4.15-4.24 (m, 2H), 5.21 (dd, J=6.2, 6.2 Hz, 1H), 6.14 (d, J=17.1 Hz, 1H), 6.94-7.10 (m, 4H); $^{13}$C NMR (100 MHz, CDCl$_3$) δ 169.7, 162.8, 160.4, 160.1, 148.8, 136.7, 134.1, 130.6, 130.2, 125.1, 124.9, 116.8, 115.4, 115.2, 98.8, 80.9, 70.0, 66.1, 45.5, 44.4, 43.0, 36.9, 32.5, 30.6, 28.7, 26.4, 23.5, 23.2, 20.4; HRMS calcd for C$_{32}$H$_{44}$FN$_2$O$_6$S (M+1) 603.2904, found 603.2901.

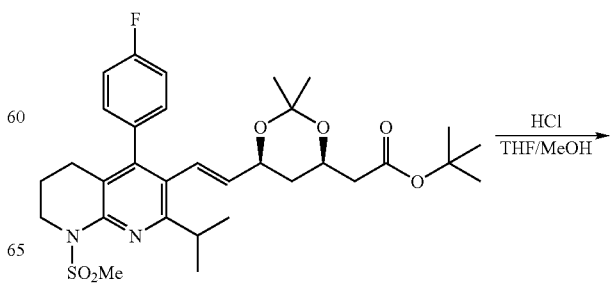

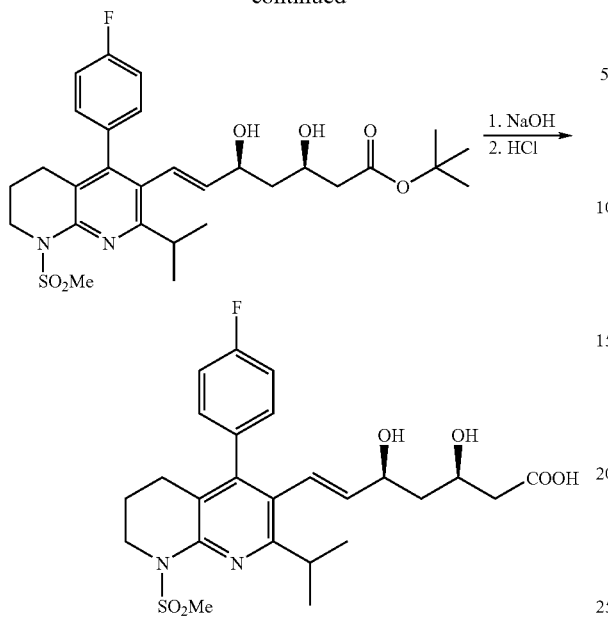

H. Preparation of (E)-(3R,5S)-7-[4-(4-Fluorophenyl)-2-isopropyl-8-methanesulfonyl-5,6,7,8-tetrahydro-[1,8]naphthyridin-3-yl]-3,5-dihydroxyhept-6-enoic Acid A solution of Part G 1,1-dimethylethyl(4R,6S)-(E)-(6-{2-[4-(4-fluorophenyl)-2-isopropyl-8-methanesulfonyl-5,6,7,8-tetrahydro-[1,8]naphthyridin-3-yl]ethenyl}-2,2-dimethyl-[1,3]dioxan-4-acetate (10.8 g, 0.018 mol) in THF/MeOH (5:2, 140 mL) was cooled to 15° C. An aqueous solution of HCl (6 N, 9.0 mL, 0.054 mol) was added over 15 min. The reaction mixture was stirred at 15° C. for 2.5 h. An aqueous solution of NaOH (2 N, 44.8 mL, 0.090 mol) was added over 15 min at 15° C. The mixture was stirred for an additional 1 h. Water (35 mL) and heptane (100 mL) were added, and the two phases were separated. The aqueous phase was washed with MTBE (30 mL). The aqueous phase was acidified with aqueous HCl (3 N) to pH 2.8, then was extracted with ethyl acetate (2 times, 100 mL and 50 mL). The organic phases were combined and the solvent was removed at 45° C. under reduced pressure until total volume of 100 mL remained. The resulting solution was cooled to 0° C. over 60 min. Seed crystals (30 mg) of Part H compound were added at 0° C. and the resulting slurry was stirred for an additional 30 min. Heptane (80 mL) was added over 30 min, and the slurry was stirred for 1 h at 0° C. The solids were collected by filtration. After drying at 60° C. under vacuum, (E)-(3R,5S)-7-[4-(4-fluorophenyl)-2-isopropyl-8-methanesulfonyl-5,6,7,8-tetrahydro-[1,8]naphthyridin-3-yl]-3,5-dihydroxyhept-6-enoic acid was obtained as a white solid (8.20 g, 90% yield): mp 184-186° C.; $^1$H NMR (400 MHz, CDCl$_3$) δ 1.10-1.18 (m, 1H), 1.21 (d, J=5.9 Hz, 6H), 1.35-1.42 (m, 1H), 1.77-1.83 (m, 2H), 2.17 (dd, J=8.1, 8.7 Hz, 1H), 2.23 (dd, J=4.7, 5.4 Hz, 1H), 2.30 (t, J=6.7 Hz, 2H), 3.31 (s, 1H), 3.36-3.41 (m, 1H), 3.58 (s, 3H), 3.71 (s, 1H), 3.77 (t, 2H, J=6.0 Hz), 4.62 (s, 1H), 4.76 (d, J=4.4 Hz, 1H), 5.29 (dd, J=5.7, 5.7 Hz, 1H), 6.18 (d, J=15.2 Hz, 1H), 7.13-7.28 (m, 4H), 12.0 (s, 1H); $^{13}$C NMR (100 MHz, DMSO-d$_6$) δ172.8, 162.6, 160.2, 159.3, 148.7, 140.5, 134.4, 131.3, 131.1, 125.3, 123.5, 117.3, 115.8, 115.6, 69.3, 65.7, 45.6, 43.9, 43.6, 32.2, 26.3, 23.7, 23.4; HRMS calcd for C$_{25}$H$_{32}$FN$_2$O$_6$S (M+1) 507.1965, found 507.1960.

Example 23

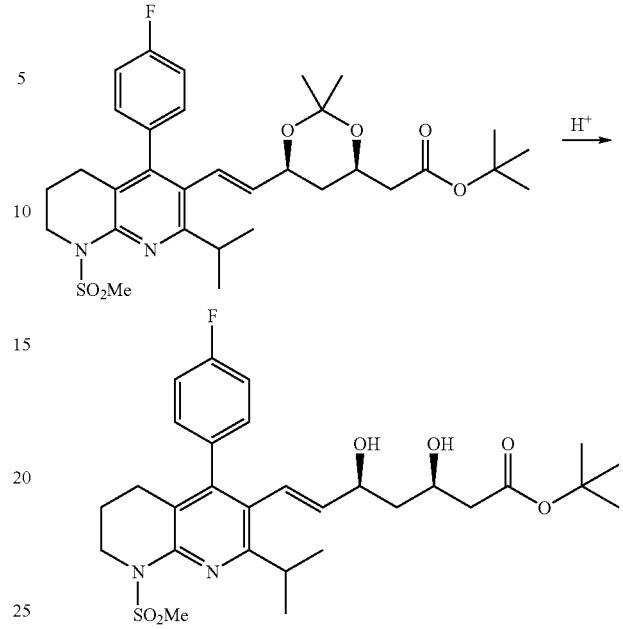

Preparation of 1,1-dimethylethyl (E)-(3R,5S)-7-[4-(4-Fluorophenyl)-2-isopropyl-8-methanesulfonyl-5,6,7,8-tetrahydro-[1,8]naphthyridin-3-yl]-3,5-dihydroxyhept-6-enoate Aqueous H$_2$SO$_4$ (2 N, 1.7 mL, 3.4 mmol) was added to a solution of Example I Compound H (1.0 g, 1.7 mmol) in THF (10 mL) at room temperature. The reaction mixture was heated to 50° C. and stirred at 50° C. for 4 h. After cooling to room temperature, the reaction mixture was neutralized with aqueous NaHCO$_3$ (5%) to pH 7.5. Ethyl acetate (25 mL) was added, and the two phases were separated. The organic phase was washed with H$_2$O (9 mL). The solvent was removed under reduced pressure and the solid dried at 55° C. under vacuum to afford 0.904 g (96.8% yield) of 1,1-dimethylethyl (E)-(3R,5S)-7-[4-(4-Fluorophenyl)-2-isopropyl-8-methanesulfonyl-5,6,7,8-tetrahydro-[1,8]naphthyridin-3-yl]-3,5-dihydroxy-hept-6-enoate as a white solid.

Example 24

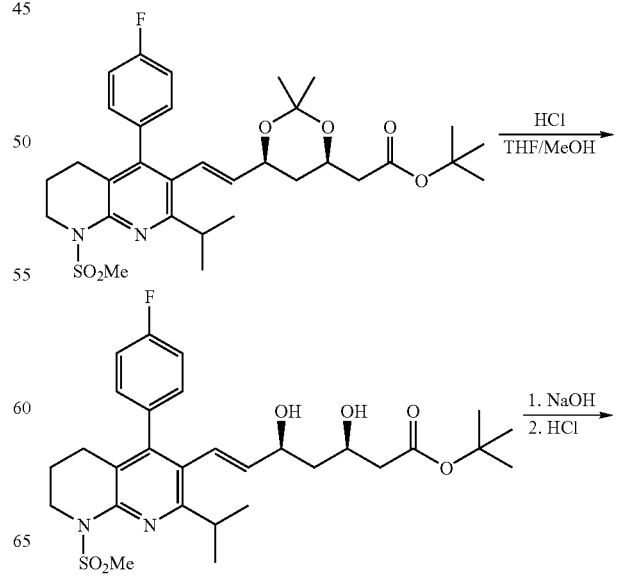

J=15.6 Hz, 1H), 7.11-7.17 (m, 2H), 7.20-7.26 (m, 2H); $^{13}$C NMR (100 MHz, DMSO-d$_6$) δ 178.4, 162.6, 160.2, 159.3, 148.7, 140.8, 134.5, 131.3, 131.2, 125.4, 123.0, 117.3, 115.7, 115.6, 69.5, 66.5, 45.6, 45.2, 44.8, 43.9, 32.2, 26.3, 23.6, 23.4.

Example 25

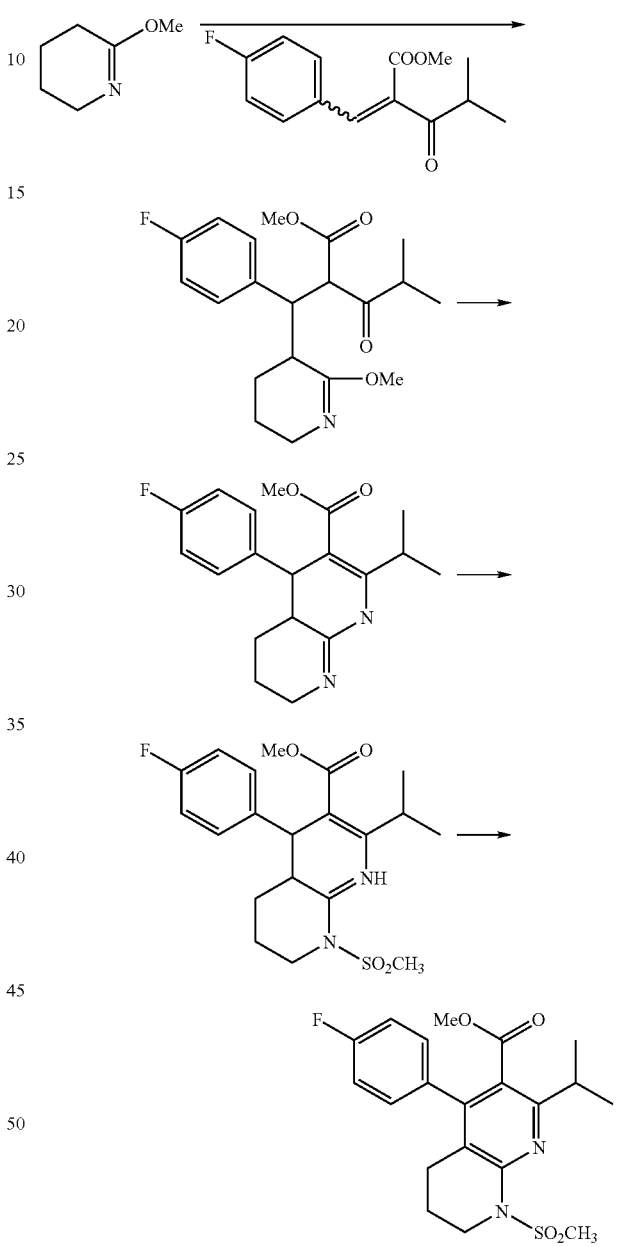

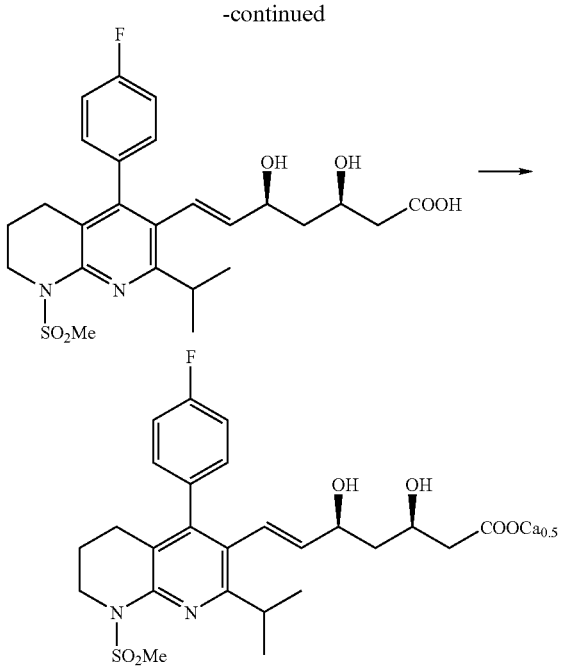

Preparation of (E)-(3R,5S)-7-[4-(4-Fluorophenyl)-2-isopropyl-8-methanesulfonyl-5,6,7,8-tetrahydro-[1,8]naphthyridin-3-yl]-3,5-dihydroxyhept-6-enoic Acid, Hemicalcium Salt A solution of Example 1 Part H, 1,1-dimethylethyl(4R,6S)-(E)-(6-{2-[4-(4-fluorophenyl)-2-isopropyl-8-methanesulfonyl-5,6,7,8-tetrahydro-[1,8]naphthyridin-3-yl]ethenyl}-2,2-dimethyl-[1,3]dioxan-4-acetate (28.4 g, 0.047 mol) in THF/MeOH (5:2, 315 mL) was cooled to 15° C. An aqueous solution of HCl (6 N, 23.5 mL, 0.141 mol) was added over 15 min. The reaction mixture was stirred at 15° C. for 2.5 h. An aqueous solution of NaOH (2 N, 118 mL, 0.235 mol) was added over 15 min at 15° C. The mixture was stirred for an additional 1 h. Water (80 mL), heptane (80 mL), and MTBE (80 mL) were added, and the two phases were separated. The aqueous phase was acidified with aqueous HCl (3 N) to pH 2.7, then extracted with ethyl acetate (2 times, 160 mL and 80 mL, respectively). The organic phases were combined and Ca(OH)$_2$ (1.82 g, 0.030 mol) was added. The mixture was stirred at room temperature for 16 h. The solvent was removed at 45° C. under reduced pressure until a total volume of 210 mL remained. The resultant solution was heated to 55° C. The solution was cooled to 0° C. over 90 min, while seed crystals of Example 24 compound (34 mg) were added at 10° C. The resulting slurry was stirred at 0° C. for an additional 30 min. Heptane (85 mL) was added over 30 min, and the slurry was stirred for 1 h at 0° C. The solids were collected by filtration. After drying at 70° C. under vacuum, (E)-(3R,5S)-7-[4-(4-fluorophenyl)-2-isopropyl-8-methanesulfonyl-5,6,7,8-tetrahydro-[1,8]naphthyridin-3-yl]-3,5-dihydroxyhept-6-enoic acid, Ca salt was obtained as a white solid (23.0 g, 93% yield): mp 215-220° C.; $^1$H NMR (400 MHz, CDCl$_3$) δ 0.98-1.04 (m, 1H), 1.20 (d, J=6.0 Hz, 6H), 1.30-1.37 (m, 1H), 1.76-1.82 (m, 2H), 1.91 (dd, J=8.9, 8.9 Hz, 1H), 2.04 (dd, J=3.6, 3.9 Hz, 1H), 2.29 (t, J=6.4 Hz, 2H), 2.50-2.51 (m, 2H), 3.31-3.38 (m, 1H), 3.58 (s, 3H), 3.60-3.62 (m, 1H), 3.76 (t, J=5.6 Hz, 2H), 4.00-4.04 (m, 1H), 5.27 (dd, J=5.2, 5.7 Hz, 1H), 6.13 (d, Preparation of Methyl 4-(4-fluorophenyl)-2-isopropyl-8-methanesulfonyl-5,6,7,8-tetrahydro-[1,8]naphthyridine-3-carboxylate Sec-butyl lithium (1.02 M in cyclohexane, 798 mL, 0.81 mole) was added dropwise to a flask containing THF (450 mL) at −78° C. The addition occurred over 20 minutes at a rate which maintained the internal reaction temperature below −50° C. 6-Methoxy-2,3,4,5-tetrahydropyridine (92 g, 0.81 mole) was dissolved in THF (150 mL) and added over 40 minutes to the solution at such a rate that the reaction temperature did not exceed −60° C. The resulting cloudy solution was stirred at −60° C. for 1 h. Methyl 3-(4-fluorophenyl)-2-isobutyrylacrylate (170 g, 0.68 mole) was added as a solution in THF (250 mL) over 50 min maintaining the temperature below −60° C. During this addition the reaction darkened in color and became transparent. The reaction was quenched with saturated ammonium chloride solution (102 mL) after the reaction had stirred at −60° C. for 45 min. Water (203 mL) was added and the reaction mixture was allowed to warm to room temperature. The phases were separated and the aqueous layer discarded affording methyl 2-[(4-fluorophenyl)-(2-methoxy-3,4,5,6-tetrahydro-pyridin-3-yl)-methyl]-4-methyl-3-oxo-pentanoate as a solution in THF/cyclohexane. Solid ammonium chloride (54.4 g, 1.02 moles) was added to the resulting solution and solvent exchange from THF/cyclohexane to methanol was effected at 50° C. and 150 mm Hg. Once the exchange to methanol was complete (2.6 L total added during distillation) the mixture was stirred overnight at 52° C. The reaction solvent was then exchanged for ethyl acetate (1500 mL total ethyl acetate added). The mixture was filtered to remove solid ammonium chloride affording a solution of methyl 4-(4-fluorophenyl)-2-isopropyl-1,4,4a,5,6,7-hexahydro-[1,8]naphthyridine-3-carboxylate. This solution described was cooled to −20° C. and diisopropylethylamine (180 mL, 1.03 moles) was added dropwise over 20 minutes. Methanesulfonyl chloride (72 mL, 0.93 mole) was then added dropwise from an addition funnel at a rate which maintained the reaction temperature below 0° C. This exothermic addition was performed over 30 minutes and the resulting orange mixture was quenched with water (250 mL) added dropwise to the reaction mixture until the suspended salts were completely dissolved. The layers were allowed to separate and the aqueous layer was removed and discarded. The ethyl acetate solution of the product, methyl 4-(4-fluorophenyl)-2-isopropyl-8-methanesulfonyl-4,4a,5,6,7,8-hexahydro-[1,8]naphthyridine-3-carboxylate was cooled to 0° C. and treated with a solution of ceric ammonium nitrate (356 g, 0.65 mole) in water (460 mL) at a rate which maintained the temperature between 0 and 5° C. At the end of the addition the organic and aqueous layers were separated and the aqueous layer was discarded. The organics were washed with water (300 mL), a 10% w/w solution of aqueous dibasic potassium phosphate (300 mL) and 5% v/v saturated sodium chloride solution (500 mL). The ethyl acetate was removed by distillation until the solution became cloudy. The product was crystallized from the solution to afford methyl 4-(4-fluorophenyl)-2-isopropyl-8-methanesulfonyl-5,6,7,8-tetrahydro-[1,8]naphthyridine-3-carboxylate (104 g, 38% over the four steps).

Example 26

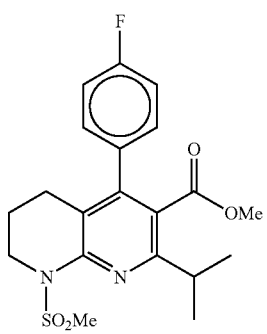

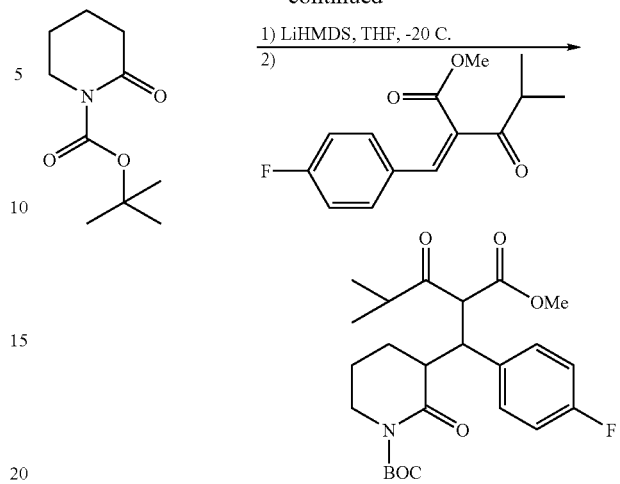

A. Preparation of Methyl 1-[(1,1-dimethylethoxy)carbonyl]-β-(4-fluorophenyl)-α-(2-methyl-1-oxopropyl)-2-oxo-3-piperidinepropanoate To a stirred solution of 1,1-dimethylethyl 2-oxo-1-piperidinecarboxylate (10 g, 50 mmole) in anhydrous THF (50 mL) which had been cooled to −20 to −30° C. was added LiHMDS in THF (55 mL, 1M, 55 mmol) solution, maintaining the temperature between −25 to −35° C. The reaction mixture was stirred for 20-30 minutes then transferred via cannula to a cooled solution (−20° C.) of methyl 3-(4-fluorophenyl)-2-isobutyrylacrylate (12.5 g, 50 mmol) in 75 mL anhydrous THF. When the reaction was complete as judged by TLC monitoring, the reaction was quenched with 100 mL of saturated ammonium chloride and extracted with ethyl acetate (2×200 mL). The combined organic phases were dried over sodium sulfate, filtered and concentrated to provide an off white solid. Recrystallization from ethyl acetate/hexanes afforded 17.4 g (77% yield) of methyl 1-[(1,1-dimethylethoxy)carbonyl]-β-(4-fluorophenyl)-α-(2-methyl-1-oxopropyl)-2-oxo-3-piperidinepropanoate in as a white crystalline solid. NMR clearly shows a mixture of isomers: IR (KBr) cm$^{-1}$ 2979, 1758, 1755, 1745, 1714, 1671; $^1$H NMR (CDCl$_3$, 400 MHz) δ 7.21-7.20 (m, 4H), 6.93-6.92 (m, 4H), 4.40 (dd, 2H), 4.09 (m, 2H), 3.66 (s, 3H), 3.58-3.33 (m, 4H), 3.32 (s, 3H), 2.80-2.48 (m, 4H), 2.02-1.60 (m, 6H), 1.47 (s, 18H), 1.43-1.51 (m, 2H), 1.08 (d, J=4 Hz, 3H), 1.05 (d, J=8 Hz, 3H), 0.85 (d, J=4 Hz, 3H), 0.71 (d, J=8 Hz, 3H); $^{13}$C NMR (CDCl$_3$, 100 MHz) δ 206.9, 206.8, 171.7, 171.6, 168.4, 168.2, 162.6, 160.2, 151.9, 134.5, 134.3, 131.1, 130.0, 130.8, 130.7, 115.2, 115.1, 115, 114.9, 82.9, 61.5, 60.8, 53.0, 52.6, 48.2, 48.0, 46.3, 45.9, 45.6, 44.9, 41.9, 40.9, 28.63, 24.2, 24.0, 21.9, 21.3, 19.5, 19.0, 18.8, 18.7; HRMS (ES) calcd. for C$_{24}$H$_{32}$FNNaO$_6$ (M+Na): 472.2111; found: 472.2100.

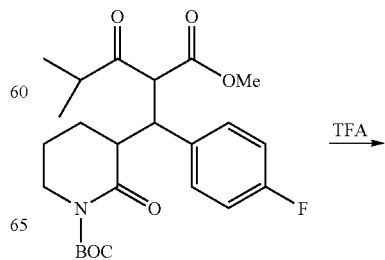

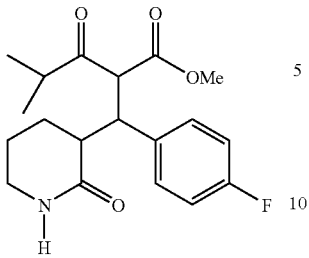

B. Methyl β-(4-fluorophenyl)-α-(2-methyl-1-oxopropyl)-2-oxo-3-piperidinepropanoic Acid To a solution of Part A methyl 1-[(1 µl-dimethylethoxy) carbonyl]-β-(4-fluorophenyl)-α-(2-methyl-1-oxopropyl)-2-oxo-3-piperidinepropanoate (45 g, 100 mmol) in dichloromethane (200 mL) which had been cooled to 10° C. was added, dropwise, trifluoroacetic acid (18.9 mL, 250 mmol). The reaction mixture was brought to room temperature and stirred for 2 h. The reaction was quenched with saturated aqueous sodium bicarbonate (200 mL). The phases were separated and the organic layer was washed with 200 mL of aqueous saturated $NaHCO_3$ solution. The organic phase was dried over magnesium sulfate, filtered and concentrated to a white residue. Hexanes (100 mL) were added and the mixture was cooled to 5° C. to effect crystallization. The crystals were collected by filtration, washed with hexane (50 mL) and dried to provide 32 g (91% yield) of methyl β-(4-fluorophenyl)-α-(2-methyl-1-oxopropyl)-2-oxo-3-piperidinepropanoic acid as a mixture of two isomers: IR (KBr) cm$^{-1}$ 3200, 2949, 1738, 1717, 1662, 1510, 847; $^1$H NMR (CDCl$_3$, 400 MHz,) δ 7.22-7.7.20 (m, 4H), 6.95-6.92 (m, 4H), 5.88 (broad, 1H), 5.78 (broad, 1H), 4.52 (d, J=12 Hz, 1H), 4.40 (d, J=12 Hz, 1H), 4.21 (m, 1H), 4.11 (dd, 1H), 3.69 (s, 3H), 3.30 (s, 3H), 3.19-3.18 (m, 4H), 2.83 (m, 1H), 2.52 (m, 3H), 1.86-1.84 (m, 3H), 1.65-1.62 (m, 5H), 1.10 (d, J=4 Hz, 3H), 1.06 (d, J=8 Hz, 3H), 0.84 (d, J=8 Hz, 3H), 0.70 (d, J=4 Hz, 3H); $^{13}$C NMR (CDCl$_3$, 100 MHz) δ 207.2, 206.2, 171.9, 171.8, 168.3, 162.5, 160.1, 135.1, 134.5, 131.1, 130.7, 130.6, 115.2, 115.1, 114.9, 114.8, 61.7, 61.1, 52.9, 52.5, 45.3, 45.3, 45.1, 42.6, 41.9, 41.1, 24.3, 23.9, 21.5, 20.6, 19.5, 19.3, 18.8; HRMS (ESI) calcd. for $C_{19}H_{24}FNO_4$ (M+): 350.1768; found: 350.1779.

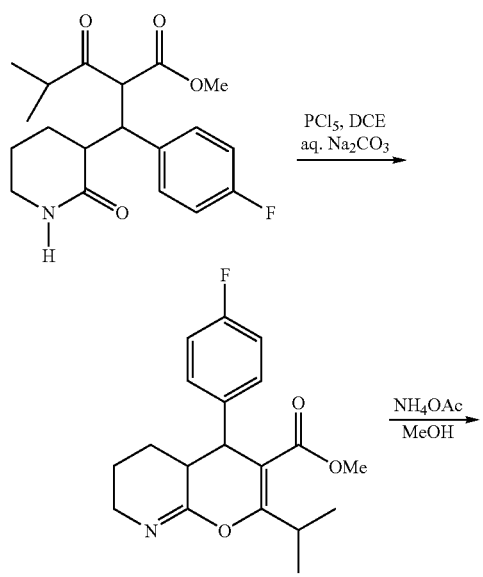

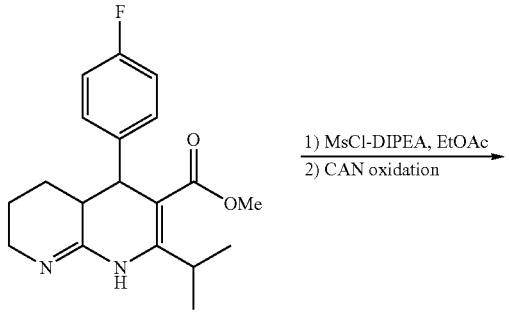

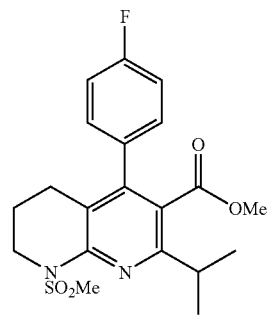

C. Preparation of Methyl 4-(4-fluorophenyl)-2-isopropyl-8-methanesulfonyl-5,6,7,8-tetrahydro-[1,8]naphthyridine-3-carboxylate To a stirred solution of the compound from Part B (3.49 g, 10 mmol) in dichloroethane (25 mL) was added solid phosphorous pentachloride (2.2 g, 1.1 mmol). The mixture was heated to 55° C. for 2.5 h. The reaction mixture was diluted with cold aqueous sodium bicarbonate and the layers were separated. The rich organic layer was washed with 10% aqueous $Na_2CO_3$ (2×50 mL), brine (50 mL), dried over $MgSO_4$ and concentrated under reduced pressure to provide methyl 4-(4-fluorophenyl)-4a,5,6,7-tetrahydro-2-(1-methylethyl)-4H-pyrano[2,3-b]pyridine-3-carboxylate. This material was dissolved in methanol (20 mL) and ammonium acetate (1.56 g, 2.0 eq.) was added. The mixture was heated at 55° C. for 2 h. The reaction was cooled and the methanol was removed under reduced pressure. The residue was dissolved in ethyl acetate (150 mL), and washed with water and brine. The solution was dried over $MgSO_4$ and concentrated to 40 mL. The ethyl acetate solution was cooled to 0° C. and DIPEA (3.5 mL, 2.0 eq.) was added followed by dropwise addition of methanesulfonyl chloride (1.54 mL, 2.0 eq.) over 10 minutes. The reaction was stirred for an additional 20 minutes and the diisopropylethylamine hydrochloride salts were removed by filtration. The filtrate was cooled to 0° C. and aqueous ammonium cerium (IV) nitrate solution (10.4 g dissolved in 10.5 mL water) was added dropwise in 20-30 min. The reaction mixture was diluted with 150 mL of ethyl acetate and washed with 10% aqueous $K_2HPO_4$ (2×100 mL), water (2×100 mL), and brine (50 mL). Concentration of the organic layer under reduced pressure provided 3.4 g of crude product which was passed through small pad of silica gel and crystallized from ethyl acetate:heptane (1:9). The crystallized material was collected by filtration, and washed with heptane to provide title compound which is the same as Example 1 Compound E (1.22 g, 98.2 AP, 30% overall yield): IR (KBr) cm$^{-1}$ 2972, 2961, 1730, 1561, 1511, 1412, 1330, 1271, 1149, 1075, 865;

$^1$H NMR (CDCl$_3$,400 MHz,) δ 7.13-7.08 (m, 4H), 3.91-3.88 (t, J=6.5 Hz, 2H), 3.59 (s, 3H), 3.47 (s, 3H), 3.05 (m, 1H), 2.42 (t, J=6.5 Hz, 2H), 1.93-1.89 (q, 2H), 1.3 (d, J=6.5 Hz, 6H); $^{13}$C NMR (CDCl$_3$, 100 MHz) δ 168.3, 163.3, 159.1, 150.6, 147.4, 132.5, 129.9, 129.8, 123.6, 116.8, 115.5, 115.3, 52.6, 45.7, 44.3, 34.1, 25.9, 23.3, 23.2. HRMS (ESI) calcd. for C$_{20}$H$_{23}$FN$_2$O$_4$S (M+) 407.1441; found 407.1435.

Example 27

Methyl 4-(4-fluorophenyl)-2-isopropyl-1,4,4a,5,6,7-hexahydro-1,8-naphthyridine-3-carboxylate via 4-(4-fluorophenyl)-3-(1-oxo-2-methylpropyl)-3,4,4a,5,6,7-hexahydro-1,8-naphthyridin-2(1H)-one

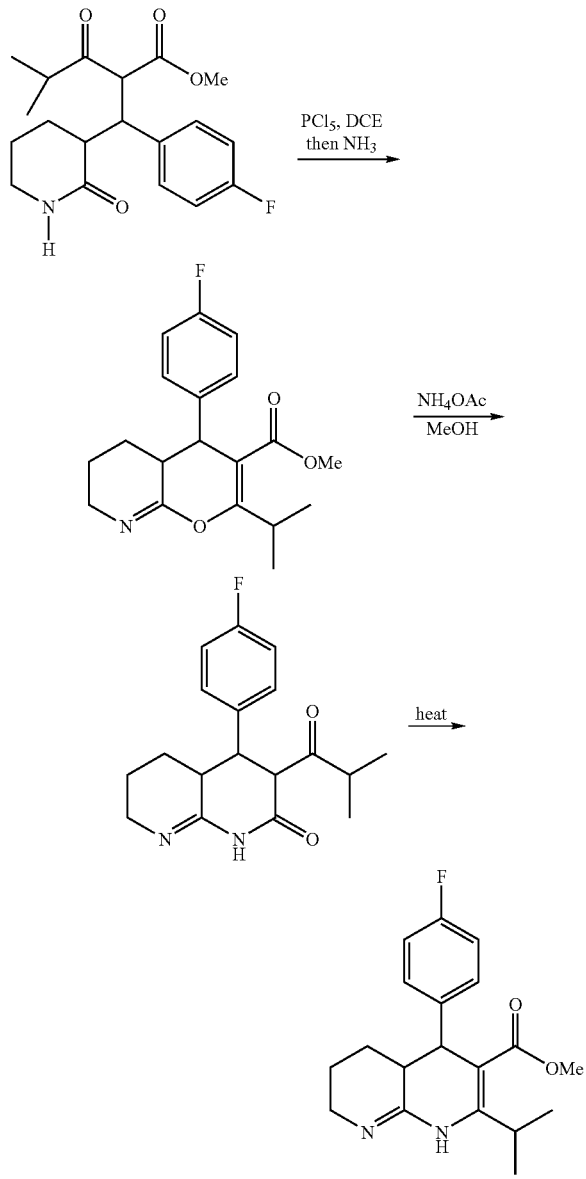

The Part B compound of Example 26 (0.349 g, 1.0 mmol) and phosphorous pentachloride (0.26 g, 1.2 mmol) was dissolved in dichloroethane (4.0 mL) and heated to 70° C. for 2 h at which time less than 10% starting material remained. The reaction mixture was quenched with a solution of NH$_3$ in MeOH (2.5 mL, 2 M, 5.0 mmol) at 0-5 C. The resulting solution was filtered and the filtrate was concentrated to light yellow oil. This residue was dissolved in methanol (5 mL). To this stirred solution was added ammonium acetate (0.3 g, 3.9 mmol). The reaction was stirred at room temperature for 9 h to provide 4-(4-fluorophenyl)-3-(1-oxo-2-methylpropyl)-3,4,4a,5,6,7-hexahydro-1,8-naphthyridin-2(1H)-one. Heating the reaction mixture at 65-70° C. for 7 h provided methyl 4-(4-fluorophenyl)-2-isopropyl-1,4,4a,5,6,7-hexahydro-1,8-naphthyridine-3-carboxylate.

Example 28

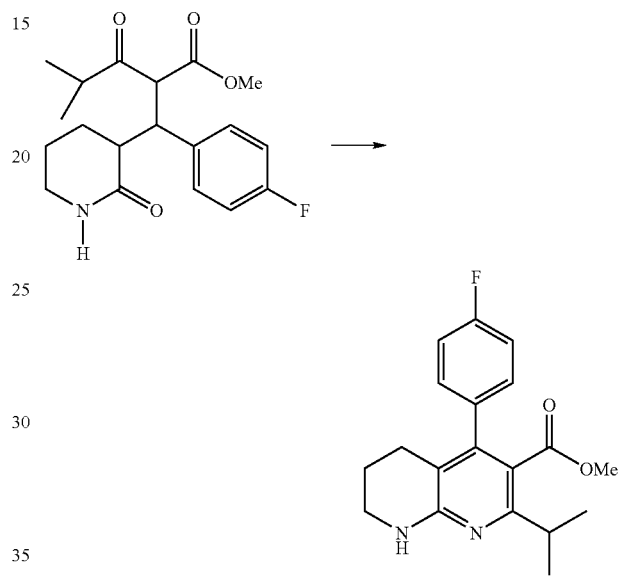

To a stirred solution of Example 26 Compound B (0.7 g, 2.0 mmole, 1.0 eq.) in dichloroethane (8.0 mL) was added PCl$_5$ (0.48 g, 2.4 mmole, 1.2 eq.). The mixture was heated to 65° C. for 2.5 h and was then cooled to 0° C. Ammonia in methanol solution (6.0 mL, 2M, 12 mmole, 6.0 eq) was then added. The precipitated solids were removed by filtration and the filtrate was concentrated under reduced pressure. The residue was redissolved in methanol (10 mL) and ammonium acetate (0.32 g, 4.0 eq) was added. The mixture was heated to 60° C. After 4 h, copper acetate (0.19 g, 1.05 eq.) was added. The mixture was refluxed for and additional 14 h. The reaction mixture was filtered and filtrate was concentrated under reduced pressure. The residue was purified by preparative RP-HPLC to provide title compound which is the same as Example 1 Compound D as a trifluoroacetic acid salt (0.098 g, 30% overall yield) as a colorless solid.

The preceding method works equally well using Example 26 Compound A as the starting material. In this case, removal of the BOC-group occurs under the reaction conditions described: IR (KBr) cm$^{-1}$ 2973-2794 (broad), 1724, 1677; $^1$H NMR (400 MHz, CDCl$_3$) δ 11.14-10.68 (broad, 1H), 7.02-7.03 (m, 4H), 3.52-3.45 (m, 2H), 3.43 (s, 3H), 3.04 (m, 1H), 2.44 (t, 2H), 1.82 (t, 2H), 1.4 (d, 6H, J=6.5 Hz). $^{13}$C NMR (CDCl$_3$, 150 MHz) δ: 166.6, 163.7, 161.2, 152.5, 152.3, 149.9, 131.0, 129.4, 129.3, 117.2, 116.6, 115.9, 115.7, 52.9, 41.4, 32.4, 25.2, 21.4, 19.6; HRMS (ESI) calcd. for C$_{19}$H$_{21}$FN$_2$O$_2$ (M+) 329.1665; found: 329.1658.

Examples 29 to 43

Following the procedures described in Example 1 to 28, and the procedures set out herein, compounds in accordance with the present invention as set out in the following table may be prepared.

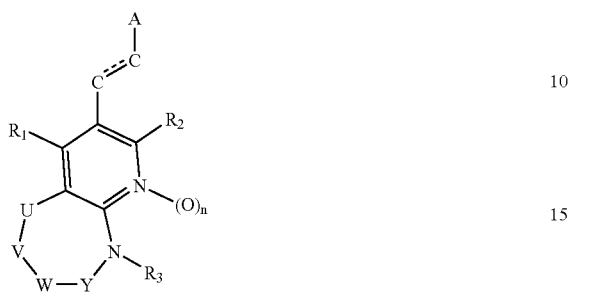

| Example No. | U | V | W | Y | $R_1$ | $R_2$ | $R_3$ | n | |
|---|---|---|---|---|---|---|---|---|---|
| 29 | bond | bond | $CH_2$ | $CH_2$ | H | $CH_3$ | $CH_3$ | 0 | ⫽ |
| 30 | bond | bond | $CH_2$ | $SO_2$ | $CH_3$ | H | H | 0 | ⫽ |
| 31 | bond | bond | $CH_2$ | C=O | $C_6H_5$ | H | $C_2H_5$ | 1 | / |
| 32 | bond | $CH_2$ | $CH_2$ | $CH_2$ | $CH=CH_2$ | n-$C_3H_7$ | $C_6H_5$ | 0 | ⫽ |
| 33 | bond | $CH_2$ | $CH_2$ | $SO_2$ | cyclohexyl | n-$C_4H_9$ | H | 0 | ⫽ |
| 34 | bond | $CH_2$ | $CH_2$ | C=O | $C_2H_5$ | $C_6H_5$ | H | 1 | / |
| 35 | bond | $CH_2$ | | $CH_2$ | $C_6H_5$ | $C_6H_5$ | H | | ⫽ |
| 36 | bond | C=O | $CH_2$ | $CH_2$ | H | c≡c | $CH=CH_2$ | 1 | ⫽ |
| 37 | bond | C=O | $CH_2$ | $SO_2$ | $CH_3$ | $CH_3$ | c≡c | 0 | ⫽ |
| 38 | bond | C=O | $NR_3$ | $SO_2$ | H | cyclohexyl | n-$C_3H_7$ | 0 | ⫽ |
| 39 | $CH_2$ | $CH_2$ | $CH_2$ | $CH_2$ | cyclohexyl | H | $C_2H_5$ | 0 | / |
| 40 | $CH_2$ | $CH_2$ | $CH_2$ | $SO_2$ | pyridyl | H | H | 1 | ⫽ |
| 41 | $CH_2$ | $CH_2$ | $CH_2$ | $SO_2$ | H | H | H | 0 | ⫽ |
| 42 | $CH_2$ | O | $CH_2$ | $CH_2$ | $C_2H_5$ | $CH=CH_2$ | H | 0 | ⫽ |
| 43 | $CH_2$ | C=O | $CH_2$ | $SO_2$ | H | H | $CH_3$ | 0 | ⫽ | where A is or defined herein.

What is claimed is:

1. A compound having the structure

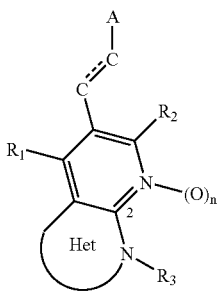

wherein

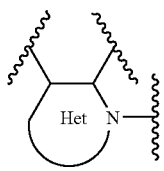

is a 5- or 6-membered fully saturated ring which includes one nitrogen atom which is separated from the N atom of the pyridine ring by a fusion carbon 2,
and wherein
A is

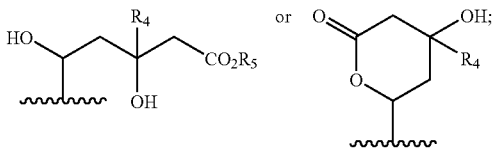

n is 0 or 1;

is

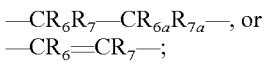

$R_1$ is
  aryl;
$R_2$ is alkyl or cycloalkyl;
$R_3$ is selected from
  H,
  alkyl,
  $C(O)R_8$, or
  $SO_2R_8$;
$R_4$ and $R_5$ are the same or different are independently selected from H or lower alkyl;
$R_6$, $R_7$, $R_{6a}$ and $R_{7a}$ are the same or different are independently selected from H or lower alkyl;
$R_8$ is selected from
  H,
  alkyl,
  alkenyl,
  alkynyl,
  cycloalkyl,
  aryl,
  or heterocyclo (wherein the attachment atom in the heterocyclo group is a carbon);

and including a pharmaceutically acceptable salt thereof where $R_5$ is H, ester thereof, prodrug ester thereof, and all stereoisomers thereof.

2. A compound having the structure

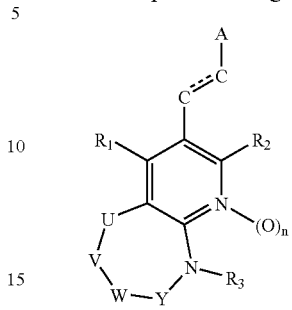

wherein U is a direct bond or $CR^1R^2$ (where $R^1$ and/or $R^2$ are the same or different and are independently H, 'alkyl substituent',

V is a direct bond or $CR^3R^4$ (where $R^3$ and/or $R^4$ are the same or different and are independently H, 'alkyl substituent',

provided that at least one of U and V is a direct bond;
W is $CR^5R^6$ (where $R^5$ and/or $R^6$ are the same or different and are independently H, 'alkyl substituent',

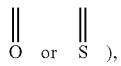

and
Y is $CR^7R^8$ (where $R^7$ and/or $R^8$ are the same or different and are independently H, 'alkyl substituent', $$\underset{O}{\|} \text{ or } \underset{S}{\|}\ ),$$

A is $$HO\underset{OH}{\overset{R_4}{\diagup}}CO_2R_5 \text{ or } O\underset{O}{\diagup}\overset{OH}{\underset{R_4}{\diagup}};$$

n is 0 or 1;

C═══C is
—$CR_6R_7$—$CR_{6a}R_{7a}$—,
or —$CR_6$═$CR_7$—, $R_1$ is
  aryl;
$R_2$ is alkyl or cycloalkyl;
$R_3$ is
  H,
  alkyl,
  $C(O)R_8$, or
  $SO_2R_8$;
$R_4$ and $R_5$ are the same or different and are independently selected from H or lower alkyl;
$R_6$, $R_7$, $R_{6a}$ and $R_{7a}$ are the same or different and are independently selected from H or lower alkyl;
$R_8$ is selected from
  H,
  alkyl,
  alkenyl,
  alkynyl,
  cycloalkyl,
  aryl,
  or heterocyclo (wherein the attachment atom in the heterocyclo group is a carbon);
and including a pharmaceutically acceptable salt thereof where $R_5$ is H, an ester thereof a prodrug ester thereof, and all stereoisomers thereof.

3. The compound as defined in claim 2 wherein U, V, W and Y are as defined below.

|      | U*   | V*   | W*     | Y*     |
|------|------|------|--------|--------|
| i    | bond | bond | $CH_2$ | $CH_2$ |
| iii  | bond | bond | $CH_2$ | C=O    |
| iv   | bond | $CH_2$ | $CH_2$ | $CH_2$ |
| vi   | bond | $CH_2$ | $CH_2$ | C=O    |
| viii | bond | C=O  | $CH_2$ | $CH_2$ |

*one or both of the hydrogen atoms may be replaced by an 'alkyl substituent' group.

4. The compound as defined in claim 2 where the A group is in the form of a free acid, a physiologically acceptable and hydrolyzable ester or δ lactone thereof, or an alkali metal salt, alkaline earth metal salt or an amino acid salt.

5. The compound as defined in claim 1 wherein $R_1$ is aryl; and $R_2$ is selected from alkyl or cycloalkyl;
  $R_4$ is H;
  n is 0.

6. The compound as defined in claim 4 wherein $R_1$ is phenyl which contains 1 or 2 substituents,
  $R_2$ is alkyl or cycloalkyl;
  $R_4$ is H; and

is a trans double bond, in the form of a free acid, an alkali metal salt, or an alkaline earth metal salt or an amino acid salt.

7. The compound as defined in claim 6 wherein $R_1$ is 4-fluorophenyl, 4-fluoro-3-methylphenyl, or 3,5-dimethylphenyl; and
  $R_2$ is isopropyl, t-butyl or cyclopropyl.

8. The compound as defined in claim 2 wherein A has the structure

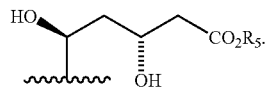

9. The compound as defined in claim 2 in the form of its calcium salt, sodium salt or arginine salt.

10. The compound as defined in claim 2 where
  $R_1$ is aryl;
  $R_2$ is alkyl or cycloalkyl;

C≡C is —CH=CH—, $R_3$ is selected from alkyl, $SO_2R_8$, or $C(O)R_8$,
  $R_4$ is H,
  U is selected from C=O, a bond, or —$CH_2$—, wherein one or both of the hydrogen atoms may be optionally replaced by an 'alkyl substituent',
  V is selected from a bond, or —$CH_2$— wherein one or both of the hydrogen atoms may be optionally replaced by an 'alkyl substituent',
  W is selected from —$CH_2$— wherein one or both of the hydrogen atoms may be optionally replaced by an 'alkyl substituent',
  Y is selected from C=O or —$CH_2$— wherein one or both of the hydrogen atoms may be optionally replaced by an 'alkyl substituent', and
  n is 0.

11. The compound as defined in claim 2 wherein

C≡C is trans

—CH=CH—, $R_1$ is aryl,
  $R_2$ is selected from alkyl or cycloalkyl,
  $R_3$ is selected from alkyl, $SO_2R_8$, or $C(O)R_8$,
  $R_4$ is H,
  U is selected from C=O, a bond, or —$CH_2$— wherein one or both of the hydrogen atoms may be optionally replaced by an 'alkyl substituent',
  V is selected from a bond or —$CH_2$— wherein one or both of the hydrogen atoms may be optionally replaced by an 'alkyl substituent',
  W is —$CH_2$— wherein one or both of the hydrogen atoms may be optionally replaced by an 'alkyl substituent',
  Y is selected from C=O or —$CH_2$— wherein one or both of the hydrogen atoms may be optionally replaced by an 'alkyl substituent', and
  n is 0.

12. The compound as defined in claim 2 wherein
  $R_1$ is 4-fluorophenyl,
  $R_2$ is isopropyl,
  $R_3$ is selected from $SO_2CH_3$, $SO_2CH_2CH_3$, $SO_2$(1-methylimidazol-4-yl), $SO_2CH(CH_3)_2$, $SO_2Ph$, $C(O)CH_3$, or $CH_3$,
  $R_4$ is H,
  U is selected from C=O, a bond or —$CH_2$— wherein one or both of the hydrogen atoms may be optionally replaced by an 'alkyl substituent',
  V is selected from a bond or —$CH_2$— wherein one or both of the hydrogen atoms may be optionally replaced by an 'alkyl substituent',
  W is —$CH_2$— wherein one or both of the hydrogen atoms may be optionally replaced by an 'alkyl substituent', Y is selected from C=O or —CH₂— wherein one or both of the hydrogen atoms may be optionally replaced by a 'alkyl substituent',
n is 0 and
A is

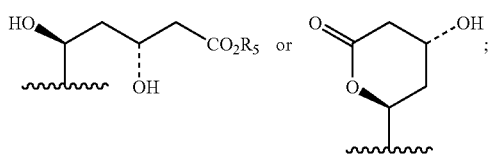

or a alkali metal salt thereof, alkaline earth metal salt or an amino acid salt

13. The compound as defined in claim 2 wherein
$R_1$ is 4-fluorophenyl;
$R_2$ is isopropyl;
$R_3$ is selected from $SO_2CH_3$, $SO_2CHCH_3$, $SO_2$(1-methylimidazol-4-yl), $SO_2CH(CH_3)$, $SO_2Ph$, $C(O)CH_3$ or $CH_3$;
$R_4$ is H; and
U, V, W mid Y are —CH₂CH₂—, —CH₂CH₂ CH₂—, —CH₂CH₂CH₂CH₂—, or

and n is 0.

14. The compound defined in claim 2 having the structure

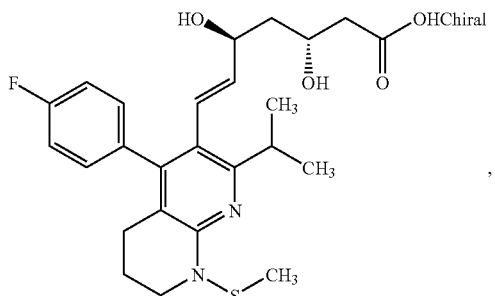

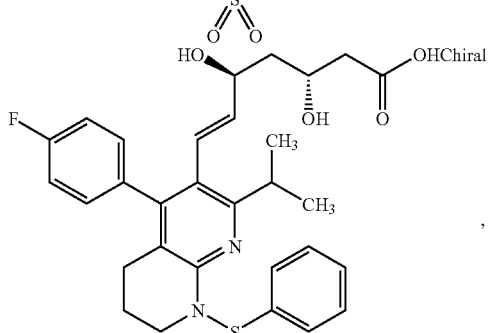

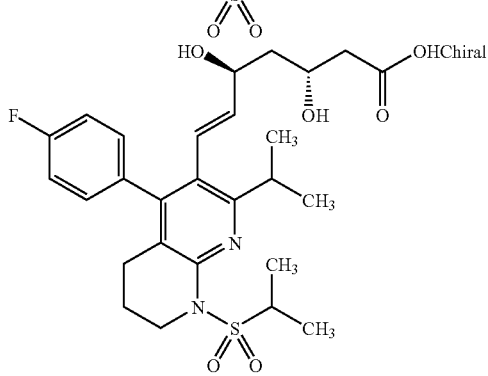

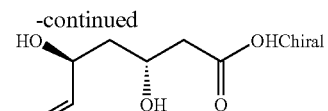

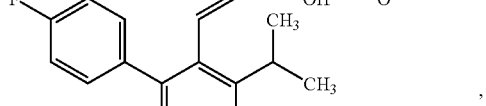

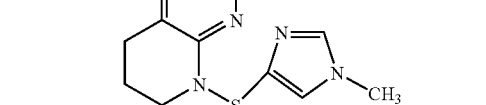

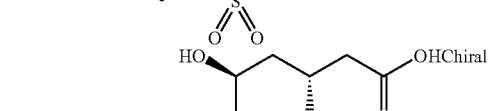

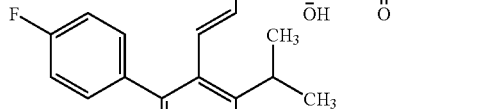

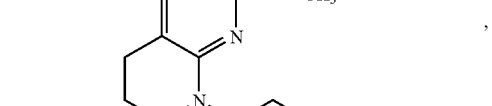

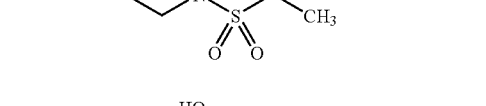

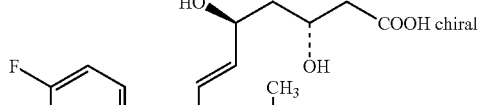

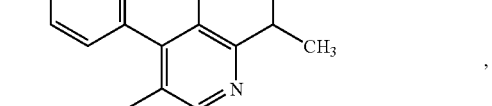

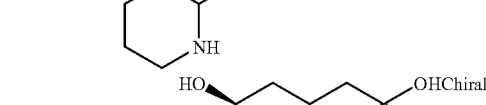

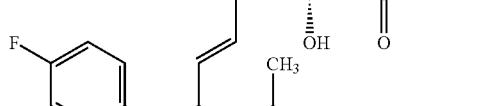

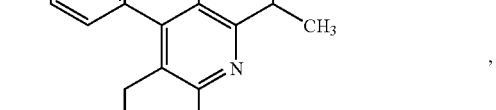

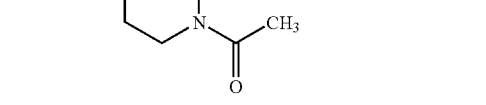

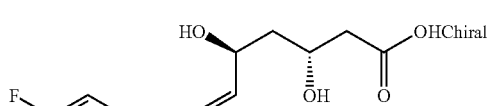

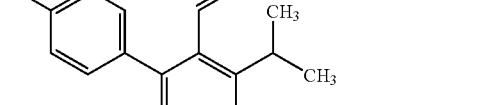

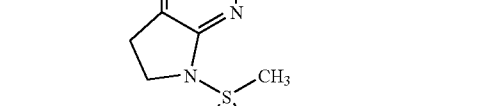

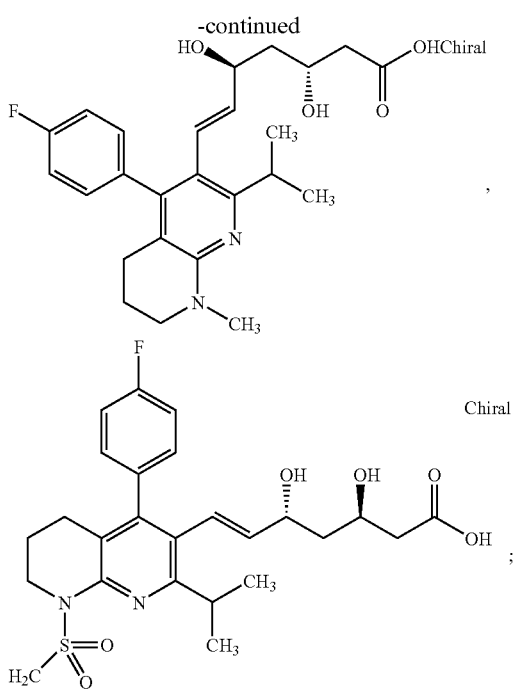

or the name

7-[4-(4-fluorophenyl)-5,6,7,8-tetrahydro-2-(1-methyl-ethyl)-8-(methylsulfonyl)-1,8-naphthyridin-3-yl]-3,5-dihydroxy-(3R,5S,6E)-6-heptenoic acid, monosodium salt;

7-[4-(4-fluorophenyl)-5,6,7,8-tetrahydro-2-(1-methyl-ethyl)-8-(phenylsulfonyl)-1,8-naphthyridin-3-yl]-3,5-dihydroxy-(3R,SS,6E)-6-heptenoic acid, monosodium salt;

7-[4-(4-fluorophenyl)-5,6,7,8-tetrahydro-2-(1-methyl-ethyl)-8-[(1-methylethyl)sulfonyl]-1,8-naphthyridin-3-yl]-3,5-dihydroxy-(3R,5S,6E)-6-heptenoic acid, monosodium salt;

7-[4-(4-fluorophenyl)-5,6,7,8-tetrahydro-2-(1-methyl-ethyl)-8-[(1-methyl-1H-imidazol-4-yl)sulfonyl]-1,8-naphthyridin-3-yl]-3,5-dihydroxy-(3R,5S,6E)-6-heptenoic acid, monosodium salt;

7-[8-(ethylsulfonyl)-4-(4-fluorophenyl)-5,6,7,8-tetrahydro-2-(1-methylethyl)-1,8-naphthyridin-3-yl]-3,5-dihydroxy-(3R,5S,6E)-6-heptenoic acid, monosodium salt;

7-[4-(4-fluorophenyl)-5,6,7,8-tetrahydro-2-(1-methyl-ethyl)-1,8-naphthyridin-3-yl]-3,5-dihydroxy-(3R,5S,6E)-6-heptenoic acid, monosodium salt;

7-[8-acetyl-4-(4-fluorophenyl)-5,6,7,8-tetrahydro-2-(1-methylethyl)-1,8-naphthyridin-3-yl]-3,5-dihydroxy-(3R,5S,6E)-6-heptenoic acid, monosodium salt;

7-[4-(4-fluorophenyl)-2,3-dihydro-6-(1-methylethyl)-1-(methylsulfonyl)-1H-pyrrolo[2,3-b]pyridin-5-yl]-3,5-dihydroxy-(3R,5S,6E)-6-heptenoic acid, monosodium salt;

7-[4-(4-fluorophenyl)-5,6,7,8-tetrahydro-8-methyl-2-(1-methylethyl)-1,8-naphthyridin-3-yl]-3,5-dihydroxy-(3R,5S,6E)-6-heptenoic acid, monosodium salt.

15. A compound having the structure

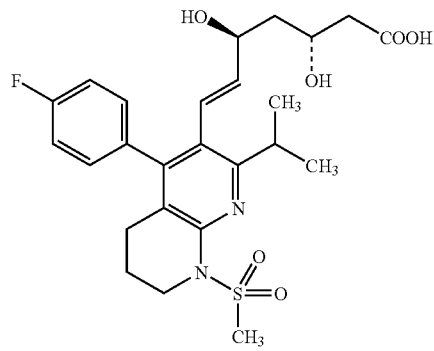

or the name

7-[4-(4-fluorophenyl)-5,6,7,8-tetrahydro-2-(1-methyl-ethyl)-8-(methylsulfonyl)-1,8-naphthyridin-3-yl]-3,5-dihydroxy-(3R,5S,6E)-6-heptenoic acid, monosodium salt.

16. A pharmaceutical composition comprising a compound as defined in claim 1 and a pharmaceutically acceptable carrier therefor.

17. A method for treating hypercholesterolemia, dyslipidemia, hyperlipidemia, hyperlipoproteinemia, LDL Pattern B, LDL Pattern A, or hypertriglyceridemia for inhibiting cholesterol biosynthesis or lowering blood serum cholesterol levels and/or modulating blood serum cholesterol levels, lowering LDL cholesterol and/or increasing HDL cholesterol, or treating dyslipidemia, mixed dyslipidemia, LDL Pattern B, LDL Pattern A, hyperlipidemia, hypercholesterolemia, hypo oc-lipoproteinemia, hyperlipoproteinemia or hypertriglyceridemia, which comprises administering to a mammalian species in need of treatment a therapeutically effective amount of a compound as defined in claim 2.

\* \* \* \* \*